(12) United States Patent
Chen et al.

(10) Patent No.: US 11,661,452 B2
(45) Date of Patent: May 30, 2023

(54) ANTI-LAG-3 ANTIBODY POLYPEPTIDE

(71) Applicants: WUXI BIOLOGICS IRELAND LIMITED, Dublin (IE); CSTONE PHARMACEUTICALS, Grand Cayman (KY); CSTONE PHARMACEUTICALS (SUZHOU) CO., LTD., Suzhou (CN); CSTONE PHARMACEUTICALS (SHANGHAI) CO., LTD., Shanghai (CN)

(72) Inventors: Yunying Chen, Shanghai (CN); Jing Li, Shanghai (CN)

(73) Assignees: WUXI BIOLOGICS IRELAND LIMITED, Dublin (IE); CSTONE PHARMACEUTICALS, Grand Cayman (KY); CSTONE PHARMACEUTICALS (SUZHOU) CO., LTD., Suzhou (CN); CSTONE PHARMACEUTICALS (SHANGHAI) CO., LTD., Shanghai (CN)

( * ) Notice: Subject to any disclaimer, the term of this patent is extended or adjusted under 35 U.S.C. 154(b) by 152 days.

(21) Appl. No.: 16/982,605

(22) PCT Filed: Mar. 15, 2019

(86) PCT No.: PCT/CN2019/078315
§ 371 (c)(1),
(2) Date: Sep. 21, 2020

(87) PCT Pub. No.: WO2019/179365
PCT Pub. Date: Sep. 26, 2019

(65) Prior Publication Data
US 2022/0169722 A1   Jun. 2, 2022

(30) Foreign Application Priority Data

Mar. 20, 2018  (WO) ................ PCT/CN2018/079682

(51) Int. Cl.
| A61K 39/395 | (2006.01) |
| A61K 39/00 | (2006.01) |
| C12Q 1/68 | (2018.01) |
| C12N 5/02 | (2006.01) |
| C12N 1/20 | (2006.01) |
| C12N 15/00 | (2006.01) |
| C07K 16/00 | (2006.01) |
| C07K 16/46 | (2006.01) |
| C07H 21/04 | (2006.01) |
| C07K 16/28 | (2006.01) |
| G01N 33/68 | (2006.01) |

(52) U.S. Cl.
CPC ......... C07K 16/2803 (2013.01); G01N 33/68 (2013.01); A61K 2039/505 (2013.01); C07K 2317/22 (2013.01); C07K 2317/24 (2013.01); C07K 2317/33 (2013.01); C07K 2317/565 (2013.01); C07K 2317/569 (2013.01); C07K 2317/732 (2013.01); C07K 2317/76 (2013.01); C07K 2317/92 (2013.01); G01N 2333/70503 (2013.01)

(58) Field of Classification Search
None
See application file for complete search history.

(56) References Cited

U.S. PATENT DOCUMENTS

| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,624,821 A | 4/1997 | Winter et al. |
| 5,648,260 A | 7/1997 | Winter et al. |
| 5,731,168 A | 3/1998 | Carter et al. |
| 6,005,079 A | 12/1999 | Casterman et al. |
| 6,248,516 B1 | 6/2001 | Winter et al. |
| 2011/0150892 A1 | 6/2011 | Thudium et al. |
| 2015/0259420 A1 | 9/2015 | Triebel et al. |
| 2017/0101472 A1 | 4/2017 | Ullman et al. |
| 2018/0200378 A1* | 7/2018 | Bennett ............... A61K 47/65 |
| 2022/0213192 A1* | 7/2022 | Wu ..................... C07K 16/2803 |

FOREIGN PATENT DOCUMENTS

| CN | 104411723 A | 3/2015 |
| CN | 105793287 A | 7/2016 |
| CN | 105992595 A | 10/2016 |
| CN | 107428836 A | 12/2017 |

(Continued)

OTHER PUBLICATIONS

Liu et al. Liver sinusoidal endothelial cell lectin inhibits CTL-dependent virus clearance in mouse models of viral hepatitis. J Immunol 2013;190:4185-95. (Year: 2013).*
Bae et al. Targeting LAG3/GAL-3 to overcome immunosuppression and enhance anti-tumor immune responses in multiple myeloma. Leukemia vol. 36, pp. 138-154 (2022) (Year: 2022).*
Lauder et al. Enhanced antitumor immunity through sequential targeting of PI3Kσ and LAG3. J Immunother Cancer 2020;8(2):1-13. (Year: 2020).*
Richards, J. O. et al., "Optimization of antibody binding to Fc RIIa enhances macrophage phagocytosis of tumor cells", Mol. Cancer Ther. (Aug. 2008), vol. 7(8), pp. 2517-2527.

(Continued)

*Primary Examiner* — Maher M Haddad
(74) *Attorney, Agent, or Firm* — Jun He Law Offices P.C.; James J. Zhu

(57) ABSTRACT

The present disclosure provides anti-LAG-3 heavy-chain antibody or the antigen-binding domain thereof, isolated polynucleotides encoding the same, pharmaceutical compositions comprising the same, and the uses thereof.

22 Claims, 30 Drawing Sheets
Specification includes a Sequence Listing.

(56) References Cited

FOREIGN PATENT DOCUMENTS

| | | | |
|---|---|---|---|
| JP | 2016516681 A | 6/2016 | |
| JP | 2017516489 A | 6/2017 | |
| JP | 2017532059 A | 11/2017 | |
| TW | 201540727 A | 11/2015 | |
| TW | 201613979 A | 4/2016 | |
| TW | 201726740 A | 8/2017 | |
| WO | 87/00195 A1 | 1/1987 | |
| WO | 90/03430 A1 | 4/1990 | |
| WO | 94/04678 A1 | 3/1994 | |
| WO | 94/25591 A1 | 11/1994 | |
| WO | 94/29351 A2 | 12/1994 | |
| WO | 99/51642 A1 | 10/1999 | |
| WO | 2006/034488 A2 | 3/2006 | |
| WO | 2014183052 A1 | 11/2014 | |
| WO | WO-2015116539 A1 * | 8/2015 | ........... A61K 39/395 |
| WO | 2015/138920 A1 | 9/2015 | |
| WO | 2017/037203 A1 | 3/2017 | |
| WO | 2017087589 A2 | 5/2017 | |
| WO | 2017/149143 A1 | 9/2017 | |
| WO | 2017198212 A1 | 11/2017 | |
| WO | 2017/219995 A1 | 12/2017 | |
| WO | 2018/034227 A1 | 2/2018 | |
| WO | 2018220225 A1 | 12/2018 | |

OTHER PUBLICATIONS

Shields, R. L. et al., "Lack of Fucose on Human IgG1 N-Linked Oligosaccharide Improves Binding to Human FcyRIII and Antibody-dependent Cellular Toxicity", The Journal of Biological Chemistry (Jul. 2002), vol. 277(30), pp. 26733-26740.

Shinkawa, T. et al.,"The absence of fucose but not the presence of galactose or bisecting N-acetylglucosamine of human IgG1 complex-type oligosaccharides shows the critical role of enhancing antibody-dependent cellular cytotoxicity", The Journal of Biological Chemistry (2003), vol. 278(5), pp. 3466-3473.

Duncan, A. R. et al.,"The binding site for C1q on IgG", Nature (Apr. 1988), vol. 332, pp. 738-740.

Batzer, M. A. et al., "Enhanced evolutionary PCR using oligonucleotides with inosine at the 3'-terminus", Nucleic Acids Research (1991), vol. 19(18), pp. 5081.

Ohtsuka, E. et al., "An alternative approach to deoxyoligonucleotides as hybridization probes by insertion of deoxyinosine at ambiguous codon positions", The Journal of Biological Chemistry (1985), vol. 260(5), pp. 2605-2608.

Rossolini, G. M. et al., "Use of deoxyinosine-containing primers vs degenerate primers for polymerase chain reaction based on ambiguous sequence information", Molecular and Cellular Probes (1994), vol. 8, pp. 91-98.

Urlaub, G. et al., "Isolation of Chinese hamster cell mutants deficient in dihydrofolate reductase activity", Proc. Natl. Acad. Sci. USA (1980), vol. 77(7), pp. 4216-4220.

Mather, J. P., "Establishment and Characterization of Two Distinct Mouse Testicular Epithelial Cell Lines", Biology of Reproduction (1980), vol. 23, pp. 243-252.

Mather, J. P. et al., "Culture of Testicular Cells in Hormone-Supplemented Serum-Free Medium", Annals New York Academy of Sciences (1982), vol. 383, pp. 44-68.

Ham, R. G. et al., "[5] Media and growth requirements", Methods in Enzymology (1979), vol. LVIII, pp. 44-93.

Barnes, D. et al., "Methods for growth of cultured cells in serum-free medium", Analytical Biochemistry (1980), vol. 102, pp. 255-270.

Carter, P. et al., "High Level *Escherichia coli* Expression and Production of a Bivalent Humanized Antibody Fragment", Nature Biotechnology (Feb. 1992), vol. 10, pp. 163-167.

Lindmark, R. et al., "Binding of immunoglobulins to protein A and immunoglobulin levels in mammalian sera", Journal of Immunological Methods (1983), vol. 62, pp. 1-13.

Guss, B. et al., "Structure of the IgG-binding regions of streptococcal protein G", The EMBO Journal (1986), vol. 5(7), pp. 1567-1575.

Lymphocyte activation gene 3 protein precursor [*Homo sapiens*], Genbank Accession No. NP_002277.4.

Predicted: lymphocyte activation gene 3 protein [Macaca fascicularis], Genbank Accession No. XP_005570011.1.

Lymphocyte activation gene 3 protein precursor [*Mus musculus*], Genbank Accession No. XP_032505.1.

Saso Cemerski et al., "T cell activation and anti-tumor efficacy of anti-LAG-3 antibodies is independent of LAG-3-MHCII blocking capacity", Journal for Immuno Therapy of Cancer, vol. 3, No. Suppl 2, Nov. 4, 2015 (Nov. 4, 2015), p. 183.

International Search Report of PCT Application No. PCT/CN2019/078315, dated Jun. 21, 2019.

Koch-Nolte, F. et al., "Single domain antibodies from llama effectively and specifically block T cell ecto-ADP-ribosyltransferase ART2.2 in vivo", The FASEB Journal (Nov. 2007), vol. 21, pp. 3490-3498.

Verhoeyen, M. et al., "Reshaping human antibodies: grafting an antilysozyme activity", Science (1988), vol. 239, pp. 1534-1536.

Peter, C. F. et al., "A robust pipeline for rapid production of versatile nanobody repertoires", Nature Methods (Nov. 2, 2014), vol. 11, No. 12, pp. 1253-1260.

Dijkstra, J. M. et al., "Identification and characterization of a second CD4-like gene in teleost fish", Molecular Immunology (2006), vol. 43, pp. 410-419.

Huard, B. et al., "CD4/major histocompatibility complex class II interaction analyzed with CD4- and lymphocyte activation gene-3 (LAG-3)-Ig fusion proteins", Eur. J. Immunol. (1995), vol. 25, pp. 2718-2721.

Baixeras, E. et al., "Characterization of the lymphocyte activation gene 3-encoded protein A new ligand for human leukocyte antigen class II antigens ", J. Exp. Med. (1992), vol. 176, pp. 327-337.

Andrews, L. P. et al., "LAG3 (CD223) as a cancer immunotherapy target", Immunological Reviews (2017), vol. 276, pp. 80-96.

Andreae, S. et al., "Maturation and Activation of Dendritic Cells Induced by Lymphocyte Activation Gene-3 (CD223)", The Journal of Immunology (2002), vol. 168, pp. 3874-3880.

Goldberg, M. V. et al., "LAG-3 in cancer immunotherapy", Current Topics in Microbiology and Immunology (2011), 344, pp. 269-278.

Workman, C. J. et al., "Negative Regulation of T Cell Homeostasis by Lymphocyte Activation Gene-3 (CD223)", The Journal of Immunology (2005), vol. 174, pp. 688-695.

Harmsen, M. M. et al., "Properties, production, and applications of camelid single-domain antibody fragments", Appl. Microbiol. Biotechnol. (2007), vol. 77, pp. 13-22.

Al-Lazikani, B. et al., "Standard conformations for the canonical structures of immunoglobulins", J.Mol.Biol. (1997), vol. 273, pp. 927-948.

Chothia, C. et al., "Domain association in immunoglobulin molecules", J.Mol.Biol. (1985), vol. 186, pp. 651-663.

Chothia, C. et al., "Canonical structures for the hypervariable regions of immunoglobulins", J.Mol.Biol. (1987), vol. 196, pp. 901-917.

Chothia, C. et al., "Conformations of immunoglobulin hypervariable regions", Nature (Dec. 1989), vol. 342, pp. 877-883.

Lefranc, M.-P. et al., "IMGT unique numbering for immunoglobulin and T cell receptor variable domains and Ig superfamily V-like domains". Developmental and Comparative Immunology (2003), vol. 27, pp. 55-77.

Lefranc, M.-P. et al., "IMGT, the international ImMunoGeneTics information system®: a standardized approach for immunogenetics and immunoinformatics", Immunome Research(2005), vol. 1(3), pp. 1-11.

Lefranc, M.-P. et al., "IMGT® Immunoglobulin Repertoire Analysis and Antibody Humanization", Molecular Biology of B Cells (2015), chapter 26, pp. 481-514.

Hamers-Casterman, C. et al., "Naturally occurring antibodies devoid of light chains", Nature (Jun. 1993), vol. 363, pp. 446-448.

Riechmann, L. et al., "Single domain antibodies: comparison of camel VH and camelised human VH domains", Journal of Immunological Methods (1999), vol. 231, pp. 25-38.

(56) References Cited

OTHER PUBLICATIONS

Muyldermans, S., "Single domain camel antibodies: current status", Reviews in Molecular Biotechnology (2001), vol. 74, pp. 277-302.
Nguyen, V. K. et al., "Heavy-chain antibodies in Camelidae; a case of evolutionary innovation", Immunogenetics (2002), vol. 54, pp. 39-47.
Nguyen, V. K. et al., "Heavy-chain only antibodies derived from dromedary are secreted and displayed by mouse B cells", Immunology (2003), vol. 109, pp. 93-101.
LAG-3 protein, partial [*Homo sapiens*], Genbank accession No. GI: 4379038, CAA73914.1.
Lymphocyte-activation gene 3 [Mus musculus], Genbank accession No. GI: 111308743, AAI20592.1.
LAG-3 [Rattus norvegicus], Genbank accession No. GI: 37921547, AAP57397.1.
Altschul, S. F. et al., "Basic local alignment search tool", J.Mol. Biol. (1990), vol. 215, pp. 403-410.
Altschul, S. F. et al., "Gapped BLAST and PSI-BLAST: a new generation of protein database search programs", Nucleic Acids Research(1997), vol. 25, No. 17, p. 3389-3402.
Higgins, D.G. et al., "Using CLUSTAL for Multiple Sequence Alignments", Methods in Enzymology(1996), vol. 266, p. 383-402.
Larkin, M.A. et al., "Clustal W and Clustal X version 2.0", Bioinformatics (2007), vol. 23, No. 21, p. 2947-2948.
Tonegawa, S., "Somatic generation of antibody diversity", Nature (1983), vol. 302, pp. 575-581.
Xu, J. L. et al., "Diversity in the CDR3 Region of VH Is Sufficient for Most Antibody Specificities", Immunity (Jul. 2000), vol. 13, pp. 37-45.
Schier, R. et al., "Isolation of picomolar affinity anti-c-erbB-2 single-chain Fv by molecular evolution of the complementarity determining regions in the center of the antibody binding site", J. Mol. Biol.(1996), vol. 263, pp. 551-567.
Jones, P.T. et al., "Replacing the complementarity-determining regions in a human antibody with those from a mouse", Nature (May 1986), vol. 321, pp. 522-525.
Riechmann, L. et al., "Reshaping human antibodies for therapy", Nature (Mar. 1988), vol. 332, pp. 323-327.
Carter, P. et al., "Humanization of an anti-p185HER2 antibody for human cancer therapy", Proc. Natl. Acad. Sci. USA (May 1992), vol. 89, pp. 4285-4289.
Cunningham, B. C. et al., "High-resolution epitope mapping of hGH-receptor interactions by alanine-scanning mutagenesis", Science (1989), vol. 244, pp. 1081-1085.
Vaughn, D. E. et al., "Structural basis of pH-dependent antibody binding by the neonatal Fc receptor", Structure (1998), vol. 6(1), pp. 63-73.
Yeung, Y. A. et al., "A Therapeutic Anti-VEGF Antibody with Increased Potency Independent of Pharmacokinetic Half-life". Cancer Research (2010), vol. 70(8), pp. 3269-3277.
Hinton, P.R. et al., "An Engineered Human IgG1 Antibody with Longer Serum Half-Life", The Journal of Immunology (2006), vol. 176, pp. 346-356.
Shields, R. L. et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry (2001), vol. 276(9), pp. 6591-6604.
Idusogie, E. E et al., "Mapping of the C1q Binding Site on Rituxan, a Chimeric Antibody with a Human IgG1 Fc", The Journal of Immunology (2000), vol. 164, pp. 4178-4184.
Steurer, W. et al., "Ex vivo coating of islet cell allografts with murine CTLA4/Fc promotes graft tolerance", The Journal of Immunology (1995), vol. 155, pp. 1165-1174.
Idusogie, E. E. et al., "Engineered Antibodies with Increased Activity to Recruit Complement", The Journal of Immunology (2001), vol. 166, pp. 2571-2575.
Lazar, G. A. et al., "Engineered antibody Fc variants with enhanced effector function", PNAS (Mar. 2006), vol. 103(11), pp. 4005-4010.
Ryan, M. C. et al., "Antibody targeting of B-cell maturation antigen on malignant plasma cells", Molecular Cancer Therapeutics (Nov. 2007), vol. 6, pp. 3009-3018.

* cited by examiner

| Ab | EC50 (nM) |
|---|---|
| W3396-R2-2 | 0.2282 |
| W3396-R2-1 | 0.3636 |
| W339-BMK1 | 0.2942 |
| W339-BMK7 | 0.7383 |
| W339-BMK8 | 0.7071 |

| Ab | IC₅₀ (nM) | Inhibition(%) |
|---|---|---|
| W3396-R2-1 | 0.84 | 99.7 |
| W3396-R2-13 | 0.46 | 99.6 |
| W339-BMK1 | 0.76 | 98.2 |
| W339-BMK7 | 1.25 | 95.3 |
| W339-BMK8 | 0.88 | 99.7 |

| Ab | IC50 (nM) |
|---|---|
| W3396-R2-2 | 1.23 |
| W3396-R2-1 | 1.86 |
| W339-BMK1 | 1.95 |
| W339-BMK7 | 2.25 |
| W339-BMK8 | 2.87 |

| Ab | EC$_{50}$ (nM) |
|---|---|
| W3396-R2-2 | 1.36 |
| W3396-R2-1 | 1.08 |
| W339-BMK1 | 1.46 |
| W339-BMK7 | 3.26 |
| W339-BMK8 | 13.1 |

ANTI-LAG-3 ANTIBODY POLYPEPTIDE

PRIORITY CLAIM

The present application claims the priority to PCT Application Number PCT/CN2018/079682, filed on Mar. 20, 2018.

FIELD OF THE INVENTION

The present disclosure generally relates to novel anti-human LAG-3 antibody polypeptide.

BACKGROUND

Lymphocyte Activation Gene-3, or LAG-3 (also known as CD223), is a member of the immunoglobulin supergene family and is structurally similar to CD4 that contains 4 immunoglobulin domains in the extracellular region, however, the amino acid sequence of the two share only 20% homology (Dijkstra et al. (2006) Mol Immunol. 43:410-419). Similar to CD4, LAG-3 interacts with MHC Class II molecules, but with higher affinity (Huard et al. (1995) Eur J Immunol. 25:2718-2721). Unlike CD4, LAG-3 does not interact with the human immunodeficiency virus gp120 protein (Baixeras et al. (1992) J. Exp. Med. 176:327-337).

LAG-3 is not expressed on resting peripheral blood lymphocytes, but is expressed on activated T cells and NK cells. The primary ligand of LAG-3 is MHC-II. In addition, studies have shown that ligands of LAG-3 also include Galectin-3, which is mainly generated by non-immune cells in tumor microenvironment; and sinusoidal endothelial cell lectin (LSECtin), which is generated by hepatocytes and tumor cells (Lawrence P. Andrews (2017) Immunol Rev; 276: 80-96). The binding of LAG-3 and MHC-II can regulate the function of dendritic cells (Andreae et al (2002) J Immunol 168:3874-3880). For T cells, expression upregulation and activation of LAG-3 thereof can inhibit proliferation and function of CD4 and CD8 T cells (Monica V. Goldberg and Charles G. Drake (2011) Curr Top Microbiol Immunol 344: 269-278). Blocking LAG-3 of Treg cells can eliminate the inhibition function of Tregs (Workman and Vignali (2005) J Immunol 174:688-695). Therefore, LAG-3 is considered as an effective candidate target for immunotherapy.

Immune checkpoint inhibitor antibodies, anti-PD-1 and anti-CTLA4 have been shown to have inspiring treating effect for tumors clinically. However, most patients have insufficient response rate to the monotherapy of these immune checkpoint inhibitors. Discovery of combined application with new candidate targets will greatly enhance and improve the effect of existing immunotherapies, and LAG-3 is the most promising candidate target currently. Therefore, there is great need for development of novel anti-LAG-3 antibodies or antibody polypeptides in the field of immunotherapy. Development of heavy chain single domain antibodies with high affinity, due to its good stability and tissue penetration (Harmsen M M, De Haard H J (2007) Appl Microbiol Biotechnol 77(1):13-22), will benefit the expansion of the field of immunotherapy significantly.

BRIEF SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides novel monoclonal anti-LAG-3 antibodies, amino acid and nucleotide sequences thereof, and uses thereof.

In one aspect, the present disclosure provides an isolated antibody polypeptide comprising a heavy chain variable domain that specifically binds to LAG-3, wherein the heavy chain variable domain comprises Complementary Determining Region 1 (CDR1), CDR2 and CDR3, wherein the CDR1 comprises the amino acid sequence of GLTLSQYTMG (SEQ ID NO: 1) or a homologous sequence of at least 80% sequence identity thereof, the CDR2 comprises the amino acid sequence of AIHWTSSVTDYADSVX$_1$G (SEQ ID NO:33) or a homologous sequence of at least 75% sequence identity thereof, and the CDR3 comprises the amino acid sequence of TX$_2$YYTHRGX$_3$FDY (SEQ ID NO:34) or a homologous sequence of at least 75% sequence identity thereof, wherein X$_1$ is K, Y, M, D, or R, X$_2$ is H or W, and X$_3$ is S or P.

In certain embodiments, the present disclosure provides an isolated antibody polypeptide comprising a heavy chain variable domain that specifically binds to LAG-3, wherein the heavy chain variable domain comprises: a CDR1 comprising the sequence of SEQ ID NO: 1, a CDR2 comprising a sequence selected from SEQ ID NOs: 2, 4, 8, 9, and 10, and a CDR3 comprising a sequence selected from SEQ ID NOs: 3, 5, 6, and 7.

In certain embodiments, the present disclosure provides an isolated antibody polypeptide comprising a heavy chain variable domain that specifically binds to LAG-3, wherein the heavy chain variable domain comprises: 1, 2, or 3 heavy chain CDR sequences selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

In certain embodiments, the antibody polypeptide provided herein comprises: a) a heavy chain variable region comprising 1, 2, or 3 CDR sequences selected from SEQ ID NO: 1, SEQ ID NO: 2, and SEQ ID NO: 3; b) a heavy chain variable region comprising 1, 2, or 3 CDR sequences selected from SEQ ID NO: 1, SEQ ID NO: 4, and SEQ ID NO: 5; c) a heavy chain variable region comprising 1, 2, or 3 CDR sequences selected from SEQ ID NO: 1, SEQ ID NO: 4, and SEQ ID NO: 6; d) a heavy chain variable region comprising 1, 2, or 3 CDR sequences selected from SEQ ID NO: 1, SEQ ID NO: 4, and SEQ ID NO: 7; e) a heavy chain variable region comprising 1, 2, or 3 CDR sequences selected from SEQ ID NO: 1, SEQ ID NO: 8, and SEQ ID NO: 7; f) a heavy chain variable region comprising 1, 2, or 3 CDR sequences selected from SEQ ID NO: 1, SEQ ID NO: 9, and SEQ ID NO: 5; g) a heavy chain variable region comprising 1, 2, or 3 CDR sequences selected from SEQ ID NO: 1, SEQ ID NO: 9, and SEQ ID NO: 6; h) a heavy chain variable region comprising 1, 2, or 3 CDR sequences selected from SEQ ID NO: 1, SEQ ID NO: 9, and SEQ ID NO: 7; i) a heavy chain variable region comprising 1, 2, or 3 CDR sequences selected from SEQ ID NO: 1, SEQ ID NO: 10, and SEQ ID NO: 5; or j) a heavy chain variable region comprising 1, 2, or 3 CDR sequences selected from SEQ ID NO: 1, SEQ ID NO: 4, and SEQ ID NO: 3.

In certain embodiments, the heavy chain variable domain comprises a sequence selected from the group consisting of SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 31, and a homologous sequence thereof having at least 80% sequence identity yet retaining specific binding affinity to LAG-3.

In certain embodiments, the antibody polypeptide provided herein further comprises one or more amino acid residue substitutions or modifications yet retaining specific binding affinity to LAG-3. In certain embodiments, at least one of the substitutions or modifications is in one or more of the CDR sequences, and/or in one or more of the VH sequences but not in any of the CDR sequences.

In certain embodiments, the antibody polypeptide provided herein is a single domain antibody or a heavy-chain antibody.

In certain embodiments, the heavy chain variable domain of the antibody polypeptide is derived from a VHH domain.

In certain embodiments, the antibody polypeptide further comprises an immunoglobulin constant region, optionally a constant region of human Ig, or optionally an Fc region of human IgG (e.g. IgG4).

In certain embodiments, the heavy chain variable domain is of camelid origin or is humanized.

In certain embodiments, the antibody polypeptide is a nanobody.

In certain embodiments, the antibody polypeptide is capable of specifically binding to human LAG-3, mouse LAG-3, and cyno LAG-3. In certain embodiments, the antibody polypeptide is capable of specifically blocking the binding of human LAG-3, mouse LAG-3, and cyno LAG-3 to their ligands.

In certain embodiments, the antibody polypeptide is capable of specifically binding to human LAG-3 expressed on a cell surface at a $K_D$ value of no more than $5 \times 10^{-9}$, $2 \times 10^{-10}$, $2.5 \times 10^{-12}$ M as measured by surface plasmon resonance (SPR).

In certain embodiments, the antibody polypeptide is capable of specifically binding to human LAG-3 expressed on a cell surface at a $K_D$ value of no more than $10^{-9}$, $5 \times 10^{-10}$, $6 \times 10^{-11}$ M as measured by flow cytometry.

In certain embodiments, the antibody polypeptide is capable of specifically binding to cynomolgus monkey LAG-3, and/or mouse LAG-3.

In certain embodiments, the antibody polypeptide is linked to one or more conjugate moieties. In certain embodiments, the conjugate moiety comprises a clearance-modifying agent, a chemotherapeutic agent, a toxin, a radioactive isotope, a lanthanide, a luminescent label, a fluorescent label, an enzyme-substrate label, a DNA-alkylators, a topoisomerase inhibitor, a tubulin-binders, or other anticancer drugs.

In another aspect, the present disclosure further provides an antibody or an antigen-binding fragment thereof, which competes for the same epitope with the antibody polypeptide provided herein.

In another aspect, the present disclosure further provides a pharmaceutical composition comprising the antibody polypeptide provided herein, the antibody or an antigen-binding fragment thereof provided herein, and a pharmaceutically acceptable carrier.

In another aspect, the present disclosure further provides an isolated polynucleotide encoding the antibody polypeptide provided herein. In certain embodiments, the isolated polynucleotide comprises a nucleotide sequence selecting from a group consisting of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, and SEQ ID NO: 32, and/or a homologous sequence thereof having at least 80% (e.g. at least 85%, 88%, 90%, 92%, 93%, 94%, 95%, 96%, 97%, 98%, or 99%) sequence identity, and/or a variant thereof having only degenerate substitutions.

In another aspect, the present disclosure further provides a vector comprising the isolated polynucleotide provided herein.

In another aspect, the present disclosure further provides a host cell comprising the vector provided herein.

In another aspect, the present disclosure further provides a method of expressing the antibody polypeptide provided herein, comprising culturing the host cell provided herein under the condition at which the vector provided herein is expressed.

In another aspect, the present disclosure further provides a method of treating a disease or condition in a subject that would benefit from modulation of LAG-3 activity, comprising administering to the subject a therapeutically effective amount of the antibody polypeptide provided herein or the pharmaceutical composition provided herein. In certain embodiments, the disease or condition is a LAG-3 related disease or condition. In certain embodiments, the disease or condition is cancer, autoimmune disease, or infectious disease.

In certain embodiments, the cancer is glioblastoma, a hematologic neoplasm, metastatic melanoma, Burkitt's lymphoma (BL), multiple myeloma (MM), B chronic lymphocytic leukemia (B-CLL), B and T acute lymphocytic leukemia (ALL), T cell lymphoma (TCL), hairy cell leukemia (HCL), Hodgkin's Lymphoma (HL), melanoma, mesothelioma, Wilm's cancer, renal cancer, prostate cancer, breast cancer, colon cancer, colorectal cancer, lung cancer, bone cancer, pancreatic cancer, hepatic cell carcinoma, skin cancer, endometrial cancer, carcinoid cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia (AML), chronic myeloid leukemia (CML), acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, Ewing's sarcoma, chondrosarcoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, epidermoid cancer, squamous cell cancer, environmentally induced cancer, cancer induced by asbestos, and a metastatic cancer.

In certain embodiments, the infectious disease is HIV, Hepatitis (A, B, & C), human papilloma virus (HPV), lymphocytic choriomeningitis virus (LCMV) and simian immunodeficiency virus (SIV), Influenza, Herpes, Giardia, Malaria, *Leishmania, Staphylococcus aureus, Pseudomonas aeruginosa*, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, arboviral encephalitis virus, chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, Lyme disease bacteria, *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii*, and *Nippostrongylus brasiliensis*.

In certain embodiments, the autoimmune disease is Alzheimer's disease, allergy, asthma, celiac disease, Crohn's disease, Grave's disease, inflammatory bowel disease (IBD), lupus, multiple sclerosis, Myasthenia Gravis, polymyalgia rheumatica, rheumatoid arthritis, type I diabetes, and vasculitis.

In certain embodiments, the subject is human.

In certain embodiments, the administration is via oral, nasal, intravenous, subcutaneous, sublingual, or intramuscular administration.

In another aspect, the present disclosure further provides a method of modulating LAG-3 activity in a LAG-3-expressing cell, comprising exposing the LAG-3-expressing cell to the antibody polypeptide provided herein.

In another aspect, the present disclosure further provides a method of detecting presence or amount of LAG-3 in a sample, comprising contacting the sample with the antibody polypeptide provided herein, and determining the presence or the amount of LAG-3 in the sample.

In another aspect, the present disclosure further provides a method of diagnosing a LAG-3 related disease or condition in a subject, comprising: a) contacting a sample obtained from the subject with the antibody polypeptide provided herein; b) determining presence or amount of LAG-3 in the sample; and c) correlating the presence or the amount of LAG-3 to existence or status of the LAG-3 related disease or condition in the subject.

In another aspect, the present disclosure further provides use of the antibody polypeptide provided herein in the manufacture of a medicament for treating a LAG-3 related disease or condition in a subject.

In another aspect, the present disclosure further provides use of the antibody polypeptide provided herein in the manufacture of a diagnostic reagent for diagnosing a LAG-3 related disease or condition.

In another aspect, the present disclosure further provides a kit comprising the antibody polypeptide provided herein, useful in detecting LAG-3.

BRIEF DESCRIPTION OF FIGURES

FIG. 12A shows modeling of LAG-3 (based on PDB: 5FLU). FIG. 12B shows hotspots of W339-BMK1 labeled on the modeled structure (Black: fold change <0.55, Gray with white dot: fold change 0.55-0.75).

FIG. 12C shows hotspots of W339-BMK7 labeled on the modeled structure (Black: fold change <0.55, Gray with white dot: fold change 0.55-0.75). FIG. 12D shows hotspots of W339-BMK8 labeled on the modeled structure (Black: fold change <0.55, Gray with white dot: fold change 0.55-0.75). FIG. 12E shows hotspots of W3396-R2-2 labeled on the modeled structure (Black: fold change <0.55, Gray with white dot: fold change 0.55-0.75).

DETAILED DESCRIPTION OF THE INVENTION

Figure 1:
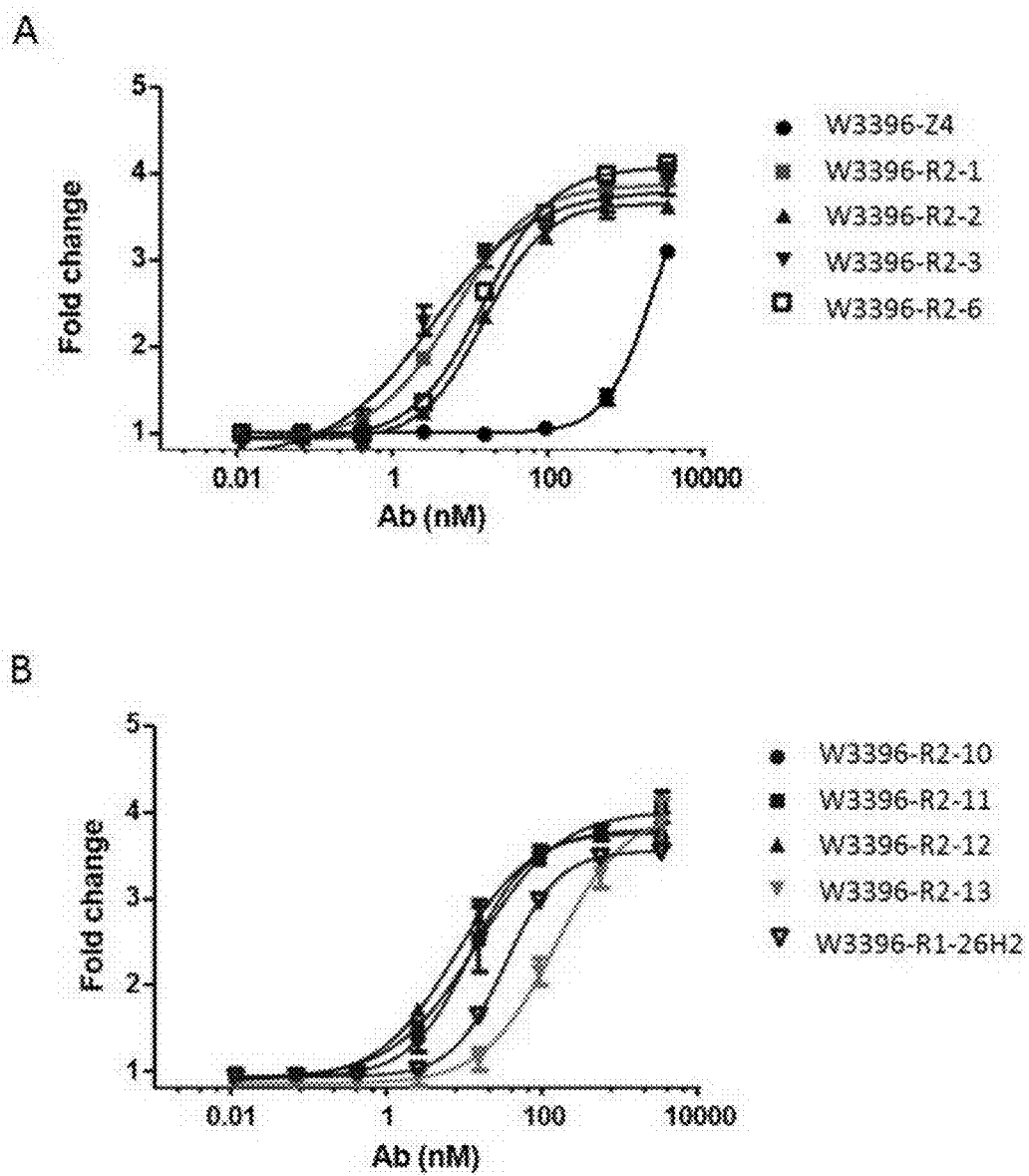
FIGS. 1A and 1B show that the 9 affinity matured VHH antibody (Abs) (W3396-R2-1, W3396-R2-2, W3396-R2-3, W3396-R2-6, W3396-R2-10, W3396-R2-11, W3396-R2-12, W3396-R2-13 and W3396-R2-26H2) show enhanced reactivity as compared with humanized parental VHH Ab (W3396-Z4), as measured by the IL-2 luciferase reporter gene assay (RGA).

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, monovalent antibody, or antibody that binds to a specific antigen. The term "antibody" as used herein intends to encompass broadly to both conventional four-chain antibodies and also less-conventional antibodies that do not have four chains (such as antibodies naturally devoid of light chains).

A conventional intact antibody is a heterotetramer comprising two heavy (H) chains and two light (L) chains. Mammalian heavy chains are classified as alpha, delta, epsilon, gamma, and mu, each heavy chain consists of a variable region ($V_H$) and a first, second, and third constant region ($C_{H1}$, $C_{H2}$, $C_{H3}$, respectively); mammalian light chains are classified as X or x, while each light chain consists of a variable region ($V_L$) and a constant region. The conventional antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., J. Mol. Biol., 273(4), 927 (1997); Chothia, C. et al., J Mol Biol. Dec. 5; 186(3):651-63 (1985); Chothia, C. and Lesk, A. M., J. Mol. Biol., 196,901 (1987); Chothia, C. et al., Nature. Dec. 21-28; 342(6252):877-83 (1989); Kabat E. A. et al., Sequences of Proteins of Immunological Interest, 5th Ed. Public Health Service, National Institutes of Health, Bethesda, Md. (1991); Marie-Paule Lefranc et al, Developmental and Comparative Immunology, 27: 55-77 (2003); Marie-Paule Lefranc et al, Immunome Research, 1(3), (2005); Marie-Paule Lefranc, Molecular Biology of B cells (second edition), chapter 26, 481-514, (2015)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

Unlike conventional antibodies which are heterotetramers, there are homodimeric immunoglobulins and are naturally devoid of light chains. Such antibodies are found in, for example, camelids (camel, dromedary, llama, alpaca, etc.), and are also called heavy-chain antibodies with a molecular weight of about 80 kD (Hamers-Casterman C. et al., 1993, Nature, 363:446-448).

The term "antibody polypeptide" as used herein refers to an antigen-binding protein or polypeptide comprising an antibody fragment (such as a CDR, and/or a variable region sequence). An antibody polypeptide can comprise or can be, for example, a heavy-chain antibody (a VHH antibody), a variable domain of a heavy-chain antibody, a VHH domain, or a single domain antibody containing a single variable domain. The antibody polypeptide may further comprise additional domains such as a constant region, an Fc domain, and/or a second variable domain specifically binding to a different antigen or different epitope.

"Heavy-chain antibody" and "VHH antibody" are used interchangeably used herein, and refers to an antibody that contains two $V_H$ domains and no light chains (Riechmann L. and Muyldermans S., J Immunol Methods. Dec. 10; 231(1-2):25-38 (1999); Muyldermans S., J Biotechnol. Jun.; 74 (4):277-302 (2001); WO94/04678; WO94/25591; U.S. Pat. No. 6,005,079). Although devoid of light chains, heavy chain antibodies have an authentic antigen-binding repertoire (Hamers-Casterman C. et al., 1993, Nature, 363:446-448; Nguyen V K. et al. Immunogenetics. Apr.; 54(1):39-47 (2002); Nguyen V K. et al. Immunology. May; 109(1):93-101 (2003)).

"VHH domain" as used herein refers to the heavy chain variable domain derived from a heavy-chain antibody. VHH domain represents the smallest known antigen-binding unit generated by adaptive immune responses (Koch-Nolte F. et al., FASEB J. Nov.; 21(13):3490-8. Epub 2007 Jun. 15 (2007)).

A "single domain antibody" refers to an antibody fragment containing only a single variable region of a heavy chain or a single variable region of a light chain. In certain embodiments, the single domain antibody has or consists of only a single heavy-chain variable domain of a heavy-chain antibody.

A "nanobody" refers to an antibody fragment that consists of a VHH domain from a heavy-chain antibody and two constant domains, CH2 and CH3.

In certain instances, two or more VHH domains can be covalently joined with a peptide linker to create a bivalent or multivalent domain antibody. The two VHH domains of a bivalent domain antibody may target the same or different antigens.

The term "bivalent" as used herein refers to an antibody or antibody polypeptide having two antigen-binding sites; the term "monovalent" refers to an antibody or antibody polypeptide having only one single antigen-binding site; and the term "multivalent" refers to an antibody or antibody polypeptide having multiple antigen-binding sites. In some embodiments, the antibody or antibody polypeptide is bivalent or multivalent.

The term "chimeric" as used herein, means an antibody or antibody polypeptide having a portion of sequence derived from one species, and the rest of the sequence derived from a different species. In an illustrative example, a chimeric antibody may comprise a constant region derived from human and a variable region from a non-human animal, such as from camelidae. In some embodiments, the non-human animal is a mammal, for example, a camelidae, a mouse, a rat, a rabbit, a goat, a sheep, a guinea pig, or a hamster.

The term "humanized" as used herein means that the antibody comprises CDRs derived from non-human animals, FR regions derived from human, and when applicable, the constant regions derived from human.

"LAG-3" as used herein, can be derived from any vertebrate source, including mammals such as primates (e.g. humans, monkeys) and rodents (e.g., mice and rats). Exemplary sequence of human LAG-3 includes human LAG-3 protein (partial, Genbank accession No: GI: 4379038). Exemplary sequence of LAG-3 includes *Mus musculus* (mouse) LAG-3 protein (Genbank accession No: GI: 111308743); *Rattus norvegicus* (Rat) LAG-3 (Genbank accession No: GI: 37921547).

The term "LAG-3" as used herein is intended to encompass any form of LAG-3, for example, 1) native unprocessed LAG-3 molecule, "full-length" LAG-3 chain or naturally occurring variants of LAG-3, including, for example, splice variants or allelic variants; 2) any form of LAG-3 that results from processing in the cell; or 3) full length, a fragment (e.g., a truncated form, an extracellular/transmembrane domain) or a modified form (e.g. a mutated form, a glycosylated/PEGylated, a His-tag/immunofluorescence fused form) of LAG-3 subunit generated through recombinant method.

The term "anti-LAG-3" antibody polypeptide refers to an antibody polypeptide that is capable of specific binding LAG-3 (e.g. human or monkey or mouse or rat LAG-3).

The term "specific binding" or "specifically binds" as used herein refers to a non-random binding reaction between two molecules, such as for example between an antibody and an antigen. In certain embodiments, the antibody polypeptides provided herein specifically bind to human and/or LAG-3 with a binding affinity ($K_D$) of $\leq 10^{-6}$ M (e.g., $\leq 5\times 10^{-7}$ M, $\leq 2\times 10^{-7}$ M, $\leq 10^{-7}$ M, $\leq 5\times 10^{-8}$ M, $\leq 2\times 10^{-8}$ M, $\leq 10^{-8}$ M, $\leq 5\times 10^{-9}$ M, $\leq 4\times 10^{-9}$M, $\leq 3\times 10^{-9}$M, $\leq 2\times 10^{-9}$ M, or $\leq 10^{-9}$ M). $K_D$ used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the $K_D$ value can be appropriately determined by using flow cytometry.

The ability to "block binding" or "compete for the same epitope" as used herein refers to the ability of an antibody polypeptide to inhibit the binding interaction between two molecules (e.g. human LAG-3 and an anti-LAG-3 antibody) to any detectable degree. In certain embodiments, an antibody polypeptide that blocks binding between two molecules inhibits the binding interaction between the two molecules by at least 85%, or at least 90%. In certain embodiments, this inhibition may be greater than 85%, or greater than 90%.

The term "epitope" as used herein refers to the specific group of atoms or amino acids on an antigen to which an antibody binds. Two antibodies may bind the same or a closely related epitope within an antigen if they exhibit competitive binding for the antigen. For example, if an antibody polypeptide blocks binding of a reference antibody to the antigen by at least 85%, or at least 90%, or at least 95%, then the antibody polypeptide may be considered to bind the same/closely related epitope as the reference antibody.

Those skilled in the art will recognize that it is possible to determine, without undue experimentation, if a given antibody binds to the same epitope as the antibody of present disclosure (e.g., camelid monoclonal antibody W3396-parent, and humanized antibody W3396-Z4, W3396-R2-1, W3396-R2-2, W3396-R2-3, W3396-R2-6, W3396-R2-10, W3396-R2-11, W3396-R2-12, W3396-R2-13, and W3396-R1-26H2) by ascertaining whether the former prevents the latter from binding to a LAG-3 antigen polypeptide. If the given antibody competes with the antibody of present disclosure, as shown by a decrease in binding by the antibody of present disclosure to the LAG-3 antigen polypeptide, then the two antibodies bind to the same, or a closely related, epitope. Or if the binding of a given antibody to the LAG-3 antigen polypeptide was inhibited by the antibody of present disclosure, then the two antibodies bind to the same, or a closely related, epitope.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "homologue" and "homologous" as used herein are interchangeable and refer to nucleic acid sequences (or its complementary strand) or amino acid sequences that have sequence identity of at least 80% (e.g., at least 85%, 88%, 90%, 91%, 92%, 93%, 94%, 95%, 96%, 97%, 98%, 99%) to another sequences when optimally aligned.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated" nucleic acid sequence" refers to the sequence of an isolated nucleic acid molecule. In certain embodiments, an "isolated antibody polypeptide" refers to the antibody polypeptide having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the antibody polypeptide, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pProl8, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

A "LAG-3-related" disease or condition as used herein refers to any disease or condition caused by, exacerbated by, or otherwise linked to increased or decreased expression or activities of LAG-3. In some embodiments, the LAG-3 related condition is immune-related disorder, such as, for example, cancer, autoimmune disease, or infectious disease.

"Cancer" as used herein refers to any medical condition characterized by malignant cell growth or neoplasm, abnormal proliferation, infiltration or metastasis, and includes both solid tumors and non-solid cancers (hematologic malignancies) such as leukemia. As used herein "solid tumor" refers to a solid mass of neoplastic and/or malignant cells. Examples of cancer or tumors include hematological malignancies, oral carcinomas (for example of the lip, tongue or pharynx), digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In certain embodiments, the cancer is selected from ovarian cancer, breast cancer, head and neck cancer, renal cancer, bladder cancer, hepatocellular cancer, and colorectal cancer. In certain embodiments, the cancer is selected from a lymphoma, Hodgkin's lymphoma, non-Hodgkin's lymphoma and B-cell lymphoma.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-LAG-3 Antibody Polypeptide

In one aspect, the present disclosure provides antibody polypeptides comprising a heavy chain variable domain that specifically bind to LAG-3 (e.g. human LAG-3), wherein the heavy chain variable domain comprises CDR1, CDR2 and CDR3, wherein the CDR1 comprises GLTLSQYTMG (SEQ ID NO: 1), the CDR2 comprises AIHWTSSVTDYADSVX$_1$G (SEQ ID NO: 33), and the CDR3 comprises TX$_2$YYTHRGX$_3$FDY (SEQ ID NO: 34), wherein X$_1$ is K, Y, M, D, or R, X$_2$ is H or W, and X$_3$ is S or P. In certain embodiments, the present disclosure further encompass antibody polypeptides having no more than one, two or three amino acid residue substitution to any of SEQ ID NOs: 1, 33 and 34, wherein X$_1$ is K, Y, M, D, or R, X$_2$ is H or W, and X$_3$ is S or P.

In certain embodiments, the present disclosure provides anti-LAG-3 antibody polypeptides comprising one or more (e.g. 1, 2, or 3) CDR sequences of an anti-LAG-3 VHH antibody W3396-parent, W3396-Z4, W3396-R2-1, W3396-R2-2, W3396-R2-3, W3396-R2-6, W3396-R2-10, W3396-R2-11, W3396-R2-12, W3396-R2-13, and W3396-R1-26H2.

"W3396-parent" as used herein refers to a VHH antibody having a heavy chain variable region comprising the sequence of SEQ ID NO: 11.

"W3396-Z4" as used herein refers to a humanized VHH antibody based on W3396 that comprises a heavy chain variable region comprising the sequence of SEQ ID NO: 13.

"W3396-R2-1" as used herein refers to an affinity matured VHH antibody based on W3396-Z4 that comprises a heavy chain variable region comprising the sequence of SEQ ID NO: 15.

"W3396-R2-2" as used herein refers to an affinity matured VHH antibody based on W3396-Z4 that comprises a heavy chain variable region comprising the sequence of SEQ ID NO: 17.

"W3396-R2-3" as used herein refers to an affinity matured VHH antibody based on W3396-Z4 that comprises a heavy chain variable region comprising the sequence of SEQ ID NO: 19.

"W3396-R2-6" as used herein refers to an affinity matured VHH antibody based on W3396-Z4 that comprises a heavy chain variable region comprising the sequence of SEQ ID NO: 21.

"W3396-R2-10" as used herein refers to an affinity matured VHH antibody based on W3396-Z4 that comprises a heavy chain variable region comprising the sequence of SEQ ID NO: 23.

"W3396-R2-11" as used herein refers to an affinity matured VHH antibody based on W3396-Z4 that comprises a heavy chain variable region comprising the sequence of SEQ ID NO: 25.

"W3396-R2-12" as used herein refers to an affinity matured VHH antibody based on W3396-Z4 that comprises a heavy chain variable region comprising the sequence of SEQ ID NO: 27.

"W3396-R2-13" as used herein refers to an affinity matured VHH antibody based on W3396-Z4 that comprises a heavy chain variable region comprising the sequence of SEQ ID NO: 29.

"W3396-R1-26H2" as used herein refers to a humanized VHH antibody based on W3396-Z4 that comprises a heavy chain variable region comprising the sequence of SEQ ID NO: 31.

Humanized antibody W3396-Z4, has comparable affinity to LAG-3 as compared with its parent antibody W3396. Affinity matured antibodies W3396-R2-1, W3396-R2-2, W3396-R2-3, W3396-R2-6, W3396-R2-10, W3396-R2-11, W3396-R2-12, W3396-R2-13, and/or W3396-R1-26H2 have better affinity to LAG-3 as compared with their humanized parent antibody W3396-Z4.

Table 1 shows the CDR sequences of these 11 anti-LAG-3 single domain antibodies. The heavy chain variable region sequences are also provided below in Table 2 and Table 3.

TABLE 1

CDR amino acid sequences

| | | CDR1<br>SEQ ID NO: 1 | CDR2<br>SEQ ID NO: 2 | CDR3<br>SEQ ID NO: 3 |
|---|---|---|---|---|
| W3396-parent | HCDR | GLTLSQYTMG | AIEWTSSVTDY<br>ADSVKG | THYYTHRGSFD<br>Y |
| W3396-Z4 | HCDR | SEQ ID NO: 1<br>GLTLSQYTMG | SEQ ID NO: 2<br>AITIWTSSVTDY<br>ADSVKG | SEQ ID NO: 3<br>THYYTHRGSF<br>DY |
| W3396-R2-1 | HCDR | SEQ ID NO: 1<br>GLTLSQYTMG | SEQ ID NO: 4<br>AITIWTSSVTDY<br>ADSVYG | SEQ ID NO: 5<br>TWYYTHRGSF<br>DY |
| W3396-R2-2 | HCDR | SEQ ID NO: 1<br>GLTLSQYTMG | SEQ ID NO: 4<br>AITIWTSSVTDY<br>ADSVYG | SEQ ID NO: 6<br>THYYTHRGPF<br>DY |
| W3396-R2-3 | HCDR | SEQ ID NO: 1<br>GLTLSQYTMG | SEQ ID NO: 4<br>AITIWTSSVTDY<br>ADSVYG | SEQ ID NO: 7<br>TWYYTHRGPF<br>DY |
| W3396-R2-6 | HCDR | SEQ ID NO: 1<br>GLTLSQYTMG | SEQ ID NO: 8<br>AITIWTSSVTDY<br>ADSVMG | SEQ ID NO: 7<br>TWYYTHRGPF<br>DY |
| W3396-R2-10 | HCDR | SEQ ID NO: 1<br>GLTLSQYTMG | SEQ ID NO: 9<br>AITIWTSSVTDY<br>ADSVDG | SEQ ID NO: 5<br>TWYYTHRGSF<br>DY |
| W3396-R2-11 | HCDR | SEQ ID NO: 1<br>GLTLSQYTMG | SEQ ID NO: 9<br>AITIWTSSVTDY<br>ADSVDG | SEQ ID NO: 6<br>THYYTHRGPF<br>DY |
| W3396-R2-12 | HCDR | SEQ ID NO: 1<br>GLTLSQYTMG | SEQ ID NO: 9<br>AITIWTSSVTDY<br>ADSVDG | SEQ ID NO: 7<br>TWYYTHRGPF<br>DY |
| W3396-R2-13 | HCDR | SEQ ID NO: 1<br>GLTLSQYTMG | SEQ ID NO: 10<br>AITIWTSSVTDY<br>ADSVRG | SEQ ID NO: 5<br>TWYYTHRGSF<br>DY |

TABLE 1-continued

| | | CDR1<br>SEQ ID NO: 1 | CDR2<br>SEQ ID NO: 2 | CDR3<br>SEQ ID NO: 3 |
|---|---|---|---|---|
| W3396-R1-26112 | HCDR | SEQ ID NO: 1<br>GLTLSQYTMG | SEQ ID NO: 4<br>AIHWTSSVTDY<br>ADSVYG | SEQ ID NO: 3<br>THYYTHRGSFD<br>Y |

TABLE 2

Variable region amino acid sequences

| | VH |
|---|---|
| W3396-parent | SEQ ID NO: 11<br>QVQLVESGGGLVQAGGSLRLSCAASGLTLSQYTMGWFRQAPGKERELVAAIHWTSSVTDYADSVKGRFTISRDDARNTGYLQMNSLKFEDTAVYYCAATHYYTHRGSFDYWGQTQVTVSS |
| W3396-Z4 | SEQ ID NO: 13<br>QVQLVESGGGVVQPGGSLRLSCAASGLTLSQYTMGWFRQAPGKERELVAAIHWTSSVTDYADSVKGRFTISRDDSKNTGYLQMNSLRAEDTAVYYCAATHYYTHRGSFDYWGQTLVTVSS |
| W-3396-R2-1 | SEQ ID NO: 15<br>QVQLVESGGGVVQPGGSLRLSCAASGLTLSQYTMGWFRQAPGKERELVAAIHWTSSVTDYADSVYGRFTISRDDSKNTGYLQMNSLRAEDTAVYYCAATWYYTHRGSFDYWGQGTLVTVSS |
| W3396-R2-2 | SEQ ID NO: 17<br>QVQLVESGGGVVQPGGSLRLSCAASGLTLSCQYTMGWFRQAPGKERELVAAIHWTSSVTDYADSVYGRFTISRDDSKNTGYLQMNSLRAEDTAVYYCAATHYYTHRGPFDYWGQGTLVTVSS |
| W3396-R2-3 | SEQ ID NO: 19<br>QVQLVESGGGVVQPGGSLRLSCAASGLTLSQYTMGWFRQAPGKERELVAAIHWTSSVTDYADSVYGRFTISRDDSKNTGYLQMNSLRAEDTAVYYCAATWYYTHRGPFDYWGQGTLVTVSS |
| W3396-R2-6 | SEQ ID NO: 21<br>QVQLVESGGGVVQPGGSLRLSCAASGLTLSQYTMGWFRQAPGKERELVAAIHWTSSVTDYADSVMGRFTISRDDSKNTGYLQMNSLRAEDTAVYYCAATWYYTHRGPFDYWGQGTLVTVSS |
| W3396-R2-10 | SEQ ID NO: 23<br>QVQLVESGGGVVQPGGSLRLSCAASGLTLSQYTMGWFRQAPGKERELVAAIHWTSSVTDYADSVDGRFTISRDDSKNTGYLQMNSLRAEDTAVYYCAATWYYTHRGSFDYWGQGTLVTVSS |
| W3396-R2-11 | SEQ ID NO: 25<br>QVQLVESGGGVVQPGGSLRLSCAASGLTLSQYTMGWFRQAPGKERELVAAIHWTSSVTDYADSVDGRFTISRDDSKNTGYLQMNSLRAEDTAVYYCAATHYYTHRGPFDYWGQGTLVTVSS |
| W3396-R2-12 | SEQ ID NO: 27<br>QVQLVESGGGVVQPGGSLRLSCAASGLTLSQYTMGWFRQAPGKERELVAAIHWTSSVTDYADSVDGRFTISRDDSKNTGYLQMNSLRAEDTAVYYCAATWYYTHRGPFDYWGQGTLVTVSS |
| W3396-R2-13 | SEQ ID NO: 29<br>QVQLVESGGGVVQPGGSLRLSCAASGLTLSQYTMGWFRQAPGKERELVAAIHWTSSVTDYADSVRGRFTISRDDSKNTGYLQMNSLRAEDTAVYYCAATWYYTHRGSFDYWGQGTLVTVSS |

TABLE 2-continued

Variable region amino acid sequences

VH

W3396-R1-26H2  SEQ ID NO: 31
QVQLVESGGGVVQPGGSLRLSCAASGLTLSQYTMGWFR
QAPGKERELVAAIHWTSSVTDYADSVYGRFTISRDDSKN
TGYLQMNSLRAEDTAVYYCAATHYYTHRGSFDYWGQG
TLVTVSS

TABLE 3

Variable region nucleotide sequences

VHnu

W3396-parent  SEQ ID NO: 12
caggtgcagctggtggagtccggggaggattggtgcaggctgggggctcactgagact
ctcctgtgcagcctctggactgaccttgagtcaatataccatgggctggttccgccaggctcc
agggaaggagcgtgagttggtagcagctattcattggactagtagtgtcaccgactatgcag
actccgtgaaggccgattcaccatctccagagacgacgccaggaacacgggctatctgc
aaatgaacagcctgaaatttgaggacacggccgtttattactgtgcagccacacactactac
acccacagaggaagcttcgactactggggccaggggacccaggtcaccgtctcctca W3396-Z4  SEQ ID NO: 14
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtgaaaggccgctttaccattagccgcgatgatagcaaaaatactggttatctgca
gatgaattctttacgcgccgaagataccgccgtgtattactgcgccgccacccattactatac
ccatcgcggagctttgattactggggtcaaggtacttagtgaccgtgagcagc W3396-R2-1  SEQ ID NO: 16
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtgtacggccgctttaccattagccgcgatgatagcaaaaatactggttatctgca
gatgaattctttacgcgccgaagataccgccgtgtattactgcgccgccacctggtactatac
ccatcgcggcagctttgattactggggtcaaggtacttagtgaccgtgagcagc W3396-R2-2  SEQ ID NO: 18
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtgtacggccgctttaccattagccgcgatgatagcaaaaatactggttatctgca
gatgaattctttacgcgccgaagataccgccgtgtattactgcgccgccaccattactatac
ccatcgcggccctttgattactggggtcaaggtacttagtgaccgtgagcagc W3396-R2-3  SEQ ID NO: 20
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtgtacggccgctttaccattagccgcgatgatagcaaaaatactggttatctgca
gatgaattctttacgcgccgaagataccgccgtgtattactgcgccgccacctggtactatac
ccatcgcggccctttgattactggggtcaaggtacttagtgaccgtgagcagc W3396-R2-6  SEQ ID NO: 22
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtgatgggccgctttaccattagccgcgatgatagcaaaaatactggttatctgca
gatgaattctttacgcgccgaagataccgccgtgtattactgcgccgccacctggtactatac
ccatcgcggccctttgattactggggtcaaggtacttagtgaccgtgagcagc W3396-R2-10  SEQ ID NO: 24
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtggacggccgctttaccattagccgcgatgatagcaaaaatactggttatctgca
gatgaattctttacgcgccgaagataccgccgtgtattactgcgccgccacctggtactatac
ccatcgcggcagctttgattactggggtcaaggtacttagtgaccgtgagcagc TABLE 3-continued Variable region nucleotide sequences VHnu W3396-R2-11  SEQ ID NO: 26
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtggacggccgctttaccattagccgcgatgatagcaaaaatactggttatctgca
gatgaattctttacgcgccgaagataccgccgtgtattactgcgccgccacccattactatac
ccatcgcggccctttgattactggggtcaaggtactttagtgaccgtgagcagc W3396-R2-12  SEQ ID NO: 28
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtggacggccgctttaccattagccgcgatgatagcaaaaatactggttatctgca
gatgaattctttacgcgccgaagataccgccgtgtattactgcgccgccacctggtactatac
ccatcgcggccctttgattactggggtcaaggtactttagtgaccgtgagcagc W3396-R2-13  SEQ ID NO: 30
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtgcggggccgctttaccattagccgcgatgatagcaaaaatactggttatctgca
gatgaattctttacgcgccgaagataccgccgtgtattactgcgccgccacctggtactatac
ccatcgcggcagctttgattactggggtcaaggtactttagtgaccgtgagcagc W3396-R1-26H2  SEQ ID NO: 32
caagttcagctggtggaaagcggcggtggtgttgttcagccgggtggcagtctgcgtctga
gctgcgcagccagtggtctgactttaagccagtataccatgggttggtttcgccaagctccg
ggtaaagaacgcgaactggtggccgccattcattggaccagcagcgtgaccgattatgcc
gatagcgtgtacggccgctttaccattagccgcgatgatagcaaaaatactggttatctgcag
atgaattctttacgcgccgaagataccgccgtgtattactgcgccgccacccattactatacc
catcgcggcagctttgattactggggtcaaggtactttagtgaccgtgagcagc In certain embodiments, the antibody polypeptides provided herein are single domain antibodies.

In certain embodiments, the heavy chain variable domain of the antibody polypeptides provided herein is derived from a VHH domain. VHH domains are heavy chain variable domains derived from antibodies naturally devoid of light chains, for example, antibodies derived from Camelidae species (see, e.g. WO9404678), for example in camel, llama, dromedary, alpaca and guanaco. VHH domains are single polypeptides, and are stable.

In certain embodiments, the heavy chain variable domain of the antibody polypeptides provided herein is of camelid origin.

CDRs are known to be responsible for antigen binding, however, it has been found that not all of the 6 CDRs are indispensable or unchangeable. In other words, it is possible to replace or change or modify one or more CDRs in anti-LAG-3 single domain antibody W3396-parent, W3396-Z4, W3396-R2-1, W3396-R2-2, W3396-R2-3, W3396-R2-6, W3396-R2-10, W3396-R2-11, W3396-R2-12, W3396-R2-13, or W3396-R1-26H2, yet substantially retain the specific binding affinity to LAG-3.

In certain embodiments, the anti-LAG-3 antibody polypeptides provided herein comprise a heavy chain CDR3 sequence of one of the anti-LAG-3 single domain antibodies W3396-parent, W3396-Z4, W3396-R2-1, W3396-R2-2, W3396-R2-3, W3396-R2-6, W3396-R2-10, W3396-R2-11, W3396-R2-12, W3396-R2-13, or W3396-R1-26H2. In certain embodiments, the anti-LAG-3 antibody polypeptides provided herein comprise a heavy chain CDR3 sequence selected from the group consisting of SEQ ID NOs: 3, 5, 6, and 7. Heavy chain CDR3 regions are located at the center of the antigen-binding site, and therefore are believed to make the most contact with antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Nature. 302:575-81). The diversity in the heavy chain CDR3 is sufficient to produce most antibody specificities (Xu J L, Davis M M. Immunity. 13:37-45) as well as desirable antigen-binding affinity (Schier R, etc. J Mol Biol. 263:551-67).

In certain embodiments, the antibody polypeptides provided herein comprise suitable framework region (FR) sequences, as long as the antibody polypeptides can specifically bind to LAG-3. The CDR sequences provided in Table 1 are obtained from camelid antibodies, but they can be grafted to any suitable FR sequences of any suitable species such as mouse, human, rat, rabbit, among others, using suitable methods known in the art such as recombinant techniques.

In certain embodiments, the antibody polypeptides provided herein are humanized. A humanized antibody polypeptide is desirable in its reduced immunogenicity in human. A humanized antibody polypeptide is chimeric in its variable regions, as non-human CDR sequences are grafted to human or substantially human FR sequences. Humanization of an antibody polypeptide can be essentially performed by substituting the non-human (such as murine) CDR genes for the corresponding human CDR genes in a human immunoglobulin gene (see, for example, Jones et al. (1986) Nature 321:522-525; Riechmann et al. (1988) Nature 332:323-327; Verhoeyen et al. (1988) Science 239:1534-1536).

Suitable human heavy chain variable domains can be selected to achieve this purpose using methods known in the art. In an illustrative example, "best-fit" approach can be used, where a non-human (e.g. camelid) antibody variable domain sequence is screened or BLASTed against a database of known human variable domain sequences, and the human sequence closest to the non-human query sequence is identified and used as the human scaffold for grafting the non-human CDR sequences (see, for example, Sims et al, (1993) J. Immunol. 151:2296; Chothia et al. (1987) J. Mot. Biol. 196:901). Alternatively, a framework derived from the consensus sequence of all human antibodies may be used for the grafting of the non-human CDRs (see, for example, Carter et at. (1992) Proc. Natl. Acad. Sci. USA, 89:4285; Presta et al. (1993) J. Immunol., 151:2623).

In certain embodiments, the humanized antibody polypeptides provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived different human immunoglobulin genes, for example, FR sequences derived from one human antibody and constant region from another human antibody. In some embodiments, the humanized antibody polypeptide comprise human FR1-4.

In certain embodiments, the humanized antibody polypeptides provided herein comprise one or more FR sequences of W3396-Z4, W3396-R2-1, W3396-R2-2, W3396-R2-3, W3396-R2-6, W3396-R2-10, W3396-R2-11, W3396-R2-12, W3396-R2-13, or W3396-R1-26H2.

The 10 exemplary humanized anti-LAG-3 single domain antibodies W3396-Z4, W3396-R2-1, W3396-R2-2, W3396-R2-3, W3396-R2-6, W3396-R2-10, W3396-R2-11, W3396-R2-12, W3396-R2-13, or W3396-R1-26H2 all retained the specific binding affinity to LAG-3, and are at least comparable to, or even better than, the parent camelid antibodies in that aspect.

In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody polypeptides closely approximate the non-human parent antibody structure. In certain embodiments, the humanized antibody polypeptides provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FRs of a heavy or a light chain variable domain. In some embodiments, such change in amino acid residue could be present in heavy chain FR regions only, in light chain FR regions only, or in both chains.

In certain embodiments, the antibody polypeptides provided herein comprise a heavy chain variable domain sequence selected from the group consisting of SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31.

In some embodiments, the anti-LAG-3 antibody polypeptides provided herein comprise all or a portion of the heavy chain variable domain. In one embodiment, the anti-LAG-3 antibody polypeptides provided herein is a single domain antibody which consists of all or a portion of the heavy chain variable domain provided herein. More information of such a single domain antibody is available in the art (see, e.g., U.S. Pat. No. 6,248,516).

In certain embodiments, the anti-LAG-3 antibody polypeptides provided herein further comprise an immunoglobulin constant region. In some embodiments, an immunoglobulin constant region comprises a heavy chain. The heavy chain constant region comprises CH1, hinge, and/or CH2-CH3 regions. In certain embodiments, the heavy chain constant region comprises an Fc region. In certain embodiments, the heavy chain constant region comprises or is a CH2-CH3 region.

In some embodiments, the anti-LAG-3 antibody polypeptide provided herein have a constant region of an immunoglobulin (Ig), optionally a human Ig, optionally a human IgG. In certain embodiments, the anti-LAG-3 antibody polypeptide provided herein comprises a constant region of IgG1 isotype, which could induce ADCC or CDC, or a constant region of IgG4 or IgG2 isotype, which has reduced or depleted effector function. Effector functions such as ADCC and CDC can lead to cytotoxicity to cells expressing LAG-3. Effector functions can be evaluated using various assays such as Fc receptor binding assay, C1q binding assay, and cell lysis assay.

Binding affinity of the antibody polypeptide provided herein can be represented by $K_D$ value, which represents the ratio of dissociation rate to association rate ($k_{off}/k_{on}$) when the binding between the antigen and antigen-binding molecule reaches equilibrium. The antigen-binding affinity (e.g. $K_D$) can be appropriately determined using suitable methods known in the art, including, for example, flow cytometry assay. In some embodiments, binding of the antibody polypeptide to the antigen at different concentrations can be determined by flow cytometry, the determined mean fluorescence intensity (MFI) can be firstly plotted against antibody concentration, $K_D$ value can then be calculated by fitting the dependence of specific binding fluorescence intensity (Y) and the concentration of antibodies (X) into the one site saturation equation: $Y=B_{max}*X/(K_D+X)$ using Prism version 5 (GraphPad Software, San Diego, Calif.), wherein $B_{max}$ refers to the maximum specific binding of the tested antibody polypeptide to the antigen.

In some embodiments, the anti-LAG-3 antibody polypeptides provided herein are capable of specifically binding to human LAG-3 with a binding affinity ($K_D$) of no more than $5\times10^{-9}$M, no more than $4\times10^{-9}$M, no more than $3\times10^{-9}$M, no more than $2\times10^{-9}$M, no more than $10^{-9}$M, no more than $5\times10^{-10}$M, no more than $4\times10^{-10}$M, no more than $3\times10^{-10}$ M, no more than $2\times10^{-10}$M, no more than $10^{-10}$M, no more than $5\times10^{-11}$ M, or no more than $4\times10^{-11}$ M, no more than $3\times10^{-11}$ M, no more than $2.5\times10^{-11}$ M, no more than $2\times10^{-11}$ M, no more than $10^{-11}$ M, no more than $5\times10^{-12}$ M, no more than $4\times10^{-12}$ M, no more than $3\times10^{-12}$ M, no more than $2.5\times10^{-12}$ M, no more than $2\times10^{-12}$ M, or no more than $10^{-12}$ M, as measured by surface plasmon resonance (SPR) or by flow cytometry.

In certain embodiments, the anti-LAG-3 antibody polypeptides provided herein cross-react with cynomolgus monkey LAG-3, and mouse LAG-3. In certain embodiments, the antibody polypeptides provided herein bind to cynomolgus monkey or mouse LAG-3 with a binding affinity similar to that of human LAG-3.

In some embodiments, the anti-LAG-3 antibody polypeptides provided herein are capable of specifically binding to cynomolgus monkey LAG-3 with a binding affinity ($K_D$) of no more than $5\times10^{-9}$M, no more than $4\times10^{-9}$M, no more than $3\times10^{-9}$M, no more than $2\times10^{-9}$M, no more than $10^{-9}$M, no more than $5\times10^{-10}$M, no more than $4\times10^{-10}$ M, no more than $3\times10^{-10}$M, no more than $2\times10^{-10}$M, no more than $10^{-10}$M, no more than $5\times10^{-11}$ M, or no more than $4\times10^{-11}$ M, no more than $3\times10^{-11}$ M, no more than $2.5\times10^{-11}$ M, no more than $2\times10^{-11}$ M, no more than $10^{-11}$ M, no more than $5\times10^{-12}$ M, no more than $4\times10^{-12}$ M, no more than $3\times10^{-12}$ M, no more than $2.5\times10^{-12}$ M, no more than $2\times10^{-12}$ M, or no more than $10^{-12}$ M, as measured by surface plasmon resonance (SPR) or by flow cytometry.

In some embodiments, the anti-LAG-3 antibody polypeptides provided herein are capable of specifically binding to mouse LAG-3 with a binding affinity ($K_D$) of no more than $5\times10^{-9}$M, no more than $4\times10^{-9}$M, no more than $3\times10^{-9}$M, no more than $2\times10^{-9}$M, no more than $10^{-9}$M, no more than $5\times10^{-10}$M, no more than $4\times10^{-10}$M, no more than $3\times10^{-10}$M, no more than $2\times10^{-10}$M, no more than $10^{-10}$M, no more than $5\times10^{-11}$ M, or no more than $4\times10^{-11}$ M, no more than $3\times10^{-11}$ M, no more than $2.5\times10^{-11}$ M, no more than $2\times10^{-11}$ M, no more than $10^{-11}$ M, no more than $5\times10^{-12}$ M, no more than $4\times10^{-12}$ M, no more than $3\times10^{-12}$ M, no more than $2.5\times10^{-12}$ M, no more than $2\times10^{-12}$ M, or no more than $10^{-12}$ M, no more than $5\times10^{-13}$ M, no more than $4\times10^{-13}$ M, no more than $3\times10^{-13}$ M, no more than $2.5\times10^{-13}$ M, no more than $2\times10^{-13}$ M, or no more than $10^{-13}$ M, as measured by surface plasmon resonance (SPR) or by flow cytometry.

Binding of the antibody polypeptides to human LAG-3 can also be represented by "half maximal effective concentration" ($EC_{50}$) value, which refers to the concentration of an antibody where 50% of its maximal effect (e.g., binding or inhibition etc.) is observed. The $EC_{50}$ value can be measured by methods known in the art, for example, sandwich assay such as ELISA, Western Blot, flow cytometry assay, and other binding assay. In certain embodiments, the antibody polypeptides provided herein specifically bind to human LAG-3 at an $EC_{50}$ of no more than 0.1 nM, no more than 0.2 nM, no more than 0.25 nM, no more than 0.3 nM, no more than 0.4 nM, no more than 0.5 nM, no more than 1 nM, no more than 1.5 nM, no more than 3 nM, or no more than 5 nM, or no more than 10 nM, no more than 20 nM by flow cytometry.

In certain embodiments, the antibody polypeptides bind to Cynomolgus monkey or mouse LAG-3 with a binding affinity similar to that of human LAG-3. For example, binding of the exemplary single domain antibodies W3396-Z4, W3396-R2-1, W3396-R2-2, W3396-R2-3, W3396-R2-6, W3396-R2-10, W3396-R2-11, W3396-R2-12, W3396-R2-13, or W3396-R1-26H2 to cynomolgus monkey or mouse LAG-3 is at a similar affinity or $EC_{50}$ value to that of human LAG-3.

In certain embodiments, the antibody polypeptides provided herein specifically bind to recombinant cynomolgus monkey LAG-3 with an $EC_{50}$ of no more than 0.1 nM, no more than 0.2 nM, no more than 0.3 nM, no more than 0.5 nM, no more than 1 nM, no more than 1.5 nM, no more than 2 nM, no more than 2.5 nM, no more than 3 nM, no more than 3.5 nM, no more than 4 nM or no more than 4.5 nM by flow cytometry.

In certain embodiments, the antibody polypeptides provided herein specifically bind to recombinant mouse LAG-3 with an $EC_{50}$ of no more than 0.01 nM, no more than 0.05 nM, no more than 0.1 nM, no more than 0.15 nM, no more than 0.2 nM, no more than 0.3 nM, no more than 0.4 nM, no more than 0.5 nM, no more than 0.6 nM, no more than 0.7 nM, no more than 0.8 nM, no more than 0.9 nM, or no more than 1 nM by flow cytometry.

In certain embodiments, the antibody polypeptides provided herein have a specific binding affinity to human LAG-3 which is sufficient to provide for diagnostic and/or therapeutic use.

In certain embodiments, the antibody polypeptides provided herein block binding of human LAG-3 to its ligands and therefore restore activities of effector cells, diminish suppressor activity of Tregs, and/or enhance anti-tumor activity. Ligands for LAG-3 includes, e.g. MHC-II, LSECtin and Galectin-3. LSECtin is a type II transmembrane protein, with a C-terminal C-type carbohydrate-recognition domain (CRD) projected from the membrane surface by an intermediate neck domain. The receptor appears to be a disulfide-linked dimer and serves as a model for other members of the C-type lectin family that are expressed on sinusoidal endothelial cells and facilitate viral infection, but lack endocytic function. Galectin-3 is a protein that in humans is encoded by the LGALS3 gene. Galectin-3 is a member of the lectin family, of which 14 mammalian galectins have been identified. Galectin-3 (Gal-3) is also a member of the beta-galactoside-binding protein family that plays an important role in cell adhesion, cell activation and chemoattraction, cell growth and differentiation, cell cycle, and apoptosis. Given galectin-3's broad biological functionality, it has been demonstrated to be involved in cancer, inflammation and fibrosis, heart disease, and stroke. Studies have also shown that the expression of galectin-3 is implicated in a variety of processes associated with heart failure, including myofibroblast proliferation, fibrogenesis, tissue repair, inflammation, and ventricular remodelings. The blocking of binding of LAG-3 to MHC-II, LSECtin and Galectin-3 can be determined using methods known in the art, for example, by ELISA.

The antibody polypeptides provided herein can be monoclonal, humanized, chimeric, recombinant, labeled, bivalent, or anti-idiotypic. A recombinant antibody polypeptide is an antibody polypeptide prepared in vitro using recombinant methods rather than in animals.

Antibody Variants

The antibody polypeptides provided herein also encompass various variants thereof. In certain embodiments, the antibody polypeptides encompasses various types of variants of an exemplary antibody provided herein, i.e., W3396-parent, W3396-Z4, W3396-R2-1, W3396-R2-2, W3396-R2-3, W3396-R2-6, W3396-R2-10, W3396-R2-11, W3396-R2-12, W3396-R2-13, or W3396-R1-26H2.

In certain embodiments, the antibody polypeptide variants comprise one or more modifications or substitutions in one or more CDR sequences as provided in Table 1, one or more variable region sequences (but not in any of the CDR sequences) provided in Table 2, and/or the constant region (e.g. Fc region). Such variants retain specific binding affinity to LAG-3 of their parent antibodies, but have one or more desirable properties conferred by the modification(s) or substitution(s). For example, the antibody polypeptide variants may have improved antigen-binding affinity, improved productivity, improved stability, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation (e.g. one or more introduced cysteine residues).

The parent antibody sequence may be screened to identify suitable or preferred residues to be modified or substituted, using methods known in the art, for example "alanine scanning mutagenesis" (see, for example, Cunningham and Wells (1989) Science, 244:1081-1085). Briefly, target residues (e.g., charged residues such as Arg, Asp, His, Lys, and Glu) can be identified and replaced by a neutral or negatively charged amino acid (e.g., alanine or polyalanine), and the modified antibody polypeptides are produced and screened for the interested property. If substitution at a particular amino acid location demonstrates an interested functional change, then the position can be identified as a potential residue for modification or substitution. The potential residues may be further assessed by substituting with a different type of residue (e.g. cysteine residue, positively charged residue, etc.).

Affinity Variant

Affinity variant may contain modifications or substitutions in one or more CDR sequences as provided in Table 1, one or more FR sequences, or the heavy chain variable region sequences provided in Table 2. FR sequences can be readily identified by a skilled person in the art based on the CDR sequences in Table 1 and variable region sequences in Table 2, as it is well-known in the art that a CDR region is flanked by two FR regions in the variable region. The affinity variants retain specific binding affinity to LAG-3 of the parent antibody, or even have improved LAG-3 specific binding affinity over the parent antibody. In certain embodiments, at least one (or all) of the substitution(s) in the CDR sequences, FR sequences, or variable region sequences comprises a conservative substitution.

A skilled artisan will understand that in the CDR sequences and variable region sequences provided in Table 1 and Table 2, one or more amino acid residues may be substituted yet the resulting antibody polypeptide still retain the binding affinity to LAG-3, or even have an improved binding affinity. Various methods known in the art can be used to achieve this purpose. For example, a library of antibody variants (such as Fab or scFv variants) can be generated and expressed with phage display technology, and then screened for the binding affinity to human LAG-3. For another example, computer software can be used to virtually simulate the binding of the antibodies to human LAG-3, and identify the amino acid residues on the antibodies which form the binding interface. Such residues may be either avoided in the substitution so as to prevent reduction in binding affinity, or targeted for substitution to provide for a stronger binding.

In certain embodiments, the humanized antibody polypeptides provided herein comprise one or more amino acid residue substitutions in one or more CDR sequences, and/or one or more FR sequences. In certain embodiments, an affinity variant comprises no more than 10, 9, 8, 7, 6, 5, 4, 3, 2, or 1 substitutions in the CDR sequences and/or FR sequences in total.

In certain embodiments, the anti-LAG-3 antibody polypeptides comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to LAG-3 at a level similar to or even higher than its parent antibody.

In certain embodiments, the anti-LAG-3 antibody polypeptides comprise one or more variable region sequences having at least 80% (e.g. at least 85%, 88%, 90%, 91%, 92%, 93%, 94%, 95%, 96%, 97%, 98%, 99%) sequence identity to that (or those) listed in Table 2, and in the meantime retain the binding affinity to LAG-3 at a level similar to or even higher than its parent antibody. In some embodiments, a total of 1 to 10 amino acids have been substituted, inserted, or deleted in a variable region sequence listed in Table 2. In some embodiments, the substitutions, insertions, or deletions occur in regions outside the CDRs (e.g., in the FRs).

Glycosylation Variant

The anti-LAG-3 antibody polypeptides provided herein also encompass a glycosylation variant, which can be obtained to either increase or decrease the extent of glycosylation of the antibody polypeptide.

The antibody polypeptide may comprise one or more amino acid residues with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

Cysteine-Engineered Variant

The anti-LAG-3 antibody polypeptides provided herein also encompass a cysteine-engineered variant, which comprises one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibody polypeptides to introduce free cysteine residues are known in the art, see, for example, WO2006/034488.

Fc Variant

The anti-LAG-3 antibody polypeptides provided herein also encompass an Fc variant, which comprises one or more amino acid residue modifications or substitutions at its Fc region and/or hinge region.

In certain embodiments, the anti-LAG-3 antibody polypeptides comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the lysosome and then be translocated and released out of the cell. Methods of engineering an antibody polypeptide to improve binding affinity with FcRn are well-known in the art, see, for example, Vaughn, D. et al, Structure, 6(1): 63-73, 1998; Kontermann, R. et al, Antibody Engineering, Volume 1, Chapter 27: Engineering of the Fc region for improved PK, published by Springer, 2010; Yeung, Y. et al, Cancer Research, 70: 3269-3277 (2010); and Hinton, P. et al, J. Immunology, 176:346-356 (2006).

In certain embodiments, the anti-LAG-3 antibody polypeptides comprise one or more amino acid substitution(s) that alters the antibody-dependent cellular cytotoxicity (ADCC). Certain amino acid residues at CH2 domain of the Fc region can be substituted to provide for enhanced ADCC activity. Alternatively or additionally, carbohydrate structures on the antibody can be changed to enhance ADCC activity. Methods of altering ADCC activity by antibody engineering have been described in the art, see for example, Shields R L. et al., J Biol Chem. 2001. 276(9): 6591-604;

Idusogie E E. et al., J Immunol. 2000.164(8):4178-84; Steurer W. et al., J Immunol. 1995, 155(3): 1165-74; Idusogie E E. et al., J Immunol. 2001, 166(4): 2571-5; Lazar G A. et al., PNAS, 2006, 103(11): 4005-4010; Ryan M C. et al., Mol. Cancer Ther., 2007, 6: 3009-3018; Richards J O, et al., Mol Cancer Ther. 2008, 7(8): 2517-27; Shields R. L. et al, J. Biol. Chem, 2002, 277: 26733-26740; Shinkawa T. et al, J. Biol. Chem, 2003, 278: 3466-3473. In certain embodiments, the anti-LAG-3 antibody polypeptides comprise a human IgG4 constant region in which the $228^{th}$ amino acid residue is altered, for example from Ser228Pro (S228P, which may prevent or reduce strand exchange), and/or the $235^{th}$ amino acid residue is altered, for example from Leu235Glu (L235E, which may alter Fc receptor interactions.

In certain embodiments, the anti-LAG-3 antibody polypeptides comprise one or more amino acid substitution(s) that alters Complement Dependent Cytotoxicity (CDC), for example, by improving or diminishing C1q binding and/or CDC (see, for example, WO99/51642; Duncan& Winter Nature 322:738-40 (1988); U.S. Pat. Nos. 5,648,260; 5,624, 821); and WO94/29351 concerning other examples of Fc region variants.

In certain embodiments, the anti-LAG-3 antibody polypeptides comprise one or more amino acid substitution(s) in the interface of the Fc region to facilitate and/or promote heterodimerization. These modifications comprise introduction of a protuberance into a first Fc polypeptide and a cavity into a second Fc polypeptide, wherein the protuberance can be positioned in the cavity so as to promote interaction of the first and second Fc polypeptides to form a heterodimer or a complex. Methods of generating antibodies with these modifications are known in the art, e.g., as described in U.S. Pat. No. 5,731,168.

Various techniques can be used for the production of VHH or single domain antibodies. For example, VHHs may be obtained using methods known in the art such as by immunising a camel and obtaining hybridoma's therefrom, or by cloning a library of single domain antibodies using molecular biology techniques known in the art and subsequent selection by using phage display.

In another aspect of the present disclosure, an antibody polypeptide provided herein may comprise two or more single domain antibodies which have been joined. The single domain antibodies may be identical in sequence and directed against the same target or antigen. Depending on the number of VHHs linked, the antibody polypeptide may be bivalent (2 VHHs), trivalent (3 VHHs), tetravalent (4 VHHs) or have a higher valency molecules.

Conjugates

In some embodiments, the anti-LAG-3 antibody polypeptides further comprise a conjugate moiety. The conjugate moiety can be linked to the antibody polypeptides. A conjugate moiety is a non-proteinaceous moiety that can be attached to the antibody polypeptide. It is contemplated that a variety of conjugate moieties may be linked to the antibody polypeptides provided herein (see, for example, "Conjugate Vaccines", Contributions to Microbiology and Immunology, J. M. Cruse and R. E. Lewis, Jr. (eds.), Carger Press, New York, (1989)). These conjugate moieties may be linked to the antibody polypeptides by covalent binding, affinity binding, intercalation, coordinate binding, complexation, association, blending, or addition, among other methods.

In certain embodiments, the antibody polypeptides disclosed herein may be engineered to contain specific sites outside the epitope binding portion that may be utilized for binding to one or more conjugate moieties. For example, such a site may include one or more reactive amino acid residues, such as for example cysteine or histidine residues, to facilitate covalent linkage to a conjugate moiety.

In certain embodiments, the antibodies may be linked to a conjugate moiety indirectly, or through another conjugate moiety. For example, the antibody polypeptides may be conjugated to biotin, then indirectly conjugated to a second conjugate that is conjugated to avidin. The conjugate can be a clearance-modifying agent, a toxin (e.g., a chemotherapeutic agent), a detectable label (e.g., a radioactive isotope, a lanthanide, a luminescent label, a fluorescent label, or an enzyme-substrate label), or purification moiety.

A "toxin" can be any agent that is detrimental to cells or that can damage or kill cells. Examples of toxin include, without limitation, taxol, cytochalasin B, gramicidin D, ethidium bromide, emetine, mitomycin, etoposide, tenoposide, vincristine, MMAE, MMAF, DM1, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), a topoisomerase inhibitor, and a tubulin-binders.

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$, $^{124}$I, $^{125}$I, $^{131}$I, $^{35}$S, $^{3}$H, $^{111}$In, $^{12}$n, $^{14}$C, $^{64}$Cu, $^{67}$Cu, $^{86}$Y $^{88}$Y $^{90}$Y, $^{177}$Lu, $^{211}$At, $^{186}$Re, $^{188}$Re, $^{153}$Sm, $^{212}$Bi, and $^{32}$P, other lanthanides), luminescent labels, chromophoric moiety, digoxigenin, biotin/avidin, a DNA molecule or gold for detection.

In certain embodiments, the conjugate moiety can be a clearance-modifying agent which helps increase half-life of the antibody. Illustrative example include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymer are attached, they can be the same or different molecules.

In certain embodiments, the conjugate moiety can be a purification moiety such as a magnetic bead.

In certain embodiments, the antibody polypeptides provided herein is used for a base for a conjugate.

Polynucleotides and Recombinant Methods

The present disclosure provides isolated polynucleotides that encode the anti-LAG-3 antibody polypeptides.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

In certain embodiments, the isolated polynucleotides comprise one or more nucleotide sequences as shown in SEQ IN NO: 12, 14, 16, 18, 20, 22, 24, 26, 28, 30, and/or 32, and/or a homologous sequence thereof having at least 80% (e.g. at least 85%, 88%, 90%, 92%, 93%, 94%, 95%, 96%, 97%, 98%, or 99%) sequence identity, and/or a variant thereof having only degenerate substitutions, and encodes the variable region of the exemplary antibodies provided herein. DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

The isolated polynucleotide that encodes the anti-LAG-3 antibody polypeptides (e.g. including the sequences as shown in Table 3) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-la), and a transcription termination sequence.

The present disclosure provides vectors (e.g., expression vectors) containing the nucleic acid sequence provided herein encoding the antibody polypeptides, at least one promoter (e.g., SV40, CMV, EF-la) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pProl8, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody polypeptide can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for expressing anti-LAG-3 antibody polypeptides. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some preferable embodiments, the host cell is 293F cell.

Host cells are transformed with the above-described expression or cloning vectors for anti-LAG-3 antibody polypeptide production and cultured in conventional nutrient media modified as appropriate for inducing promoters, selecting transformants, or amplifying the genes encoding the desired sequences. In another embodiment, the antibody polypeptides may be produced by homologous recombination known in the art.

The host cells used to produce the antibody polypeptides provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody polypeptides can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-LAG-3 antibody polypeptides prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody polypeptide. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., *J. Immunol. Meth.* 62:1-13 (1983)). Protein G is recommended for all mouse isotypes and for human gamma3 (Guss et al., *EMBO J.* 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Composition

The present disclosure further provides pharmaceutical compositions comprising an anti-LAG-3 antibody polypeptide and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody polypeptide and conjugates as provided herein decreases oxidation of the antibody polypeptide. This reduction in oxidation prevents or reduces loss of binding affinity, thereby improving antibody stability and maximizing shelf-life. Therefore, in certain embodiments compositions are provided that comprise one or more antibody polypeptides as disclosed herein and one or more antioxidants such as methionine. Further provided are methods for preventing oxidation of, extending the shelf-life of, and/or improving the efficacy of an antibody polypeptide as provided herein by mixing the antibody polypeptide with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody polypeptide as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-LAG-3 antibody polypeptides or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Methods of Use

The present disclosure also provides therapeutic methods comprising: administering a therapeutically effective amount of the antibody polypeptides as provided herein to a subject in need thereof, thereby treating or preventing a LAG-3-related condition or a disorder. In some embodiments, the LAG-3-related condition or a disorder is cancer, autoimmune disease, or infectious disease.

Examples of cancer include but are not limited to, lymphoma, bladder cancer, bone cancer, brain and central nervous system cancer, breast cancer, uterine or endometrial cancer, rectal cancer, esophageal cancer, head and neck cancer, anal cancer, gastrointestinal cancer, intra-epithelial neoplasm, kidney or renal cancer, leukemia, liver cancer, lung cancer (e.g. non-small cell lung cancer and small cell lung cancer), melanoma, myeloma, pancreatic cancer, prostate cancer, sarcoma, skin cancer, squamous cell cancer, stomach cancer, testicular cancer, vulval cancer, cancer of the endocrine system, cancer of the parathyroid gland, cancer of the adrenal gland, penile carcinoma, solid tumors of childhood, tumor angiogenesis, spinal axis tumor, pituitary adenoma, or epidermoid cancer.

Examples of autoimmune diseases include, but are not limited to, Acquired Immunodeficiency Syndrome (ADS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Examples of infectious disease include, but are not limited to, fungus infection, parasite/protozoan infection or chronic viral infection, for example, malaria, coccidioiodmycosis immitis, histoplasmosis, onychomycosis, aspergilosis, blastomycosis, candidiasis albicans, paracoccidioiomycosis, microsporidiosis, *Acanthamoeba keratitis*, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, Trichuriasis, Trypanosomiasis, helminth infection, infection of hepatitis B (HBV), hepatitis C (HCV), herpes virus, Epstein-Barr virus, HIV, cytomegalovirus, herpes simplex virus type I, herpes simplex virus type II, human papilloma virus, adenovirus, human immunodeficiency virus I, human immunodeficiency virus II, Kaposi West sarcoma associated herpes virus epidemics, thin ring virus (Torquetenovirus), human T lymphotrophic viruse I, human T lymphotrophic viruse II, varicella zoster, JC virus or BK virus.

The therapeutically effective amount of an antibody polypeptide as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, the antibody polypeptides as provided herein may be administered at a therapeutically effective dosage of about 0.01 mg/kg to about 100 mg/kg. In certain of these embodiments, the antibody polypeptide is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibody polypeptides disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In some embodiments, the antibody polypeptides disclosed herein may be administered alone or in combination with one or more additional therapeutic means or agents. For example, the antibody polypeptides disclosed herein may be administered in combination with another therapeutic agent, for example, a chemotherapeutic agent or an anti-cancer drug.

In certain of these embodiments, an antibody polypeptide as disclosed herein that is administered in combination with one or more additional therapeutic agents may be administered simultaneously with the one or more additional therapeutic agents, and in certain of these embodiments the antibody polypeptide and the additional therapeutic agent(s) may be administered as part of the same pharmaceutical composition. However, an antibody polypeptide administered "in combination" with another therapeutic agent does not have to be administered simultaneously with or in the same composition as the agent. An antibody polypeptide administered prior to or after another agent is considered to be administered "in combination" with that agent as the phrase is used herein, even if the antibody polypeptide and second agent are administered via different routes. Where possible, additional therapeutic agents administered in combination with the antibody polypeptides disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The present disclosure further provides methods of using the anti-LAG-3 antibody polypeptides.

In some embodiments, the present disclosure provides methods of detecting presence or amount of LAG-3 in a sample, comprising contacting the sample with the antibody polypeptide, and determining the presence or the amount of LAG-3 in the sample.

In some embodiments, the present disclosure provides methods of diagnosing a LAG-3 related disease or condition in a subject, comprising: a) contacting a sample obtained from the subject with the antibody polypeptide provided herein; b) determining presence or amount of LAG-3 in the sample; and c) correlating the existence of the LAG-3 to the LAG-3 related disease or condition in the subject.

In some embodiments, the present disclosure provides kits comprising the antibody polypeptide provided herein, optionally conjugated with a detectable moiety. The kits may be useful in detection of LAG-3 or diagnosis of LAG-3 related disease.

In some embodiments, the present disclosure also provides use of the antibody polypeptide provided herein in the manufacture of a medicament for treating a LAG-3 related disease or condition in a subject, in the manufacture of a diagnostic reagent for diagnosing a LAG-3 related disease or condition.

Advantages

The antibody polypeptides provided herein are advantageous over existing therapies in many aspects. For example, compared to existing LAG-3 antibodies, the antibody polypeptides provided herein have better binding affinity to human and monkey LAG-3, are more effective at blocking LAG-3 binding to cell surface MHC-II, more effective at blocking LAG-3 binding to LSECtin and Galectin-3, enhancing IL-2 pathway activity, and more effective at inducing IFNγ production. The antibody polypeptides provided herein are also advantageous in that they bind to a different epitope from that bound by control antibodies. The antibody polypeptides provided herein bind to mouse LAG-3, with affinity reaching picomolar level, which is advantageous for in vivo functional assays using the mice model.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1. Materials and Methods 1.1 Immunogen Generation Nucleic acid sequences encoding human LAG-3 ECD (Genbank Accession No. NP_002277), cynomolgus (cyno) LAG-3 ECD (Genbank Accession No. XP_005570011.1) and mouse LAG-3 ECD (Genbank Accession No. NP_032505) were synthesized by Sangon Biotech. LAG-3 gene fragments amplified from the synthesized nucleic acid were inserted into the expression vector pcDNA3.3 (ThermoFisher) containing human Fc-, mouse Fc-, or His-tag, respectively. Expi293 cells (Invitrogen-A14527) were transfected with the purified ECD expression vectors and cultured in Expi293™ Expression Medium (ThermoFisher) at 37° C., 5% $CO_2$ for 5 days. The harvested supernatant was used for protein purification. His-tagged proteins were purified using Ni-NTA column (GE healthcare-17-5247-01) and Fc-tagged proteins were purified using Protein A column (GE healthcare-17-5438-02).

1.2 Production of Benchmark Antibodies (BMK Abs) (W339-BMK1, W339-BMK7, W339-BMK8)

Gene sequences of anti-human LAG-3 benchmark antibodies W339-BMK1 and W339-BMK7 were synthesized based on the information disclosed in patents US20110150892 A1 and US 2017/0101472 A1, respectively. W339-BMK1 was based on the sequence of clone "25F7" and W339-BMK7 was based on the sequence of clone "H4sH15482P". W339-BMK8 was based on sequence of clone "BAP050-hum01" in WO2015138920 A1. All the benchmark antibodies are modified with human constant region of a IgG4 isotype that has a S228P mutation.

The synthesized gene sequences were inserted into plasmids pcDNA3.3 and transiently transfected into expi293F cells. After 5 days of culture, supernatants harvested from the culture of transiently transfected cells were used for protein purification. The benchmark antibodies were purified from the supernatants by protein A column (GE healthcare-17-5438-02).

1.3 Establishment of Stable Cell Lines

Human, mouse and cynomolgus LAG-3 transfectant cell lines were generated. Briefly, Flp-In-293 or CHO-K1 were transfected with pcDNA3.3 expression vector containing full length of human LAG-3 gene (Genbank Accession No. NP_002277) using Lipofectamine 2000 transfection kit (ThermoFisher-11668027) according to manufacturer's protocol. Flp-In-CHO and 293F cells were used for transfection with mouse and cynomolgus LAG-3 (Genbank Accession No. NP_032505 and XP_005570011.1), respectively. At 48-72 hours post transfection, the transfected cells were cultured in medium containing blasticidin for selection. LAG-3 expression was tested by Flow cytometry. Human, cyno and mouse LAG-3-expressing stable cell lines were obtained by limiting dilution.

2. Generation of VHH 2.1 Immunization

To induce humoral immune response towards LAG-3 in camelid animals, the animals were subcutaneously injected with recombinant mFc tagged human LAG-3 ECD and recombinant hFc tagged mouse LAG-3 ECD proteins, respectively. The immunizations were with intervals of 1 to 3 weeks and the dose ranged from 50 µg to 200 µg per injection for totally 8 doses.

2.2 Serum Titer Detection

The anti-human LAG-3 and anti-mouse LAG-3 titers in the immune animal serum was detected using human LAG-3.ECD.his and mouse LAG-3.ECD.his proteins by ELISA, respectively. 96-well plates (Nunc) were coated with soluble protein of human or mouse LAG-3 ECD overnight at 4° C. After blocking and washing the coated plates, serial dilutions of pre-immune or immune sera were transferred to the coated plates and incubated at room temperature for 1 h. The plates were then washed and subsequently incubated with secondary antibody Goat anti llama IgG-HRP (NB7242) for 1 h. After washing, TMB substrate was added and the color reaction was stopped by 2M HCl. The absorbance at 450 nm was read using a microplate reader (Molecular Device).

2.3 Library Construction 50 ml blood samples were collected at 6-7 days after the last two injections, respectively. Peripheral blood mononuclear cells (PBMCs) were purified by density gradient centrifugation in Ficoll-Paque PLUS (GE Healthcare, Little Chalfont, UK), resulting in the isolation of approximately $8 \times 10^7$ PBMCs. Total RNA was extracted from these PBMCs and transcribed into cDNA using oligo-dT and random primers and SuperScript III First-Strand Synthesis SuperMix System (Invitrogen, Carlsbad, Calif., USA) according to the manufacturers' recommendations.

The purified cDNA was then used as template to amplify the repertoire of Ig heavy chain-encoding gene segments with the use of signal peptide domain specific primers and CH2 domain specific primers. This amplification resulted in PCR fragments of approximately 900 bp (representing conventional IgG) and 700 bp (representing heavy-chain only IgG that lack a CH1 domain). The two classes of heavy chain encoding genes were then size-separated on agarose gels and the genes encoding heavy-chain only IgG were purified by QIAquick Gel Extraction Kit (Qiagen, Hilden, Germany). The purified fragments were used as templates to amplify the VHH repertoire with the use of framework1 (FR1) and framework4 (FR4) specific primer pairs. This amplification procedure introduced a Sfi I restriction site at the 5' end of FR1 and a Not I restriction site at the 3' end of FR4. The repertoire of PCR-amplified VHH genes of about 300-400 bp were loaded on agarose gels and purified by QIAquick Gel Extraction Kit. The purified fragments were then cut with Sfi I and Not I and purified by QIAquick PCR Purification Kit (Qiagen, Hilden, Germany). The VHH gene fragments were finally ligated in phagemid vector pFL249 and electrotransformed into *E. coli* TG1. After transformation, the TG1 cells were cultured in SOC medium with shaking at 200 rpm for 1 h, then the *E. coli* TG1 were plated onto 2YT agar plates supplemented with 100 µg/mL Carb and 1% (w/v) glucose, and cultured at 37° C. overnight. The next day, the colonies were scraped into liquid 2YT medium supplemented with ⅓ (v/v) of 80% glycerol and stored at −80° C.

2.4 Panning

To select VHH fragments that would effectively bind to LAG-3, the methods of protein panning was employed. 20 µg of LAG-3 ECD proteins were immobilized in 5 ml immune tube (Nunc, Rochester, Minn., USA) overnight at 4° C. with shaking at 400 rpm. The next day, after washing away unbound protein, the tube was blocked with 10% skim milk for 1 h at 25° C. Approximately $10^{12}$ cfu phages from the immune phage libraries added into non-coated immune tube blocked with 10% skim milk to deplete the non-specifically bound phage, then treated phage described above were added into the tube coated with LAG-3 ECD protein and incubated at 25° C. for 2 h. After extensive washing with PBST, the nonspecifically adsorbed phage were discarded and the target specifically bound phages were eluted by Glycine-HCl (pH2.2) and then neutralized by 1M Tris-HCl (pH8.0) for infection of exponentially growing TG1 cells. The infected TG1 cells were plated on 2YT agar plates containing 2% (w/v) glucose and 100 µg/ml ampicillin and cultured overnight at 37° C. On the next day, the colonies were scraped off the plate with 2YT and frozen at −80° C. by adding in ⅓ (v/v) 80% glycerol. The scraped bacteria libraries were inoculated into 2YT-Carb contain 100 µg/ml ampicillin, infected with helper phage M13Ko7 in 2YT medium with 50 µg/ml kanamycin and 1 mM IPTG for phage rescue and used as input for the next round of panning. In order to fish out the phage particles that would cross-react to monkey and mouse LAG-3, the alternate panning with monkey LAG-3 and mouse LAG-3 protein can be used.

2.5 Screening

After desired panning steps, phage infected TG1 cell colonies grown on the plates were scraped off and pFL249 phagemid containing VHH fragments were extracted using NucleoSpin® Plasmid (Macherey-Nagel). The VHH fragments were cloned by digestion of pFL249 plasmids with Sfi I and Not I (10-20U/µg, NEB) and then ligated into expression vector pETbac, which containing genes of 6-his and c-Myc-tag. The ligation products were transformed into E. coli BL21 (DE3) competent cells (TIANGEN) and then cultured in ZYM-5052 medium at 25° C. for 48 h with shaking at 230 rpm. The E. coli BL21 culture was centrifuged at 4000 rpm for 20 min to collect the supernatant. The supernatants were screening by ELISA and FACS binding assay for identifying anti-LAG-3 positive VHH clones.

ELISA assay was used as the first screen method to test the binding of VHH E. coli culture supernatants to LAG-3 ECD protein. Briefly, 96-well plates (Nunc) were coated with soluble protein of human or mouse LAG-3 ECD protein overnight at 4° C. After blocking and washing, the E. coli supernatants were transferred to the coated plates and incubated at room temperature for 1 h. The plates were then washed and subsequently incubated with secondary antibody Goat Anti-c-Myc-HRP (Bethyl) for 1 h. After washing, TMB substrate was added and the color reaction was stopped by 2M HCl. The absorbance at 450 nm was read using a microplate reader (Molecular Device).

In order to confirm the native binding of LAG-3 antibodies on conformational LAG-3 molecules expressed on cell membrane, flow cytometry analysis was performed with LAG-3 transfected cell lines and parental control cell lines. The cells were firstly incubated with the VHH E. coli supernatant samples in 96-well U-bottom plates (BD) at a density of $1\times10^5$ cells/well at 4° C. for 1 h, then with the secondary antibody Mouse Anti-c-Myc-biotin (Sigma) at 4° C. for 30 min, followed by streptavidin PE (eBioscience) in the dark at 4° C. for 20 min. 2 times of washings were applied between each steps and the cells were resuspended in 1×PBS/1% BSA for flow cytometry(Intellicyt) analysis.

2.6 Sequencing

The positive E. coli clones selected by ELISA and FACS screening were sent to Biosune (Shanghai, China) for nucleotide sequencing of VHH gene. The sequencing results were analyzed using CLC Main Workbench (Qiagen, Hilden, Germany).

2.7 VHH Protein Production

The BL21 E. coli clones harboring VHH gene were cultured in 40 ml of ZYM-5052 medium at 25° C. for 48 h with shaking at 230 rpm. The expression of his- and c-Myc-tag fused VHH protein in BL21 supernatant was confirmed by SDS-PAGE, and then purified using Ni-NTA column. The purity of VHH was determined by SDS-PAGE and analytic SEC-HPLC. For low supernatant expression clones, ultrasonic (Scientz, Ningbo, China) breaking E. coli cells was used to release soluble VHH proteins and whole cell lysates were purified.

2.8 Chimeric VHH-Fc (hIgG4) Protein Production

The clones of interest were converted to VHH-Fc (uIgG4) fusion antibodies. Briefly, the VHH genes were PCR amplified from the pET-bac vectors using VHH-specific cloning primers containing appropriate restriction sites then cloned by fusion into a modified human IgG4 Fc (S228P) expression pcDNA3.3 vector to create corresponding clones of VHH-Fc (uIgG4) chimeric antibody. 293F cells were transiently transfected with the vector for antibody expression. The cell culture supernatants containing antibodies were harvested and purified using Protein A chromatography.

3. Antibody Optimization 3.1 Humanization

VHHs with high affinity and specificity to LAG-3 were selected for humanization. "Best Fit" approach was used to humanize VHH chains. Amino acid sequences of VHH framework regions were blasted against human germline V-gene database, and humanized VHH sequences were generated by replacing human CDR sequences in the top hit with VHH CDR sequences using Kabat CDR definition. Certain residues in the framework region were back-mutated to camel source residue in order to maintain the affinity. Humanized genes were back-translated, codon optimized for mammalian expression, and synthesized by GENEWIZ. These genes were re-amplified with cloning primers containing appropriate restriction sites and cloned into a modified pcDNA3.3 vector to express humanized VHHs linked with human IgG4 Fc (S228P) region. After testing on LAG-3 binding using surface plasmon resonance (SPR), the variants with proper affinity were selected as humanized antibody leads.

3.2 Affinity Maturation

Each amino acid of three complementary-determining regions (CDR1, CDR2, and CDR3) of the parental VHH clone was individually mutated to other 20 amino acids using a site-directed mutagenesis method. DNA primers containing a NNS codon encoding twenty amino acids were used to introduce mutation to each targeted CDR position. The individual degenerate primers were used in site-directed mutagenesis reactions. 200 ng of the reaction products was electroporated into BL21 and expressed in 96-deep well plates (Axygen). The VHH mutants were screened by ELISA assay with supernatant of bacteria grown in 96-deep well plates. The clones exhibiting an OD 450 greater than 1.5-fold of the parental clone were further screening by SPR of the affinity of the mutants.

The point mutations in VHH determined to be beneficial for binding to antigen were further combined to gain enhanced affinity synergy. The combinatorial mutants were synthesized in GENEWIZ and expressed in BL21. Supernatant of the mutants were detected by SPR. After affinity maturation, a total of 9 humanized VHH antibodies showing strong response in reporter gene assay (RGA) reaction were selected and fused with human IgG4 Fc(S228P) region. The 9 matured VHH-Fc chimeric antibody (VHH Ab) were designated for short as: W3396-R2-1, W3396-R2-2, W3396-R2-3, W3396-R2-6, W3396-R2-10, W3396-R2-11, W3396-R2-12, W3396-R2-13 and W3396-R2-26H2. As shown in FIGS. 1A and 1B, the 9 affinity matured VHH Abs show enhanced reactivity in RGA Assay as compared with the parental VHH Ab (short as W3396-Z4).

4. Antibody Characterization

4.1 Binding of LAG-3 Antibodies to Cell Surface LAG-3

Figure 2A:
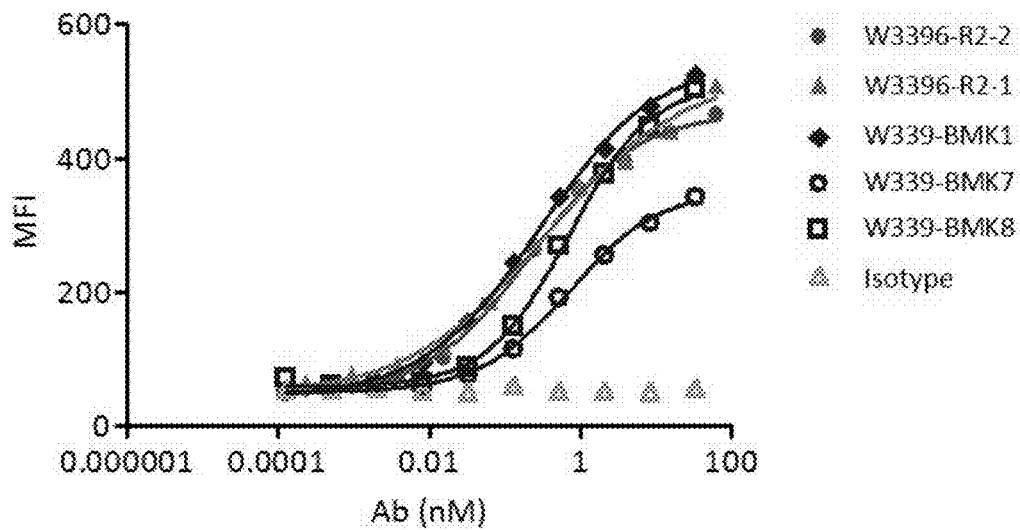
FIG. 2A shows that W3396-R2-1 and W3396-R2-2 bind to cell surface human LAG-3 with a comparable or better EC50 than that of benchmark antibodies (BMK Abs) (W339-BMK1, W339-BMK7, W339-BMK8), as measured by fluorescence-activated cell sorting (FACS).
Figure 2B:
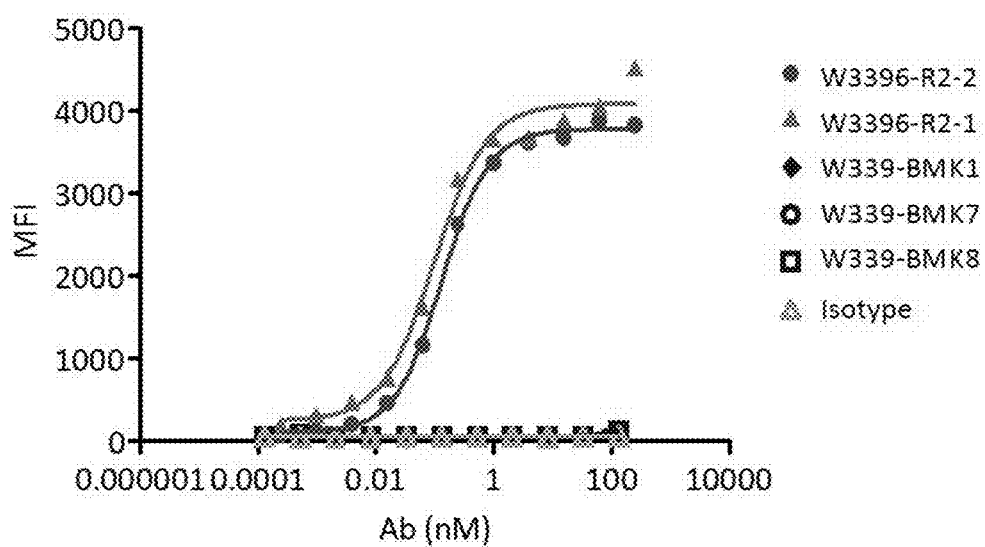
FIG. 2B shows that W3396-R2-1 and W3396-R2-2 bind to cell surface mouse LAG-3 with an EC50 of 0.1, or 0.13 nM, as measured by FACS.
Figure 2C:
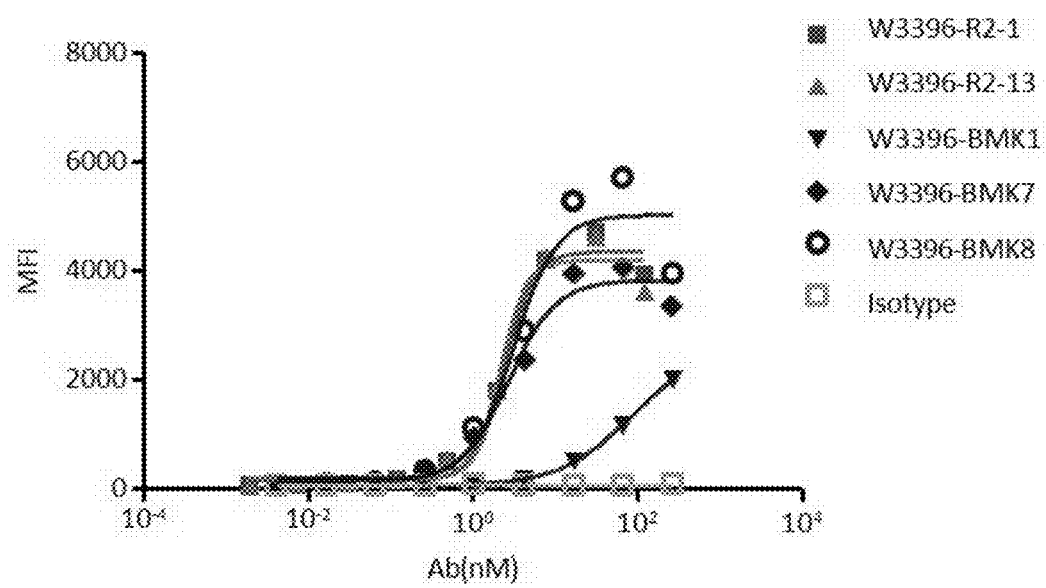
FIG. 2C shows that W3396-R2-1 and W3396-R2-13 bind to cell surface cynomolgus LAG-3 with an EC50 of 2.34, or 2.16 nM, as measured by FACS.

Serial dilutions of testing antibodies (W3396-R2-2 and W3396-R2-1), benchmark antibodies (W339-BMK1, W339-BMK7 and W339-BMK8), and negative control antibodies (Isotype IgG4) were incubated respectively with human LAG-3 transfected cells, and then the binding of antibodies to the cell surface LAG-3 was detected by PE-labeled secondary antibodies via flow cytometry (FACS). Similarly, cross-reactivity to cynomolgus or murine LAG-3 was tested by FACS with cyno or murine LAG-3 transfected cell lines. FIGS. 2A and 2B show that both W3396-R2-2 and W3396-R2-1 bind to cell surface human and mouse LAG-3, respectively. The binding EC50 to human LAG-3 was better than that of benchmark antibodies (BMK Abs). BMK Abs do not bind to mouse LAG-3 (FIG. 2B). W3396-R2-13 and W3396-R2-1 were also tested for binding to cell surface monkey LAG-3 and showed a comparable or better EC50 value than that of BMK Abs (see FIG. 2C).

4.2 Blocking of LAG-3 to Cell Surface MHC-II with LAG-3 Antibody by FACS

Figure 3A:
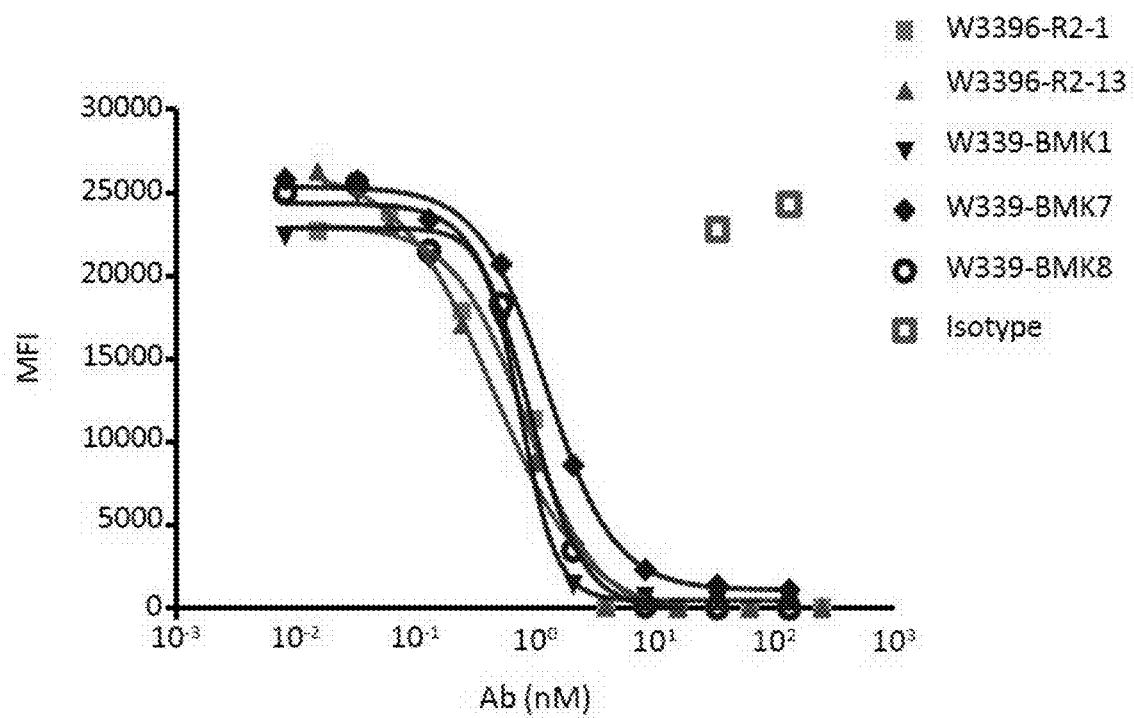
FIG. 3A and FIG. 3B show that W3396-R2-1, W3396-R2-2 and W3396-R2-13 block the binding of human LAG-3 to cell surface human MHC-II with a comparable or better IC50 than that of BMK Abs (W339-BMK1, W339-BMK7 and W339-BMK8), as measured by FACS.
Figure 3B:
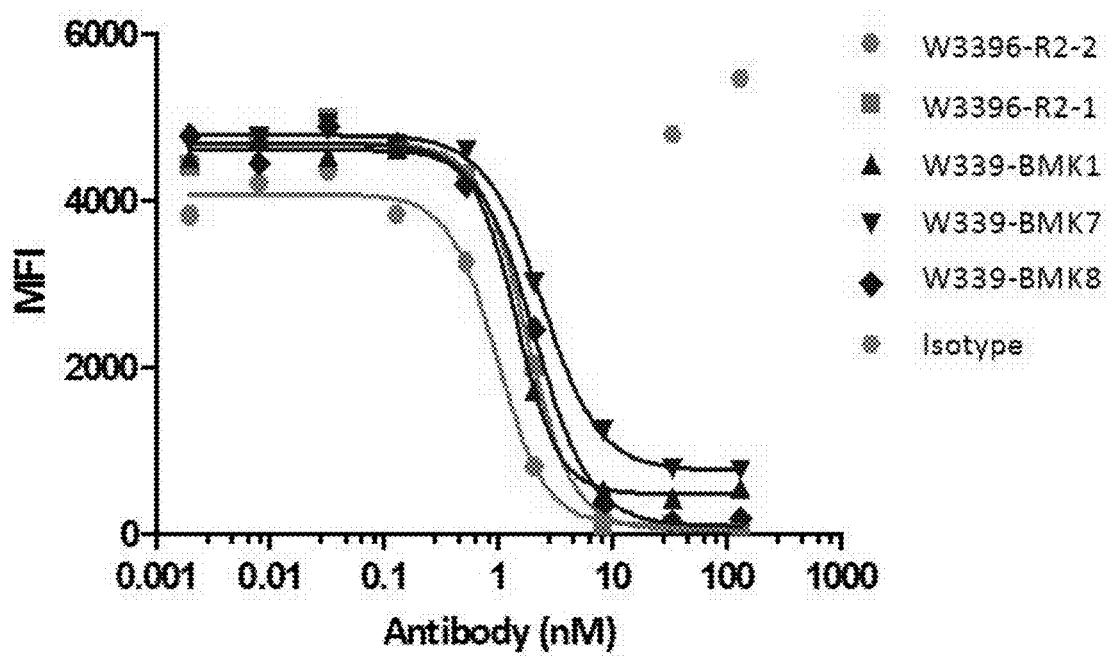
Figure 3C:
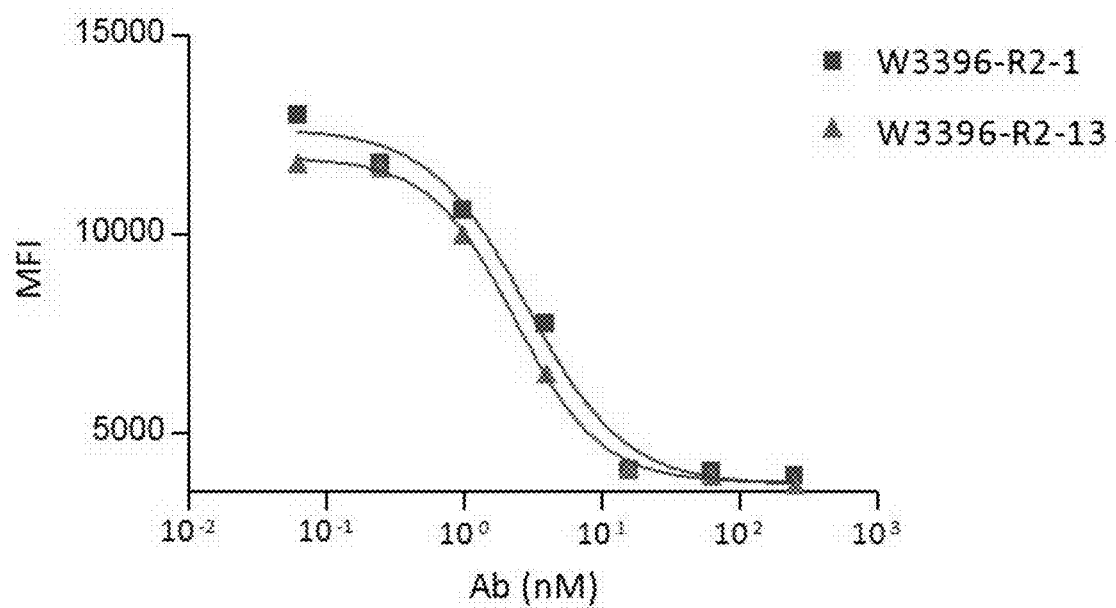
FIG. 3C shows that W3396-R2-1 and W3396-R2-13 block the binding of mouse LAG-3 to cell surface mouse MHC-II with an IC50 of 2.9, or 2.4 nM, as measured by FACS.

Serial dilutions of antibodies were pre-mixed with mouse Fc (mFc)-tagged human LAG-3 in 1% BSA-PBS at 4° C. for 30 min. The mixture was transferred into the 96-well plates seeded with Raji cells. Goat anti-mouse IgG Fc-PE antibody was used to detect the binding of LAG-3 protein to Raji cells. The mean fluorescence intensity (MFI) was evaluated by flow cytometry and analyzed by FlowJo. For testing the blocking of mouse LAG-3 binding to mouse cell surface MHC-II, mFc-tagged mouse protein and A20 cells were used. FIG. 3A shows that W3396-R2-1 and W3396-R2-13 block the binding of human LAG-3 to MHC-II on Raji cells with a comparable or better IC50 than that of BMK Abs (W339-BMK1, W339-BMK7, W339-BMK8). FIG. 3C shows that W3396-R2-1 and W3396-R2-13 block the binding of mouse LAG-3 to mouse MHC-II on A20 cells with IC50 of 2.4-2.9 nM. FIG. 3B shows that W3396-R2-1 and W3396-R2-2 block the binding of human LAG-3 to human MHC-II on A20 cells with an IC50 of 0.99-1.78 nM.

Figure 4A:
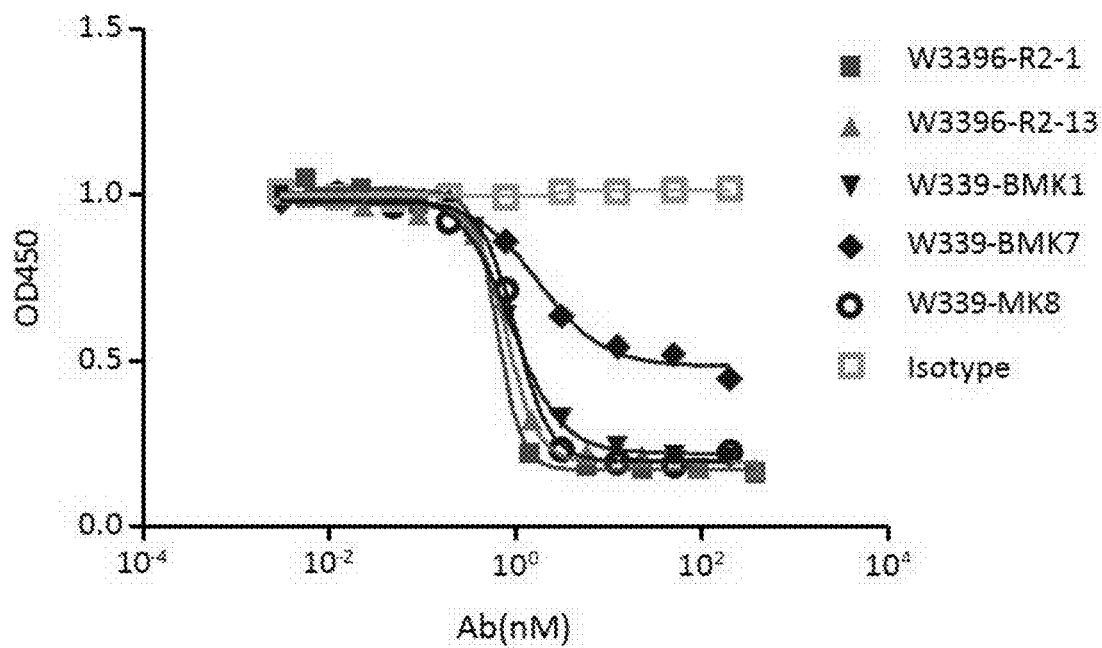
FIG. 4A and FIG. 4B show that W3396-R2-1, W3396-R2-2 and W3396-R2-13 block the binding of human LAG-3 to sinusoidal endothelial cell lectin (LSECtin) with a comparable or better IC50 than that of BMK Abs (W339-BMK1, W339-BMK7 and W339-BMK8), as measured by enzyme-linked immunosorbent assay (ELISA).
Figure 4B:
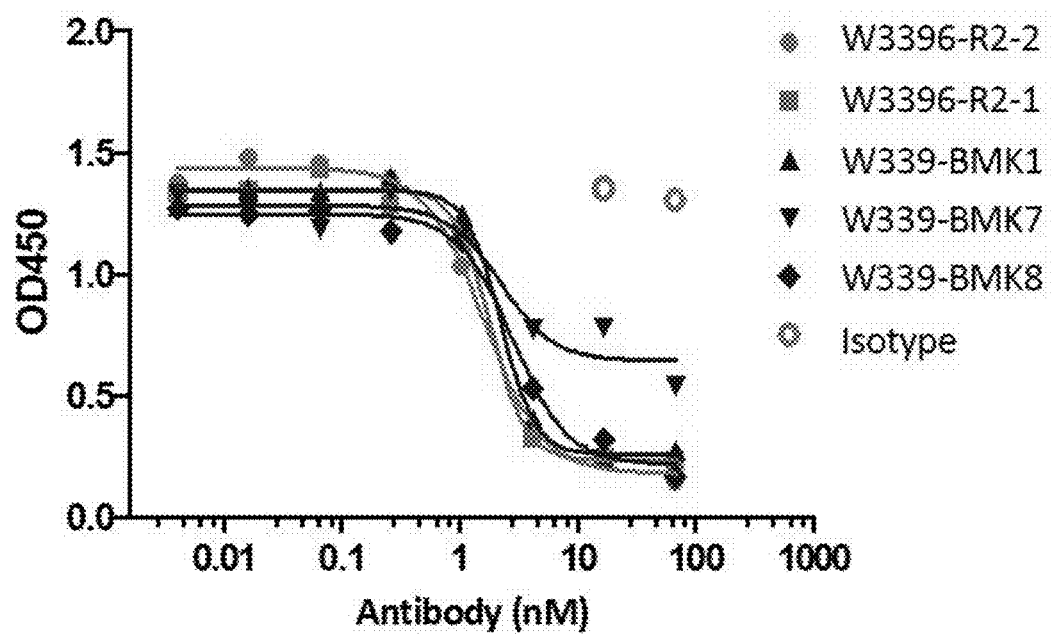
Figure 4C:
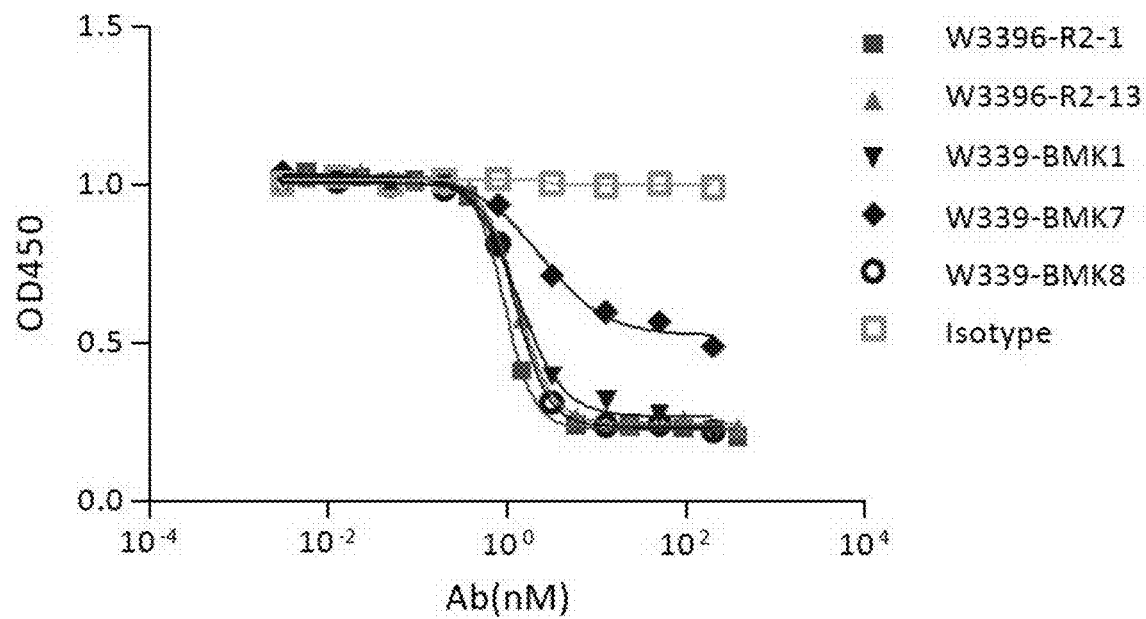
FIG. 4C and FIG. 4D show that W3396-R2-1, W3396-R2-2 and W3396-R2-13 block the binding of human LAG-3 to Galectin-3 (Gal-3) with a comparable or better IC50 than that of BMK Abs (W339-BMK1, W339-BMK7 and W339-BMK8), as measured by ELISA.
Figure 4D:
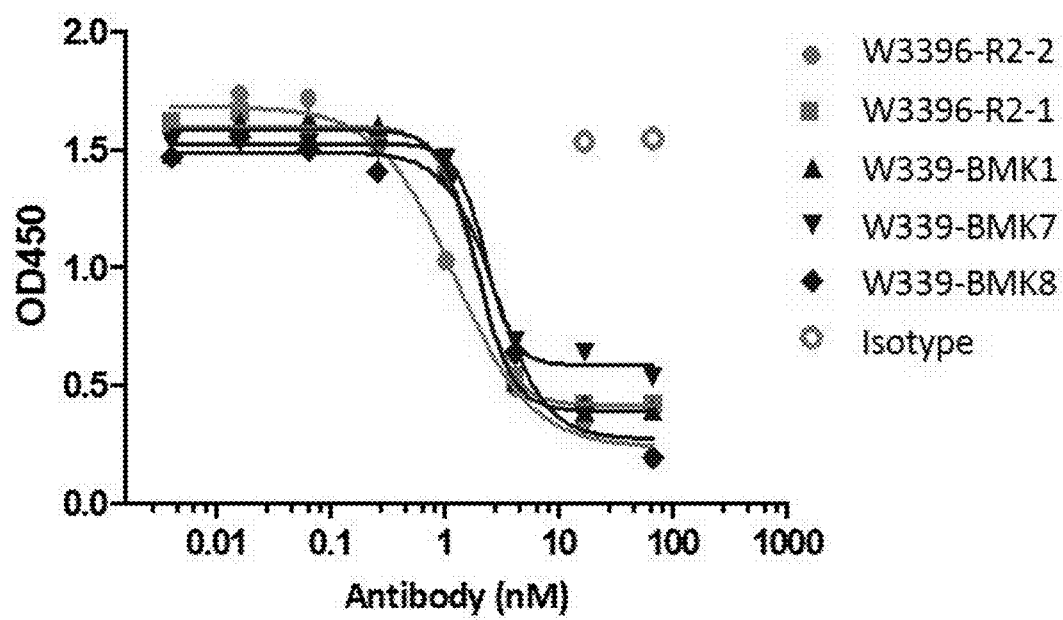

4.3 Blocking of LAG-3 to LSECtin and Galectin-3 by ELISA 96-well plates were coated with human LSECtin or Galectin-3 at 0.5 µg/ml overnight at 4° C., respectively. Serial dilutions of testing antibodies(W3396-R2-1 and W3396-R2-13), benchmark antibodies (W339-BMK1, W339-BMK7 and W339-BMK8), and negative control antibodies (Isotype IgG4) were pre-mixed with mFc-tagged human LAG-3 in 1% BSA-PBS at 4° C. for 30 min. After blocking and washing, the mixture was transferred to the plates and incubated at room temperature for 1 h. The plates were then washed and subsequently incubated with the secondary antibody goat-anti Mouse IgG Fc-HRP for 1 h. After washing, TMB substrate was added and the color reaction was stopped by 2M HCl. The absorbance at 450 nm was read using a microplate reader. FIG. 4A and FIG. 4B show that W3396-R2-1, W3396-R2-2 and W3396-R2-13 block the binding of human LAG-3 to LSECtin with a comparable and better IC50 than that of BMK Abs. FIGS. 4C and 4D show that W3396-R2-1, W3396-R2-2 and W3396-R2-13 block the binding of human LAG-3 to Galectin-3.

4.4 Binding Kinetic Affinity of LAG-3 Tested by Surface Plasmon Resonance (SPR)

Antibodies were characterized for affinity and binding kinetics to human LAG-3 by SPR assay using Biacore 8K. Goat anti-human Fc was pre-immobilized to a sensor chip (CM5), and anti-LAG-3 antibodies were captured when injected to the chip. Various concentrations of human LAG-3 protein and running buffer were flowed through the sensor chip at a flow rate of 30 µL/min for an association phase of 300 s, followed by 3600 s dissociation. The association ($K_{on}$) and dissociation curve ($K_{off}$) was fitted by 1:1 Langmuir binding model using Biacore 8K Evaluation Software. The equilibrium dissociation constant (KD) is calculated from the ratio of $K_{off}/K_{on}$. Table 4A and 4B show the affinities of W3396-R2-1, W3396-R2-2 and W3396-R2-13 to human LAG-3, and the affinities to mouse LAG-3.

TABLE 4A

Binding kinetic affinity by SPR.

| protein | Abs | ka (1/Ms) | kd (1/s) | KD (M) |
|---|---|---|---|---|
| Human Lag-3 | W3396-R2-1 | 1.66E+05 | 2.70E−05 | 1.62E−10 |
|  | W3396-R2-13 | 4.84E+04 | 1.97E−04 | 4.06E−09 |
| Mouse Lag-3 | W3396-R2-1 | 8.19E+05 | <1.00E−06 | <1.22E−12 |
|  | W3396-R2-13 | 1.05E+06 | <1.00E−06 | <9.52E−13 |
| Separate exp. |  |  |  |  |
| Human Lag-3 | W339-BMK1 | 4.87E+05 | 3.34E−04 | 6.85E−10 |
|  | W339-BMK7 | 2.13E+05 | 1.06E−04 | 4.97E−10 |
|  | W339-BMK8 | 1.44E+05 | <1.00E−06 | <6.94E−12 |

TABLE 4B

| Analyte | Ligand | ka (1/Ms) | kd (1/s) | KD (M) |
|---|---|---|---|---|
| Human Lag3 | WBP339-BMK1.IgG4 | 1.09E+06 | 3.57E−04 | 3.26E−10 |
|  | W3396-R2-1 | 1.49E+05 | 2.73E−05 | 1.83E−10 |
|  | W3396-R2-2 | 2.41E+05 | 3.97E−05 | 1.65E−10 |
| Mouse Lag3 | W3396-R2-1 | 1.02E+06 | 2.31E−06 | 2.27E−12 |
|  | W3396-R2-2 | 1.74E+06 | <1.00E−06 | <5.75E−13 |

4.5 Binding Affinity of LAG-3 Antibodies to Cell Surface LAG-3 Molecules Tested by FACS Antibody binding affinity to cell surface LAG-3 was measured by FACS analysis. Human LAG-3 transfected cells were transferred in to 96-well U-bottom plates at a density of $5\times10^5$ cells/ml. Tested antibodies were serially diluted in wash buffer (1×PBS/1% BSA) and incubated with cells at 4° C. for 1 h. The secondary antibody goat anti-human IgG Fc FITC (3.5 moles FITC per mole IgG) was added and incubated at 4° C. in the dark for 0.5 h. The cells were then washed once and re-suspended in 1×PBS/1% BSA, and analyzed by flow cytometry. Fluorescence intensity will be converted to bound molecules/cell based on the quantitative beads (Quantum™ MESF Kits, Bangs Laboratories, Inc.). Table 5A and 5B show the affinity of W3396-R2-1, W3396-R2-2 and W3396-R2-13 to cell surface human, cyno and mouse LAG-3 in different batches of experiments, in comparison to BMK Abs (W339-BMK1, W339-BMK7, W339-BMK8).

Table 5A

Affinity test by FACS.

| | W3396-R2-1 | W3396-R2-13 | W339-BMK1 | W339-BMK7 | WBP339-BMK8 |
|---|---|---|---|---|---|
| Human Lag-3 | | | | | |
| Bmax (M) | 2.5E−10 | 2.0E−10 | 3.2E−10 | 2.9E−10 | 3.4E−10 |
| KD (M) | 8.1E−10 | 9.2E−10 | 1.4E−09 | 1.2E−09 | 8.3E−09 |
| $r^2$ | 0.99 | 1.00 | 1.00 | 1.00 | 0.99 |
| Cyno Lag-3 | | | | | |
| Bmax | 2.8E−10 | 3.1E−10 | 2.2E−10 | 2.8E−10 | 1.9E−10 |
| KD | 3.3E−09 | 5.0E−09 | 1.4E−08 | 3.3E−09 | 2.9E−08 |
| $r^2$ | 1.00 | 0.98 | 0.97 | 1.00 | 0.96 |
| Mouse Lag-3 | | | | | |
| Bmax (M) | 5.7E−11 | 5.3E−11 | | | |
| KD (M) | 5.7E−11 | 5.4E−11 | | | |
| $r^2$ | 1.00 | 0.98 | | | |

TABLE 5B

| | W3396-R2-1 | W3396-R2-2 | WBP339-BMK1 |
|---|---|---|---|
| Human Lag3 | | | |
| Bmax (M) | 5.4E−11 | 4.7E−11 | 6.3E−11 |
| KD (M) | 4.6E−10 | 4.6E−10 | 4.2E−10 |
| r2 | 0.99 | 0.99 | 0.97 |
| Cyno Lag3 | | | |
| Bmax (M) | 3.8E−10 | 3.0E−10 | 3.0E−10 |
| KD (M) | 6.3E−09 | 9.9E−09 | 1.9E−08 |
| r2 | 0.97 | 0.97 | 0.99 |

4.6 Cross-Reactivity to Human CD4

Figure 5A:
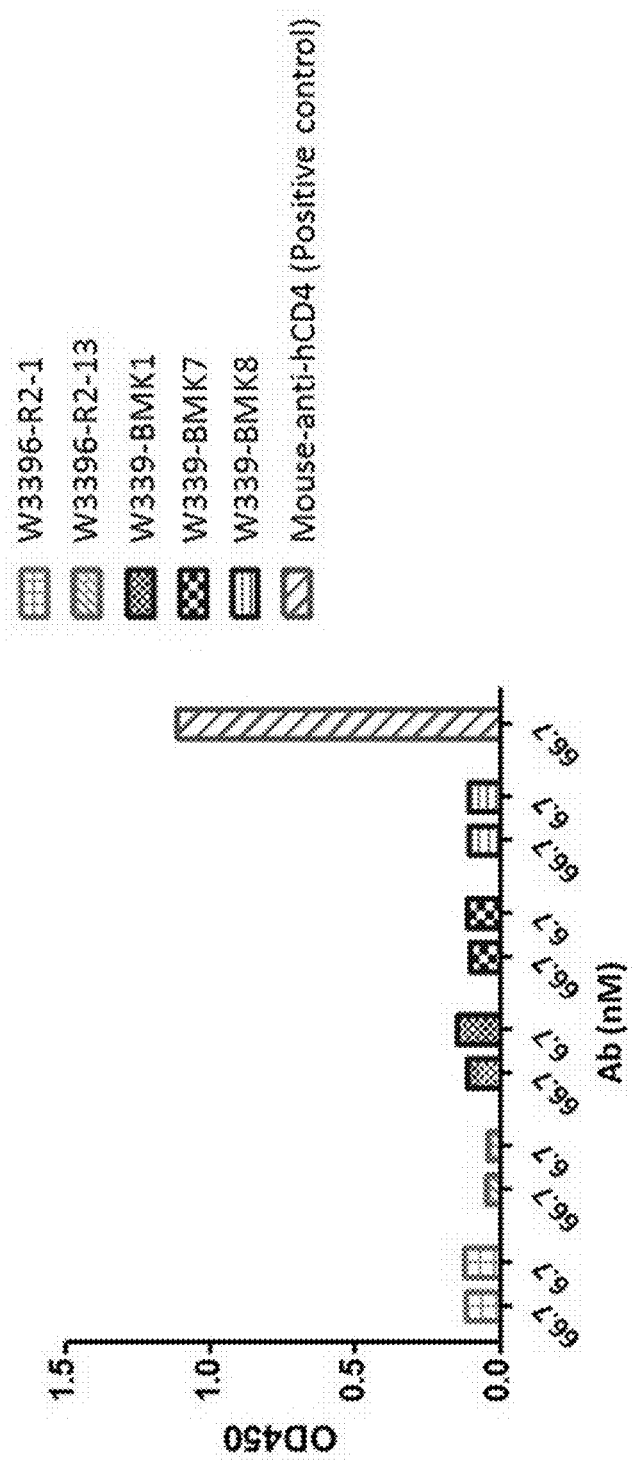
FIGS. 5A and 5B show that W3396-R2-1, W3396-R2-2 and W3396-R2-13 do not bind to human CD4, as measured by ELISA.
Figure 5B:
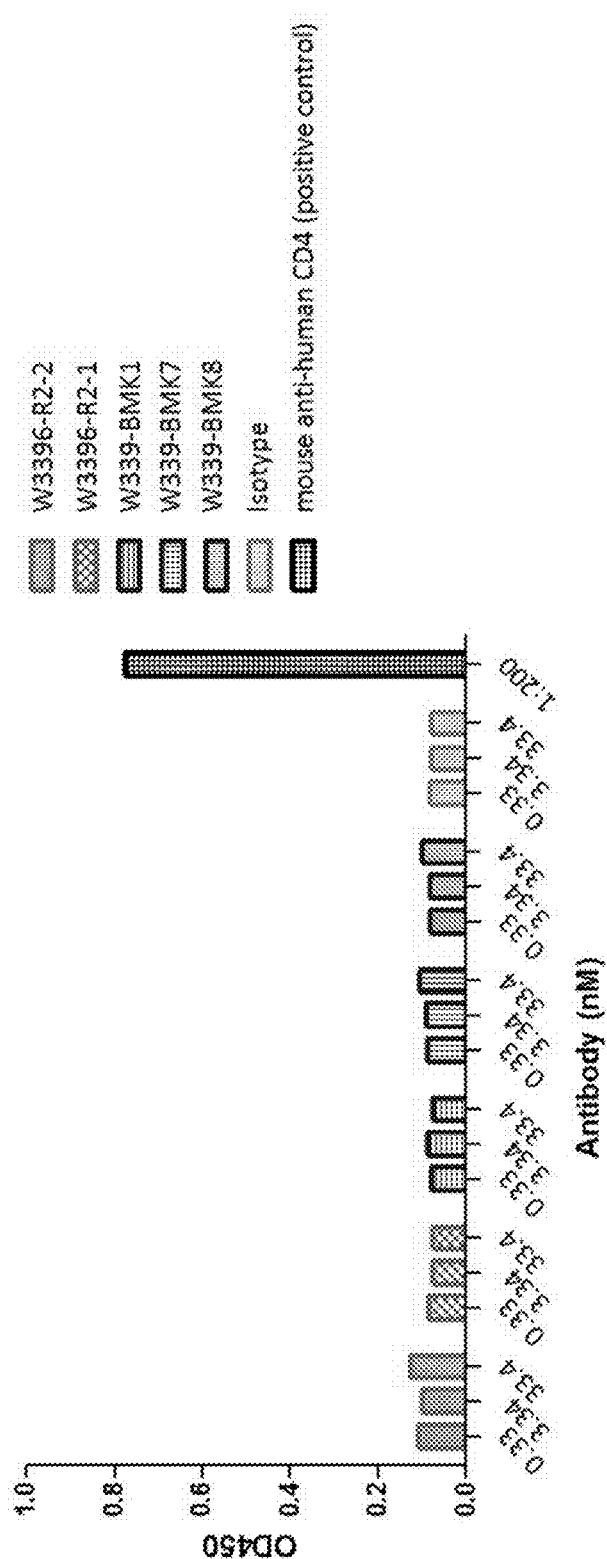

Cross-reactivity to human CD4 was measured by ELISA. Plates were coated with human CD4 at 1 μg/ml overnight at 4° C. After blocking and washing, 1 μg/ml of LAG-3 antibodies were added to the plates and incubated at room temperature for 1 h. The plates were then washed and subsequently incubated with goat-anti human IgG Fc-HRP for 45 min. After washing, TMB substrate was added and the color reaction was stopped by 2M HCl. The absorbance at 450 nm was read using a microplate reader. This assay indicates no cross-reactivity of W3396-R2-1, W3396-R2-2 and W3396-R2-13 to human CD4 (FIGS. 5A and 5B).

4.7 Epitope Binning Against W339-BMK1, W339-BMK7 and W339-BMK8

Figure 6:
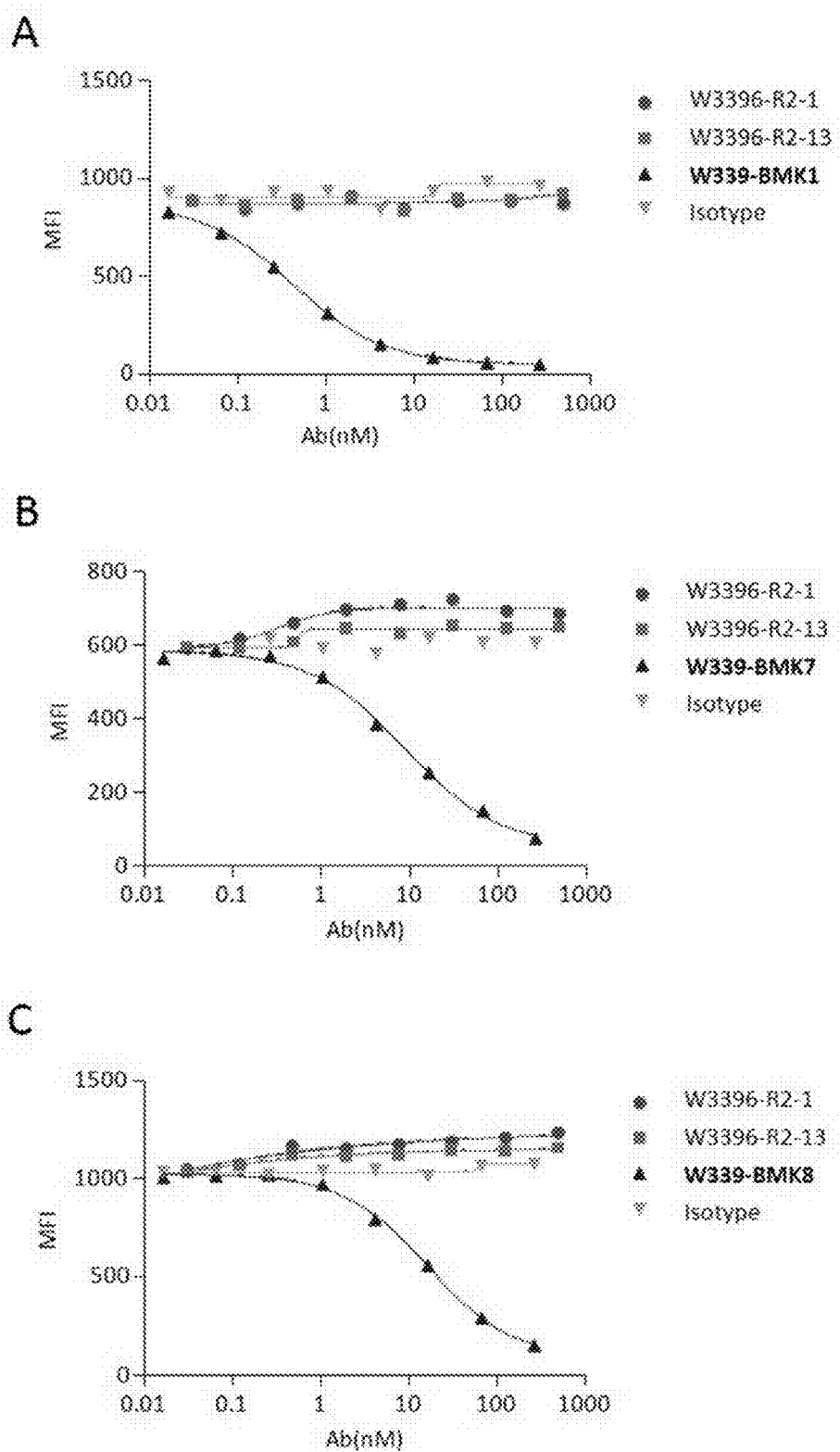
FIGS. 6A-6C show that W3396-R2-1 and W3396-R2-13 have different epitope bin from W339-BMK1, W339-BMK7 and W339-BMK8, as measured by FACS.

The binding epitope of LAG-3 antibodies was binned against benchmark antibodies W339-BMK1, W339-BMK7 and W339-BMK8 by FACS assay. Briefly, biotinylated W339-BMK1 at 0.3 μg/ml was premixed with serial dilutions of W3396-R2-1, W3396-R2-13 or W339-BMK1 Ab, then the mixtures were incubated with human LAG-3 transfected cells for 1 hour. Streptavidin-PE antibody (Jackson Immunoresearch Lab) was used to detect the binding of benchmark antibodies to cells. Similarly, the binning tests against W339-BMK7 and W339-BMK8 were performed as the description above (The biotinylated W339-BMK7 and W339-BMK8 were used at 1 μg/ml). The MFI was evaluated by flow cytometry and analyzed by FlowJo. FIG. 6 shows that W3396-R2-1 and W3396-R2-13 have different epitope bin from W339-BMK1 (FIG. 6A), W339-BMK7 (FIG. 6B), and W339-BMK8 (FIG. 6C), respectively.

4.8 Epitope Mapping

Alanine scanning experiments on human LAG-3 were conducted and their effect to antibody binding was evaluated. Alanine residues on human LAG-3 were mutated to glycine codons, and all other residues (except cysteine residues) were mutated to alanine codons. For each residue of the human LAG-3 extracellular domain (ECD), point amino acid substitutions were made using two sequential PCR steps. A pcDNA3.3-LAG-3-D12.mFC plasmid that encodes ECD domain 1 and domain 2 of human LAG-3 and a C-terminal mFC-tag was used as template, and a set of mutagenic primer was used for first step PCR using the QuikChange lightning multiple site-directed mutagenesis kit (Agilent technologies, Palo Alto, Calif.). Dpn I endonuclease was used to digest the parental template after mutant strand synthesis reaction. In the second-step PCR, linear DNA expression cassette which composed of a CMV promoter, extracellular domain 1 and domain 2 (D12) of LAG-3, a mFc-tag and a herpes simplex virus thymidine kinase (TK) polyadenylation was amplified and transiently expressed in Expi293 cells at 37° C. (Life Technologies, Gaithersburg, Md.), quantified by Protein A-HPLC and mFC-ELISA quantification Kit (Bethyl, USA). Monoclonal antibody W3396-R2-2 and 3 BMK Abs (i.e. W339-BMK1, W339-BMK7, W339-BMK8) (2 μg/ml) were coated in plates for ELISA binding assay. After interacting with the supernatant that contains quantified LAG-3 mutants or human LAG-3-ECD.D12.mFC protein, HRP conjugated anti-mFC antibody (1:5000; BetHyl, USA) was added as detection antibody. Absorbance was normalized according to the average of control mutants. After setting an additional cutoff to the binding fold change (<0.75), the final determined epitope residues were identified.

The results show that LAG-3 has an extracellular domain of 422 a.a. (V29-L450), and 132 a.a. of domain 1 (G37-Q168) were performed in alanine scanning experiments for epitope mapping. As no existed LAG-3 structure, the structure of the LAG-3 (a.a.: 31-431) was modeled based on the known structure of the myelin-associated glycoprotein (PDB: 5FLU, sequence identity 18%). Based on alanine scanning results, hotspots were identified as shown in Table 6A-6D and FIGS. 12A-12E. In conclusion, LAG-3 has an extracellular domain of 422 a.a. (V29-L450), and 132 a.a. of domain 1 (G37-Q168) were performed in alanine scanning experiments for epitope mapping. As the sequence identity is only 18%, the model and labeled hot spots just for reference. Among the BMK Abs, W339-BMK1 (BMS) claimed its epitope which consist with our epitope mapping results. One characteristic of W339-BMK1/BMK7 like Ab binds to the W92 which belongs to the extra loop (G70-Y99), while W339-BMK8 like Ab binds to L134-P138 region. W3396-R2-2 belongs to W339-BMK8 like Ab, however, W3396-R2-2 binds to a unique epitope, i.e. V104, which is not found in the three tested benchmark antibodies.

TABLE 6A

Hotspots of W339-BNIK1 antibody

| Residue | | Fold Change |
|---|---|---|
| G | 37 | 0.510 |
| L | 42 | 0.636 |
| A | 59 | 0.718 |
| V | 61 | 0.612 |
| W | 63 | 0.561 |
| H | 65 | 0.675 |
| P | 89 | 0.171 |
| W | 92 | 0.472 |
| T | 100 | 0.723 |
| V | 101 | 0.403 |
| L | 122 | 0.648 |
| A | 139 | 0.645 |
| D | 143 | 0.676 |
| G | 145 | 0.642 |
| E | 146 | 0.711 |
| Y | 147 | 0.548 |
| A | 149 | 0.660 |
| A | 150 | 0.734 |
| L | 153 | 0.673 |
| D | 155 | 0.744 |
| L | 164 | 0.374 |
| R | 165 | 0.744 |

TABLE 6B

Hotspots of W339-BATK7 antibody

| Residue | | Fold Change |
|---|---|---|
| G | 37 | 0.415 |
| A | 40 | 0.677 |
| L | 42 | 0.463 |
| P | 43 | 0.624 |
| A | 59 | 0.614 |
| V | 61 | 0.475 |
| T | 62 | 0.718 |
| W | 63 | 0.377 |
| H | 65 | 0.558 |
| H | 85 | 0.750 |
| A | 87 | 0.547 |
| W | 92 | 0.449 |
| T | 100 | 0.714 |
| V | 101 | 0.354 |
| L | 122 | 0.529 |
| A | 139 | 0.547 |
| D | 143 | 0.548 |
| G | 145 | 0.536 |
| E | 146 | 0.558 |
| Y | 147 | 0.336 |
| A | 149 | 0.662 |
| A | 150 | 0.672 |
| L | 153 | 0.537 |
| D | 155 | 0.628 |
| R | 156 | 0.655 |
| R | 163 | 0.678 |
| L | 164 | 0.392 |

TABLE 6C

Hotspots of W339-BATK8 antibody

| Residue | | Fold Change |
|---|---|---|
| G | 37 | 0.278 |
| A | 40 | 0.609 |
| L | 42 | 0.298 |
| P | 43 | 0.510 |
| A | 59 | 0.524 |
| V | 61 | 0.515 |
| T | 62 | 0.739 |
| W | 63 | 0.174 |
| H | 65 | 0.492 |
| T | 100 | 0.679 |
| V | 101 | 0.251 |
| L | 102 | 0.745 |
| L | 122 | 0.382 |
| G | 130 | 0.117 |
| D | 131 | 0.038 |
| L | 134 | 0.039 |
| W | 135 | 0.046 |
| L | 136 | 0.035 |
| R | 137 | 0.098 |
| P | 138 | 0.103 |
| A | 139 | 0.372 |
| D | 143 | 0.450 |
| G | 145 | 0.457 |
| E | 146 | 0.564 |
| Y | 147 | 0.194 |
| A | 149 | 0.728 |
| A | 150 | 0.744 |
| V | 151 | 0.035 |
| L | 153 | 0.595 |
| D | 155 | 0.695 |
| R | 163 | 0.646 |
| L | 164 | 0.286 |
| L | 166 | 0.750 |
| G | 167 | 0.729 |

TABLE 6D

Hotspots of W3396-R2-2 antibody

| Residue | | Fold Change |
|---|---|---|
| G | 37 | 0.234 |
| A | 38 | 0.721 |
| A | 40 | 0.559 |
| L | 42 | 0.284 |
| P | 43 | 0.487 |
| A | 59 | 0.497 |
| V | 61 | 0.405 |
| T | 62 | 0.674 |
| W | 63 | 0.150 |
| H | 65 | 0.452 |
| P | 72 | 0.750 |
| T | 100 | 0.617 |
| V | 101 | 0.219 |
| L | 102 | 0.692 |
| V | 104 | 0.534 |
| R | 119 | 0.683 |
| L | 122 | 0.320 |
| G | 130 | 0.093 |
| D | 131 | 0.060 |
| F | 132 | 0.666 |
| S | 133 | 0.740 |
| L | 134 | 0.047 |
| W | 135 | 0.053 |
| L | 136 | 0.047 |
| R | 137 | 0.096 |
| P | 138 | 0.099 |
| A | 139 | 0.307 |
| D | 143 | 0.467 |
| G | 145 | 0.390 |
| E | 146 | 0.507 |
| Y | 147 | 0.158 |
| A | 149 | 0.641 |
| A | 150 | 0.698 |
| V | 151 | 0.048 |
| L | 153 | 0.511 |
| D | 155 | 0.635 |
| R | 163 | 0.557 |

TABLE 6D-continued

Hotspots of W3396-R2-2 antibody

| Residue | | Fold Change |
|---|---|---|
| L | 164 | 0.218 |
| L | 166 | 0.699 |
| G | 167 | 0.679 |

4.9 Effects of Human LAG-3 Antibodies in Reporter Gene Assay

Figure 7A:
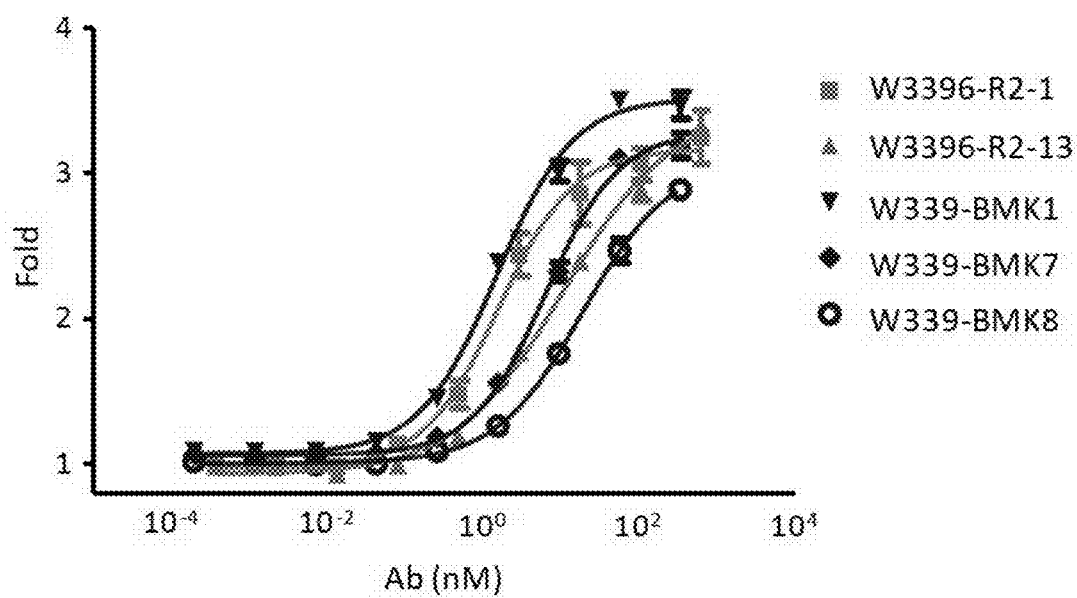
FIGS. 7A and 7B show that W3396-R2-1, W3396-R2-2 and W3396-R2-13 enhance IL-2 pathway activity with a comparable or better EC50 than that of BMK Abs (W339-BMK1, W339-BMK7 and W339-BMK8), as measured by RGA assay.
Figure 7B:
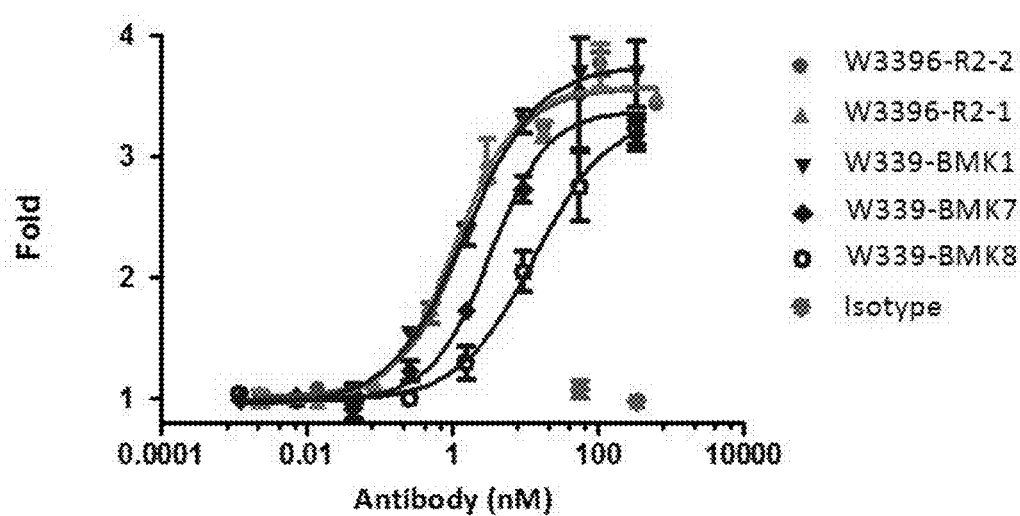

Jurkat cells stably co-transfected with human LAG-3 and IL-2 luciferase reporter gene (Promega) were prepared in house. The cells were seeded in 96-well plates along with Raji cells in the presence of Staphylococcal enterotoxin E (SEE) (Toxin Technology-ET404). Serial dilutions of testing antibodies were added to the cells and incubated overnight at 37° C., 5% $CO_2$. After incubation, reconstituted luciferase substrate was added and the luciferase intensity was measured by a microplate spectrophotometer. The data shown in FIGS. 7A-7B indicate that W3396-R2-1, W3396-R2-2 and W3396-R2-13 enhance IL-2 pathway activity in RGA assay with a comparable or better EC50 than that of BMK Abs (W339-BMK1, W339-BMK7, W339-BMK8).

Figure 8A:
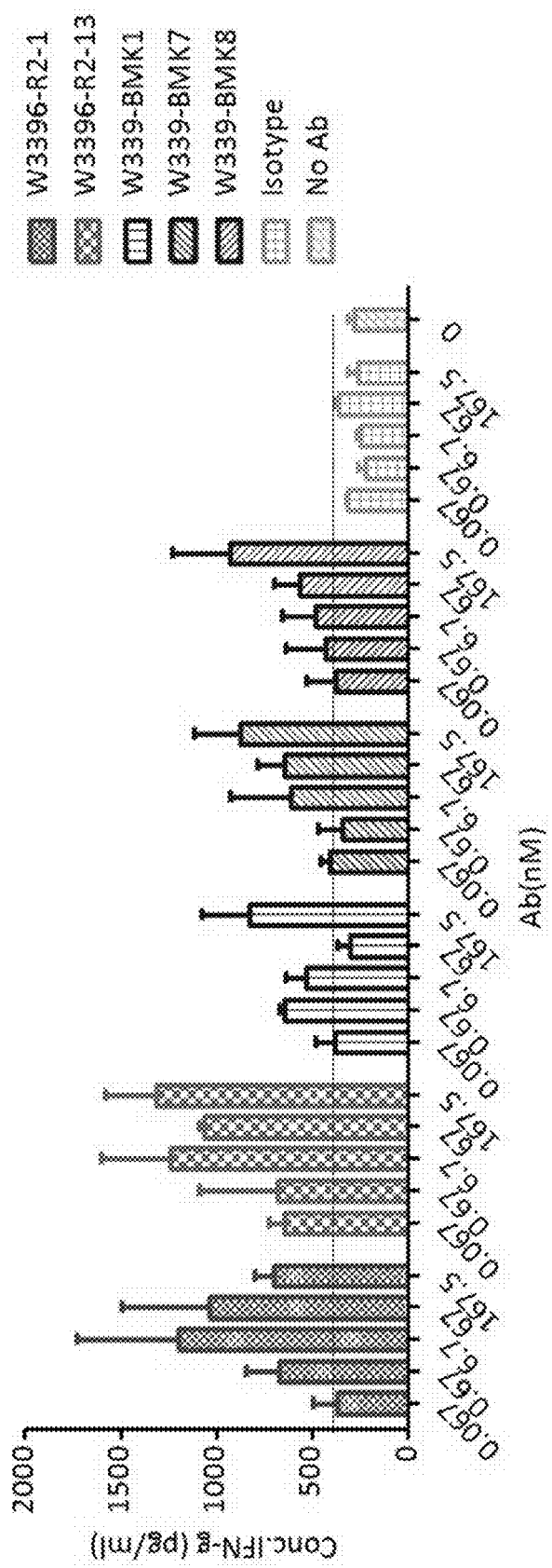
FIGS. 8A and 8B show that W3396-R2-1, W3396-R2-2 and W3396-R2-13 are comparable to or more potent than the BMK Abs (W339-BMK1, W339-BMK7 and W339-BMK8) in promoting human T cell IFN-γ secretion, as measured by human Mixed Lymphocyte Reaction (MLR) assay.
Figure 8B:
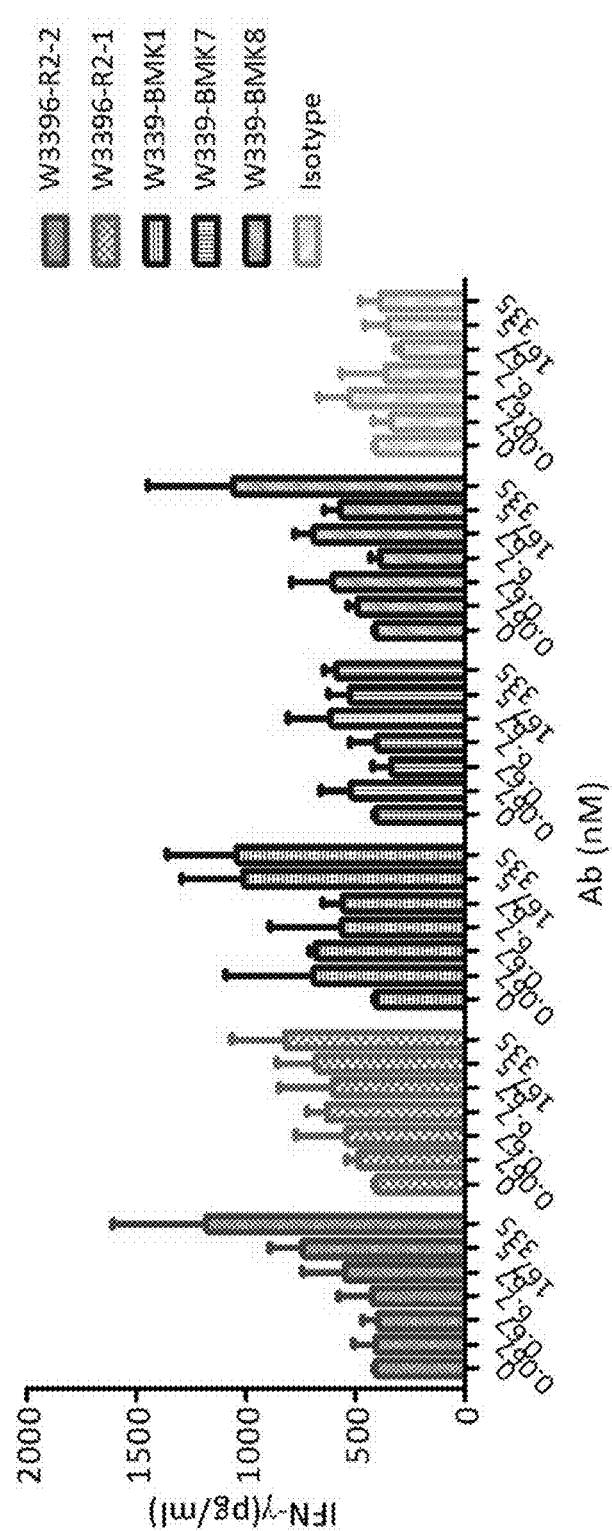

4.10 Effects of Human LAG-3 Antibodies on Human Allogeneic Mixed Lymphocyte Reaction Human PBMCs were freshly isolated from healthy donors using Ficoll-Paque PLUS gradient centrifugation. Monocytes were isolated using human monocyte enrichment kit according to the manufacturer's instructions (Miltenyi, biotec-130-050-201). Monocytes were cultured in medium containing GM-CSF (R&D) and IL-4 (R&D) for 5 to 7 days to generate immature dendritic cells (iDC). Human $CD4^+$ T cells were isolated using human $CD4^+$ T cell enrichment kit according to the manufacturer's protocol (Stemcell, 19052). Purified $CD4^+$ T cells co-cultured with allogeneic iDCs were incubated with various concentrations of LAG-3 antibodies in 96-well plates. On Day 5, the culture supernatants were harvested for IFN-γ test. Human IFN-γ was measured by ELISA using matched antibody pairs. The recombinant IFN-γ was used as standard (Peprotech). The plates were pre-coated with capture antibody specific for human IFN-γ (Pierce-M700A). The biotin-conjugated anti-IFN-γ antibody (Pierce-M701B) was used as detecting antibody. The result shows that W3396-R2-1 and W3396-R2-13 are more potent than BMK Abs (W339-BMK1, W339-BMK7, W339-BMK8) in MLR assay (FIG. 8A). In a separate assay, as compared with isotype control, W3396-R2-1 and W3396-R2-2 promote human T cell IFN-γ secretion by ~50% and their potencies are comparable to BMK Abs (W339-BMK1, W339-BMK7, W339-BMK8) (FIG. 8B).

4.11 ADCC

Figure 9A:
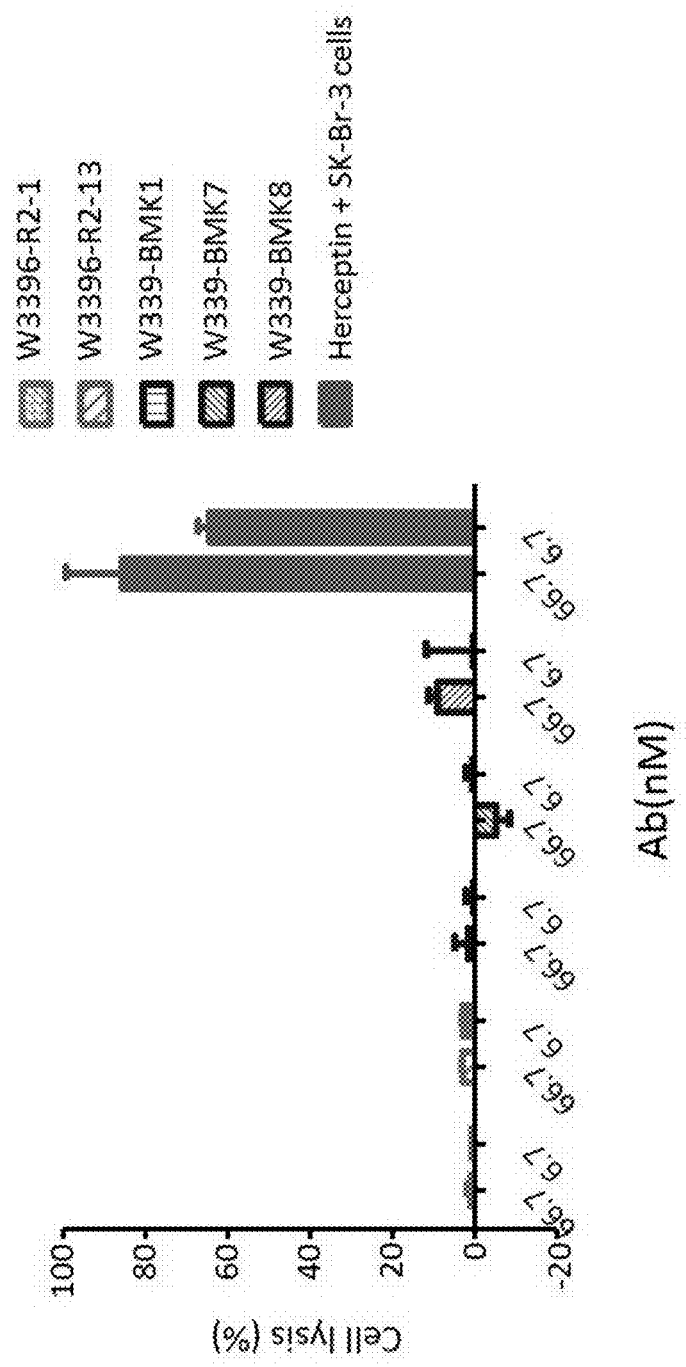
FIGS. 9A and 9B show that W3396-R2-1, W3396-R2-2 and W3396-R2-13 do not induce ADCC effect on human LAG-3 transfected cells, as measured by ADCC assay.
Figure 9B:
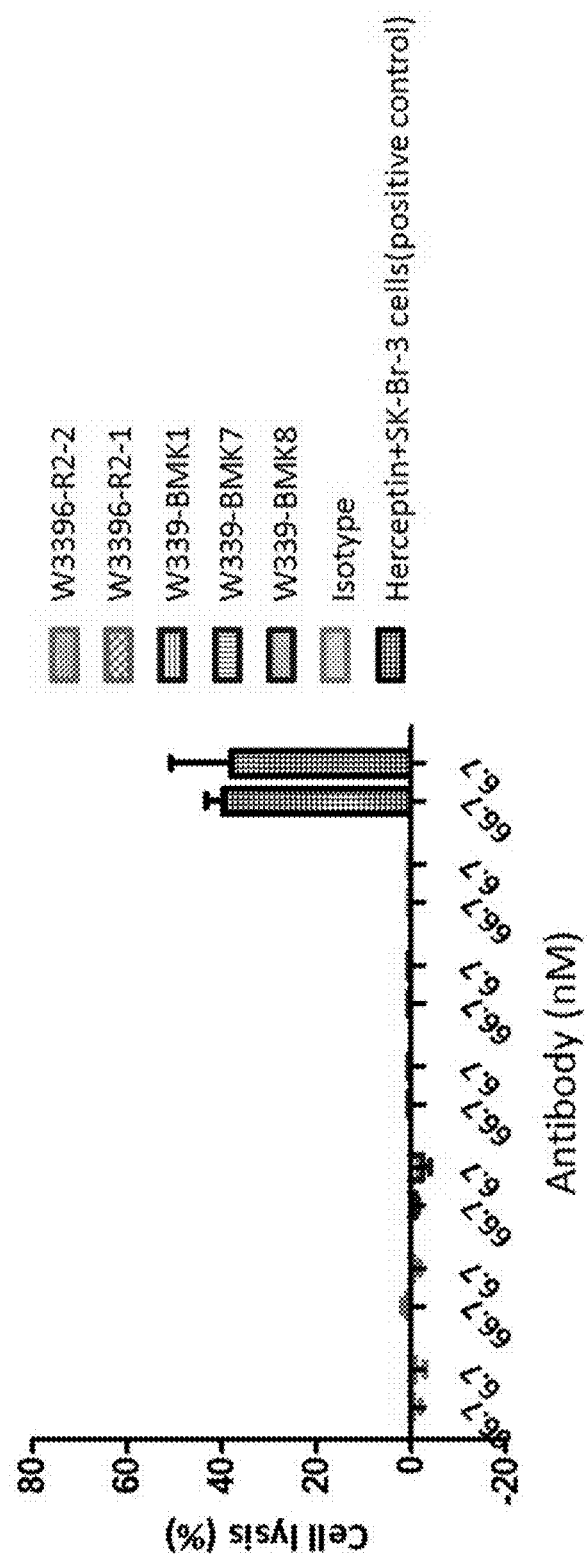

Human LAG-3 transfected cells and various concentrations of LAG-3 antibodies were pre-incubated in 96-well round-bottom plate for 30 minutes; and then PBMCs, as effector, were added with the effector/target ratio of 50:1. The plate was kept at 37° C., 5% $CO_2$ for 4 hours. Target cell lysis was determined by LDH-based Cytotoxicity Detection Kit (Roche-11644793001). The absorbance at 492 nm was read using a microplate reader. Herceptin and HER2-expressing cell line SK-Br-3 were used as positive control. W3396-R2-1, W3396-R2-2 and W3396-R2-13 Abs do not induce ADCC effect on human LAG-3 transfected cells (FIGS. 9A and 9B).

4.12 CDC Test

Figure 10A:
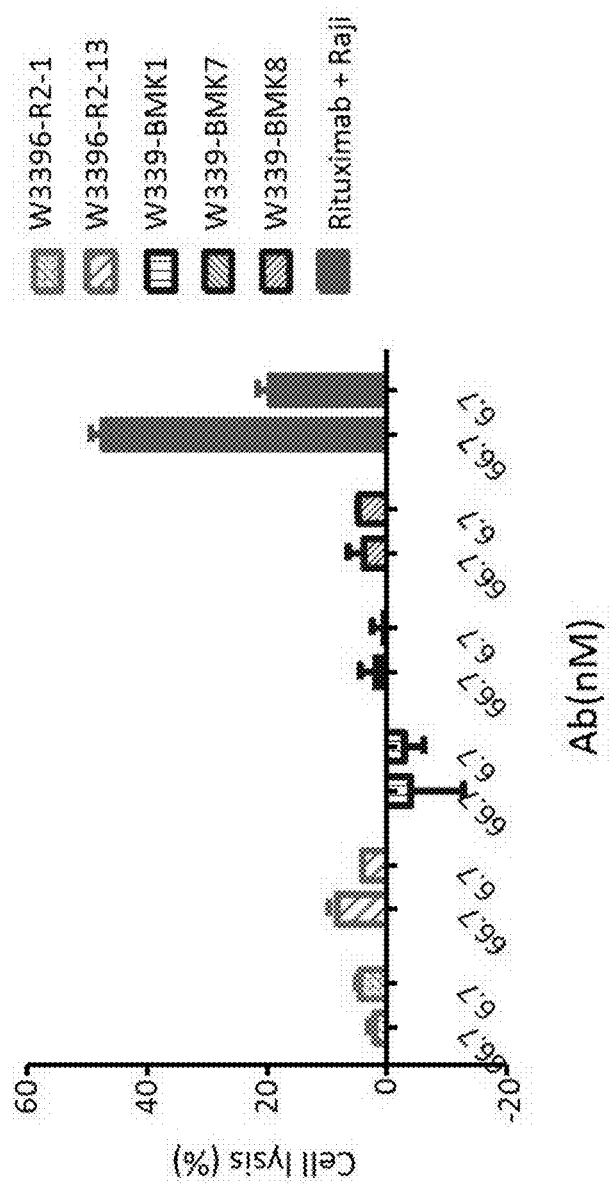
FIGS. 10A and 10B show that W3396-R2-1, W3396-R2-2 and W3396-R2-13 do not induce CDC effect on human LAG-3 transfected cells, as measured by CDC assay.
Figure 10B:
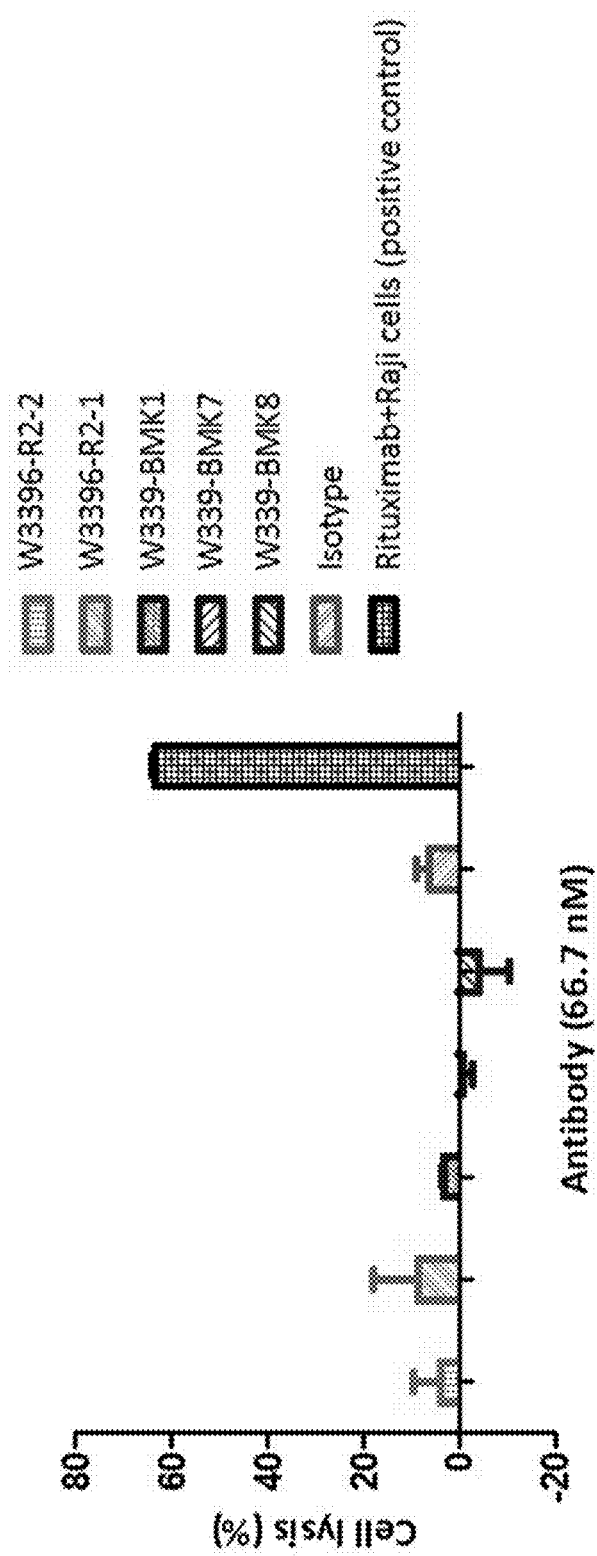

Human LAG-3 transfected cells and various concentrations of LAG-3 antibodies were mixed in 96-well round-bottom plate. Human complement was added at a final dilution of 1:50. The plate was kept at 37° C., 5% $CO_2$ for 2 hours. Target cell lysis was determined by Cell Titer-Glo (Promega). The luminescence was read using a microplate reader. Rituximab and CD20-expressing cell line Raji was used as positive control. W3396-R2-1, W3396-R2-2 and W3396-R2-13 do not induce CDC effect on human LAG-3 transfected cells (FIGS. 10A and 10B).

4.13 Serum Stability Test

Figure 11:
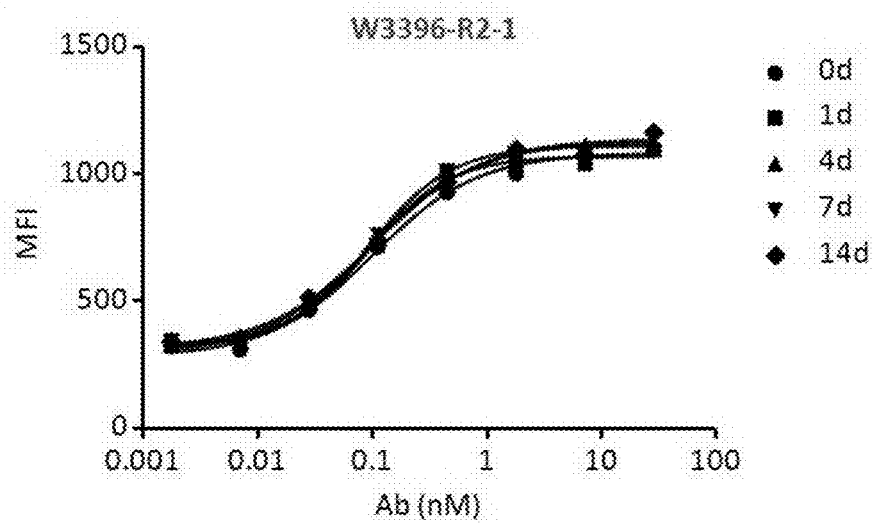
FIGS. 11A and 11B show that W3396-R2-1 and W3396-R2-13 remain stable in antigen binding capacity after incubation in human serum at 37° C. for 1 day, 4 days, 7 days and 14 days, as measured by FACS in serum stability test.
Figure 11:
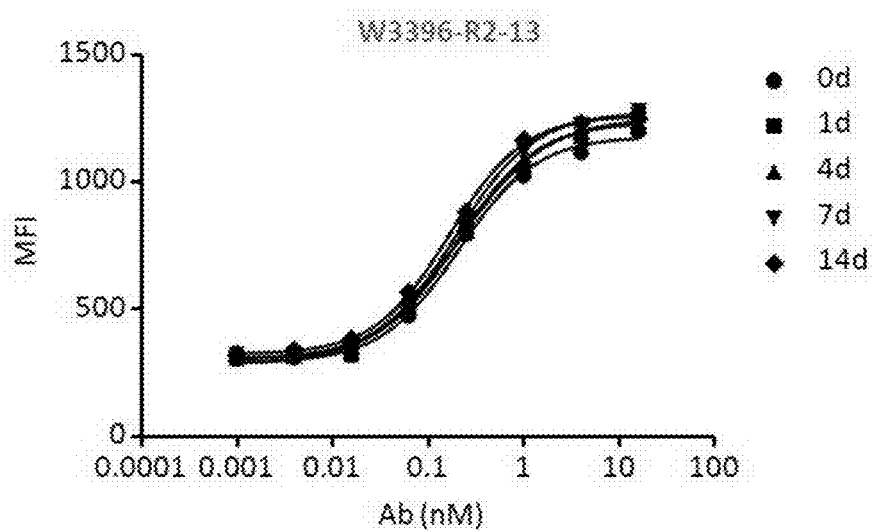
Figure 12A:
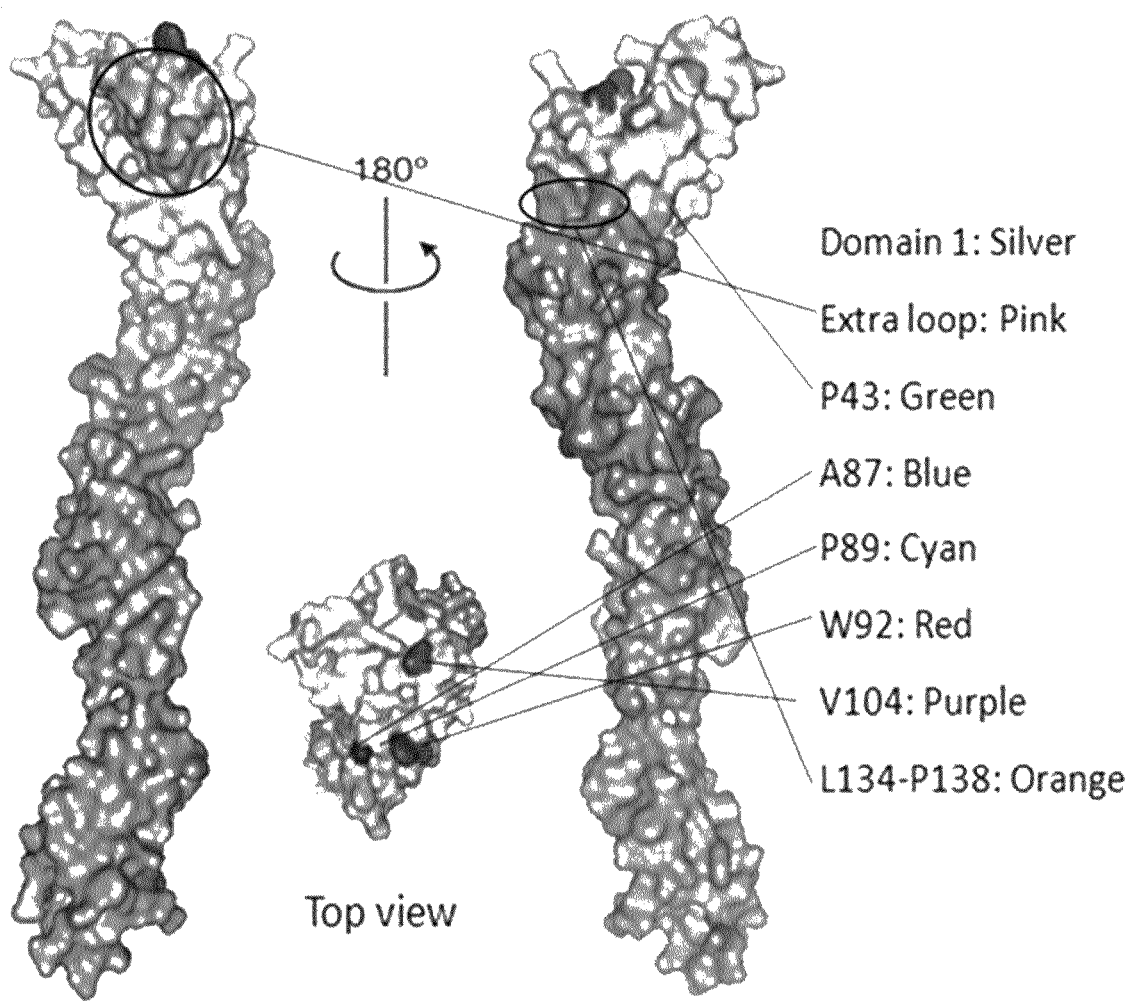
FIGS. 12A-12E show the result of epitope mapping.
Figure 12B:
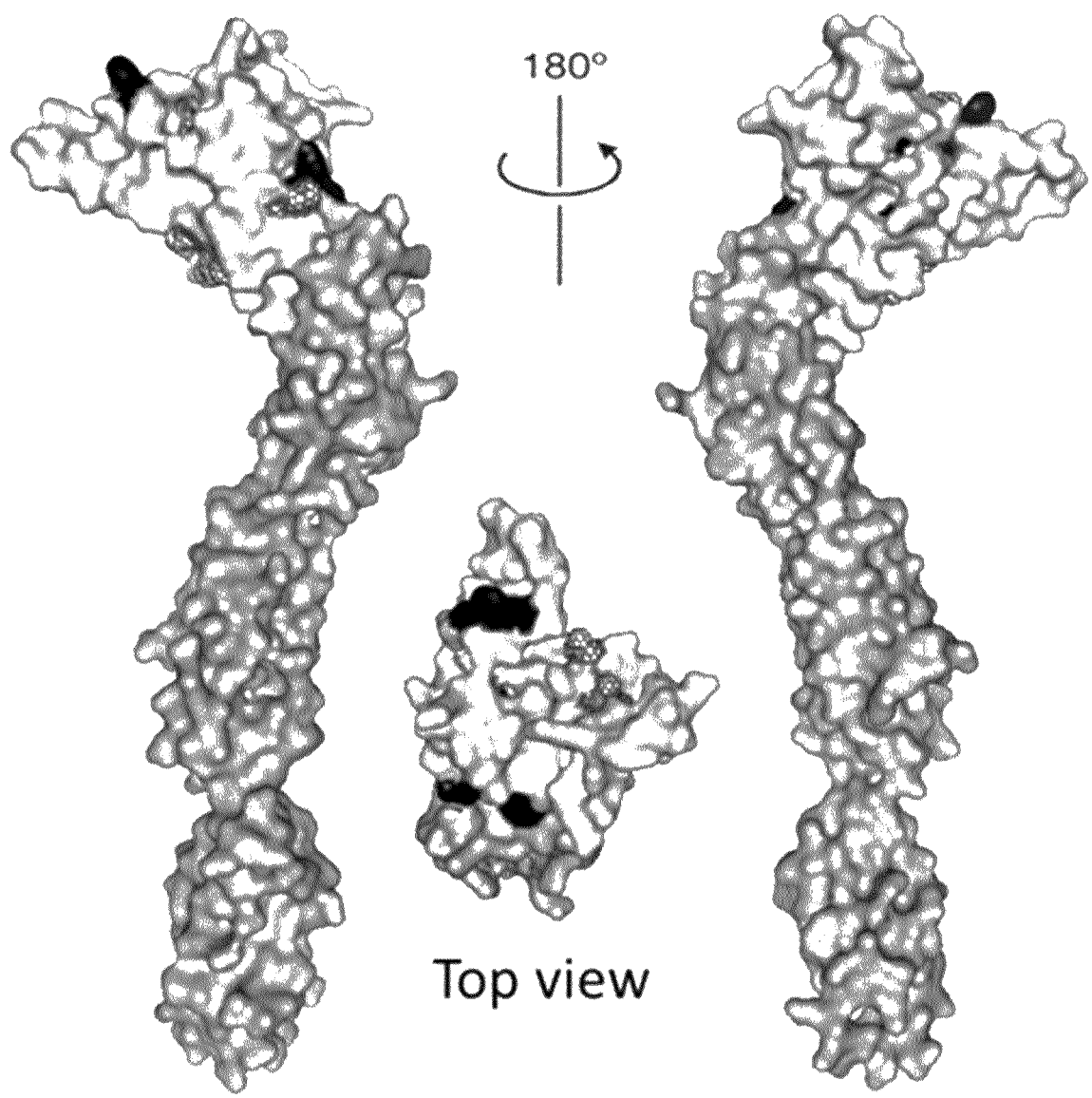
Figure 12C:
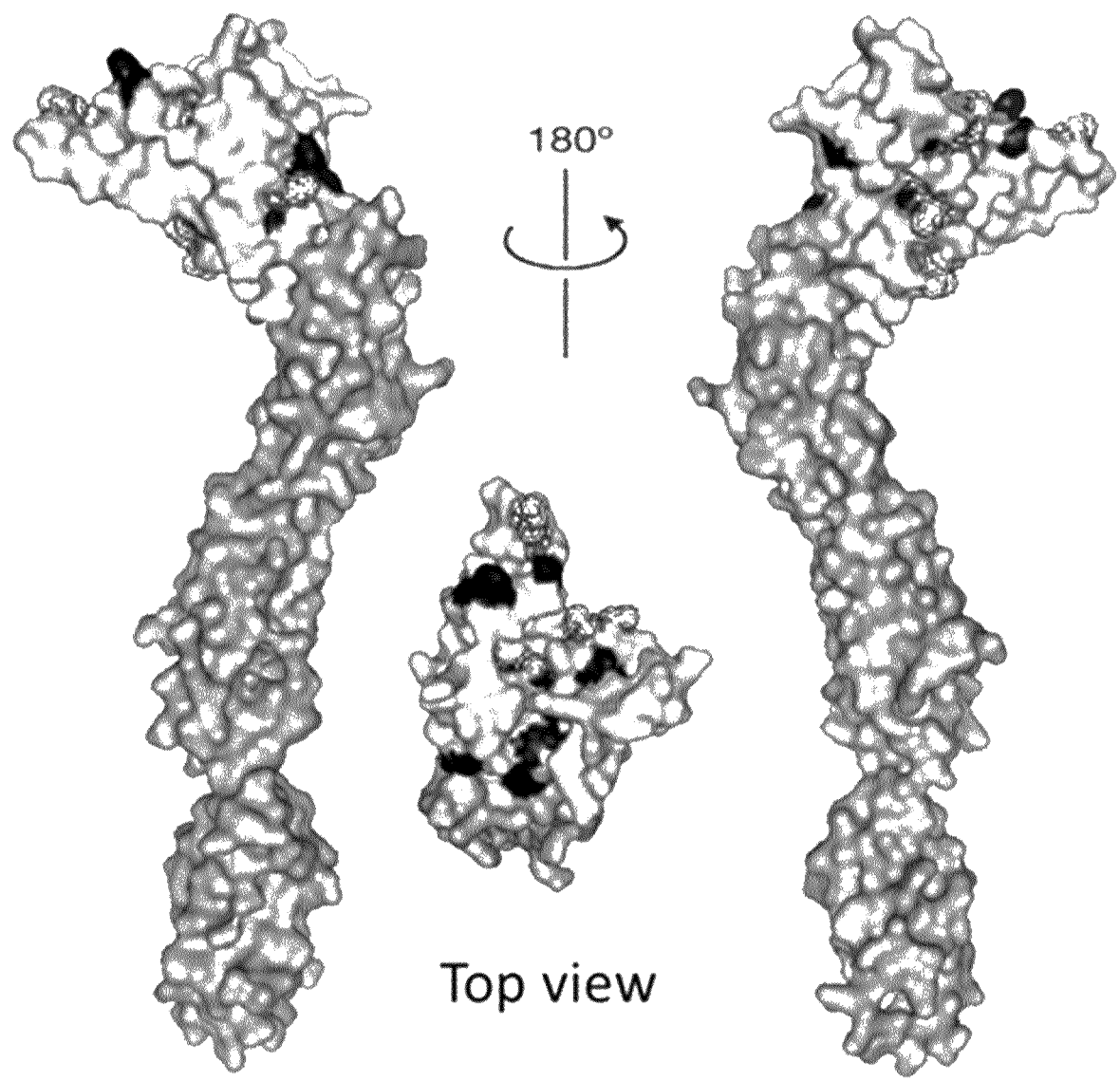
Figure 12D:
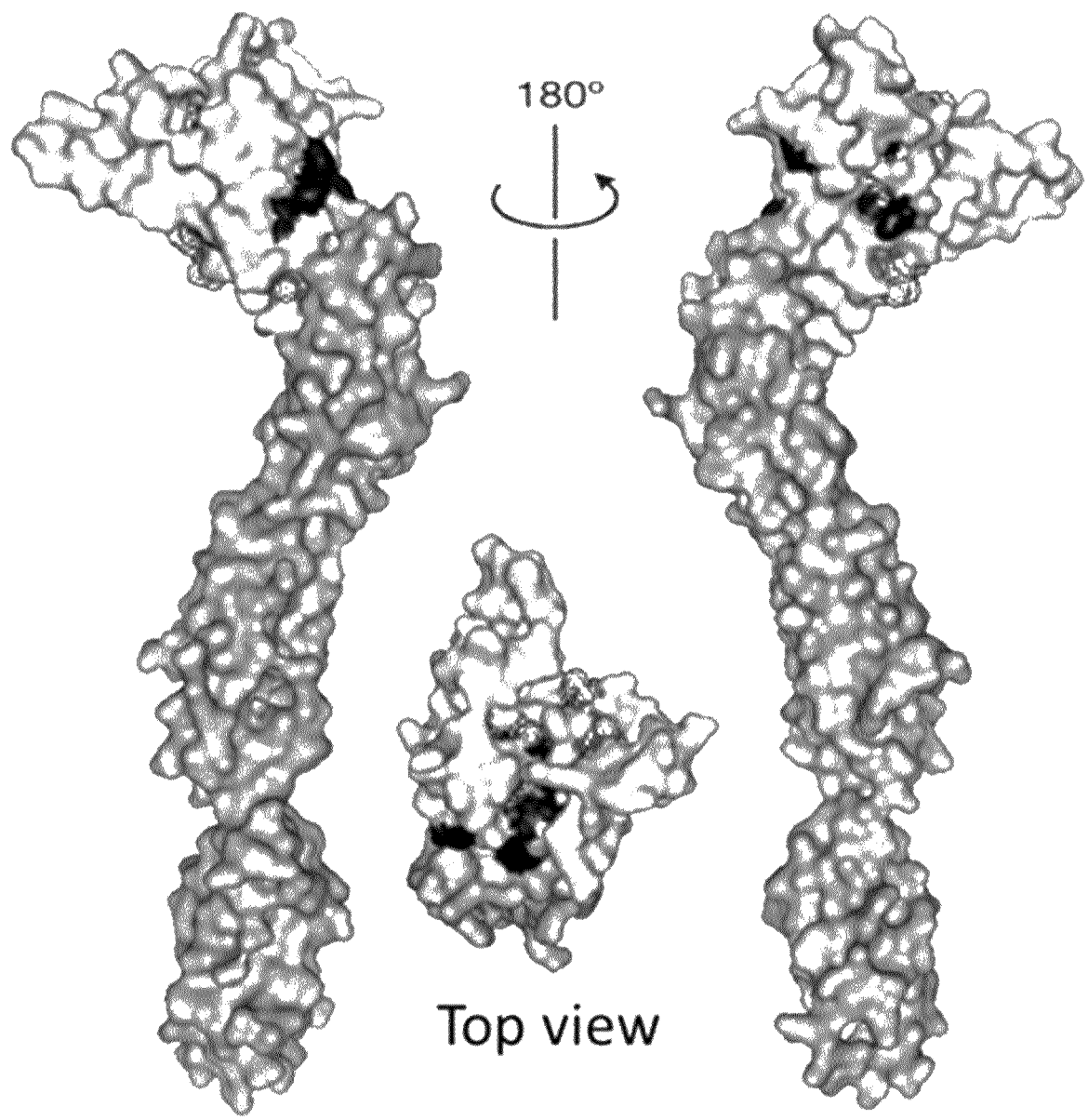
Figure 12E:
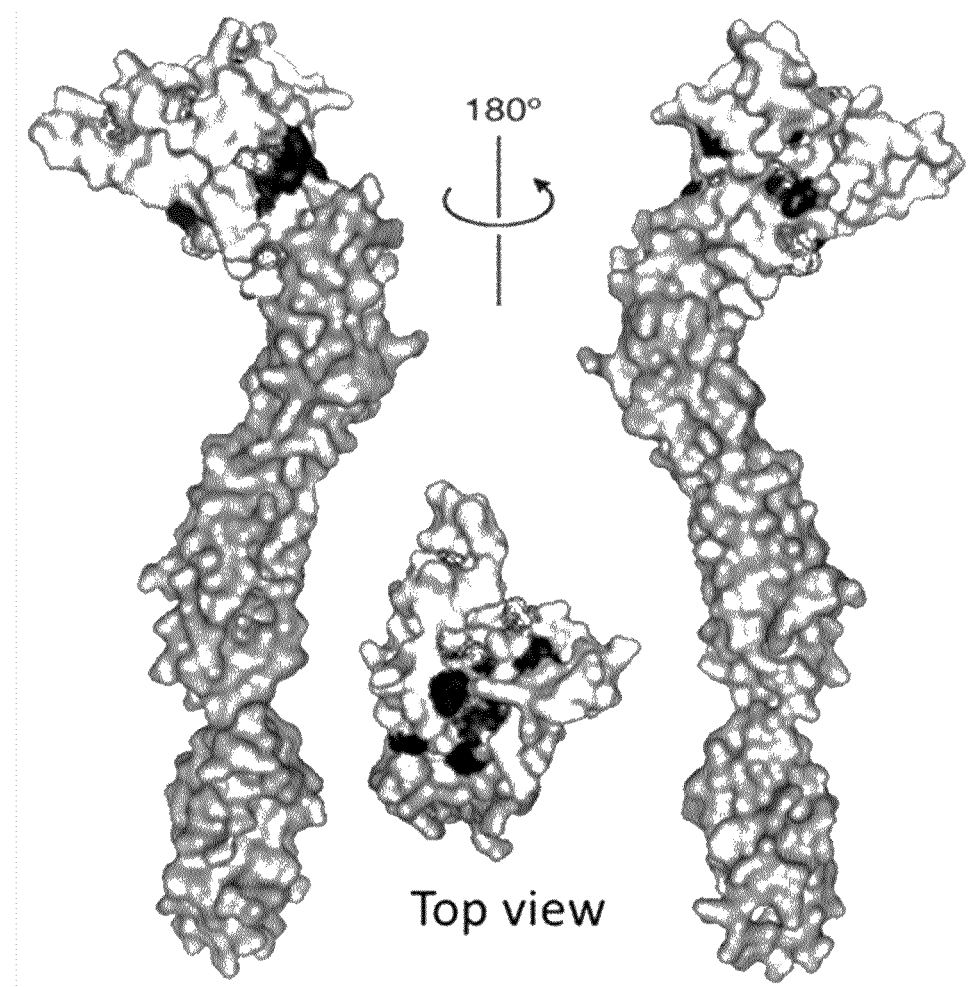

W3396-R2-1 and W3396-R2-13 were incubated in freshly isolated human serum (serum content >95%) at 37° C. On indicated time points (day 0, day 1, day 4, day 7 and day 14), an aliquot of serum treated sample were removed from the incubator and snap frozen in liquid N2, and then stored at −80° C. until ready for test. All the samples were quickly thawed prior to the stability test. Human LAG-3 transfected cells were incubated with fold-diluted and serum-treated W3396-R2-1 and W3396-R2-13 at 4° C. for 1 h. PE-labeled goat anti-human IgG was used to detect the binding of W3396-R2-1 and W3396-R2-13 onto the cells. MFI of the cells was measured by a flow cytometry and analyzed by FlowJo. The result shows that W3396-R2-1 (FIG. 11A) and W3396-R2-13 (FIG. 11B) are stable in human serum stability test.

4.14 Thermal Stability by Differential Scanning Fluorimetry (DSF) Assay

A DSF assay was performed using Real-Time Fluorescent Quantitative PCR (QuantStudio 7 Flex, Thermo Fisher Scientific). Briefly, 19 μL of antibody solution was mixed with 1 μL of 62.5×SYPRO Orange solution (Invitrogen) and added to a 96 well plate (Biosystems). The plate was heated from 26° C. to 95° C. at a rate of 2° C./min, and the resulting fluorescence data were collected. The negative derivatives of the fluorescence changes with respect to different temperatures were calculated, and the maximal value was defined as melting temperature $T_h$. If a protein has multiple unfolding transitions, the first two $T_h$ were reported, named as $T_{m1}$ and $T_{m2}$. $T_{m1}$ is melting temperature $T_m$ for comparisons between different proteins. Data collection and $T_h$ calculation were conducted automatically by operation software (QuantStudio™ Real-Time PCR PCR Software v1.3). The $T_m1$ and $T_m2$ values of W3396-R2-1, W3396-R2-2 and W3396-R2-13 in different buffers are shown in Table 7.

TABLE 7

Thermal stability by DSF

| Protein Name | Isotype | pI | Buffer | Concentration (mg/ml) | $T_m1$(° C.) | $T_m2$(° C.) |
|---|---|---|---|---|---|---|
| W3396-R2-1 | IgG4 | 6.02 | PBS + 0.2M Arginine | 1.0 | 60.5 | 71.0 |
| | | | 20 mM Histidine + 7% Sucrose pH 6.5 | 0.1 | 62.4 | 70.8 |
| | | | 50 mM NaAC + 7% Sucrose pH 5.6 | 0.1 | 61.5 | 69.0 |

TABLE 7-continued

Thermal stability by DSF

| Protein Name | Isotype | pI | Buffer | Concentration (mg/ml) | $T_m1(°C.)$ | $T_m2(°C.)$ |
|---|---|---|---|---|---|---|
| W3396-R2-2 | IgG4 | 6.02 | PBS | 4.2 | 62.1 | 68.5 |
| W3396-R2-13 | IgG4 | 6.21 | PBS | 3.7 | 62.3 | 68.0 |

4.15 In Vivo Pharmacokinetics (PK) Study in Mice

PK study of the testing antibodies was conducted in C57BL/6 mice. Female C57BL/6 mice (Beijing Vital River Laboratory Animal Technology Co., LTD) of 6-8 week-old were used in the study.

30 animals (10 animals/group) were divided into three groups: Group 1, Group 2 and Group 3. Animals were administered with W339-BMK1, W3396-R2-1 and W3396-R2-2 at 10 mg/kg once by intravenous injection, respectively. The Abs were formulated in PBS. PK blood samples were collected at pre-dose, 0.3 h, 2 h, 6 h, 24 h, D2(48 h), D4(96 h), D7(144 h), D10(240 h), D14(312 h), D21(480 h). Serum concentrations of W3396-R2-1 and W3396-R2-2 in serum samples were determined by ELISA. The day of injection was considered as day 0. All the procedures related to animal handling, care and the treatment in the study were performed according to the guidelines approved by the Institutional Animal Care and Use Committee (IACUC) of Biomodel following the guidance of the Association for Assessment and Accreditation of Laboratory Animal Care (AAALAC).

The serum concentration of W3396-R2-1, W3396-R2-2 and W339-BMK1 in mice was subjected to a non-compartmental pharmacokinetic analysis by using the Phoenix WinNonlin software (version 6.3, Pharsight, Mountain View, Calif.).

No adverse effects were observed during the study.

Figure 13:
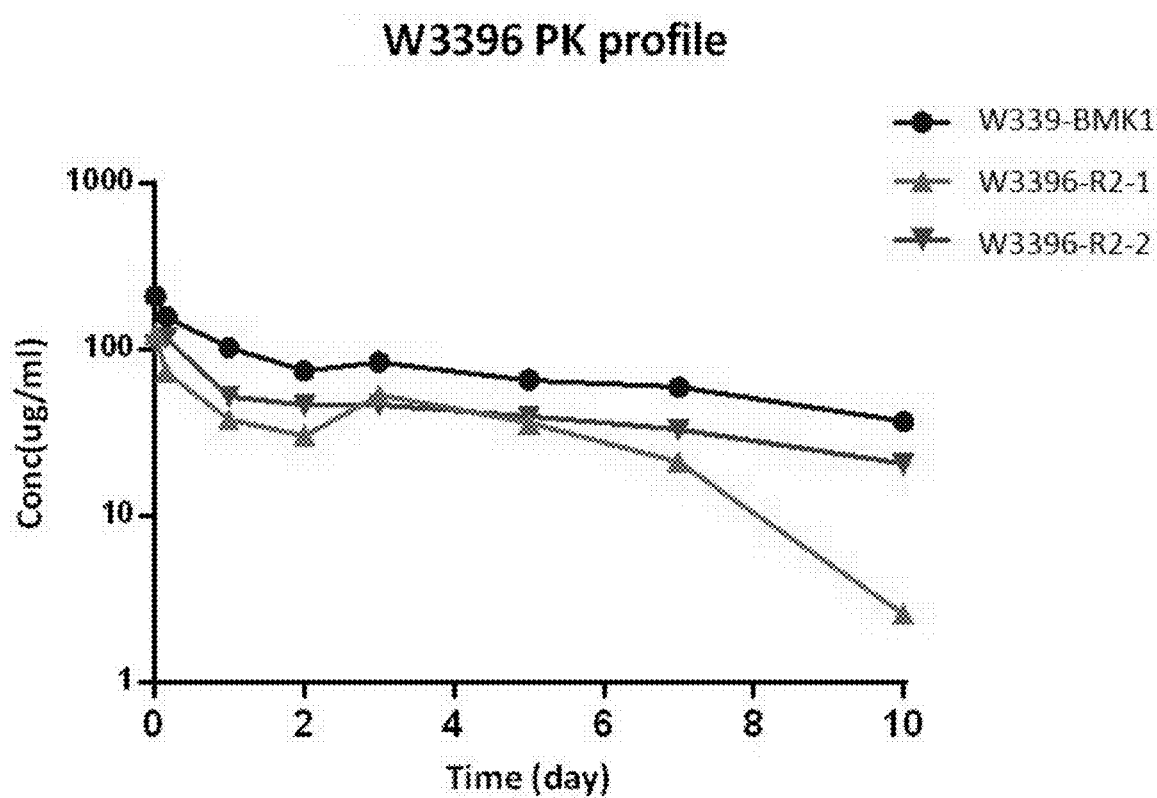
FIG. 13 shows that W3396-R2-2 and W339-BMK1 exhibit similar pharmacokinetic (PK) profile in mouse.

The summary for PK parameters was listed in the Table 8 and FIG. 13. The results indicates that W3396-R2-2 and W339-BMK1 show similar PK profile in mouse.

TABLE 8

The summary for PK parameters in mouse PK study

| Compound Dose | W339-BMK1.hIgG4.SP | W3396-R2-1 | W3396-R2-2 |
|---|---|---|---|
| | | 10 mg/kg i.v. | |
| $t_{1/2}$ (h) | 145 | 30.8 | 124 |
| $C_0$ (µg/mL) | 220 | 135 | 109 |
| $AUC_{0-t}$ (µg/ml*h) | 17397 | 7388 | 10105 |

4.16 A Single Dose Study of W3396-R2-1 and W3396-R2-2 in Naïve Male and Female Cynomolgus Monkeys Four naïve cynomolgus monkeys supplied by Hainan Jingang Laboratory Animal Co. Ltd. The body weights were in the range from 2.46 to 2.72 kg for males, range from 2.50 to 2.58 kg for females.

Four animals (2 animals/group) were divided into two groups: Group 1 and Group 2. Animals in Group 1 and Group 2 were administered with W3396-R2-1 and W3396-R2-2 at 30 mg/kg once by 30 min intravenous infusion, respectively. The formulations were formulated in PBS. PK blood samples were collected at pre-dose, 0.25 h, 1 h, 4 h, 8 h, 24 h, D3(48 h), D5(96 h), D7(144 h), D9(192 h), D11(240 h), D14(312 h), D21(480 h), D28(648 h). Antidrug antibody (ADA) samples were collected at pre-dose, D14 and D28. Serum concentrations of W3396-R2-1, W3396-R2-2 and ADA in serum samples were determined by ELISA. Samples for hematology and clinical chemistry tests were collected at pre-dose, 24 h, D3, D7, D14, D21, D28.

Cage-side observations for general health and appearance, especially skin irritation was observed. Whole blood sample analysis for hematology (CBC) and serum analysis for chemistry detection were determined by hematology analyzer (ADVIA2120) and chemistry (HITACHI 7180), respectively.

Approximately 1.0 mL blood for PK and 1.0 mL blood for anti-drug antibody (ADA) were collected at each time point via cephalic or saphenous vein from each study animal. The actual time for each sample collection were recorded. All sampling times were accepted (the deviations on sampling time were less than 1 min for the time points before or at 1 hour post-dose, and less than 5% of the nominal time for time points after 1 hour post-dose). All blood samples were transferred into commercial available tubes containing polymer silica activator. The tubes containing blood samples remained at room temperature for no more than 1 hour before centrifugation (until serum appeared). Serum samples were then prepared by centrifuging the blood samples at approximately 4° C., 2000 g for 20 minutes. All serum samples were then quickly frozen over dry ice and kept at −60° C. or lower until ELISA analysis.

All the procedures related to animal handling, care and the treatment in the study were performed according to the guidelines approved by the Institutional Animal Care and Use Committee (IACUC) of WuXi AppTec (Suzhou) following the guidance of the Association for Assessment and Accreditation of Laboratory Animal Care (AAALAC).

The serum concentration of W3396-R2-1, W3396-R2-2 in monkeys was subjected to a non-compartmental pharmacokinetic analysis by using the Phoenix WinNonlin software (version 6.3, Pharsight, Mountain View, Calif.). The linear/log trapezoidal rule was applied in obtaining the PK parameters. All BLQ values were excluded from the PK parameters calculations. All serum concentrations and pharmacokinetic parameters were reported with three significant figures. Individual BLQ was excluded from the calculation of the mean concentrations. The nominal dose levels and nominal sampling times were used in the calculation of all pharmacokinetic parameters.

Figure 14:
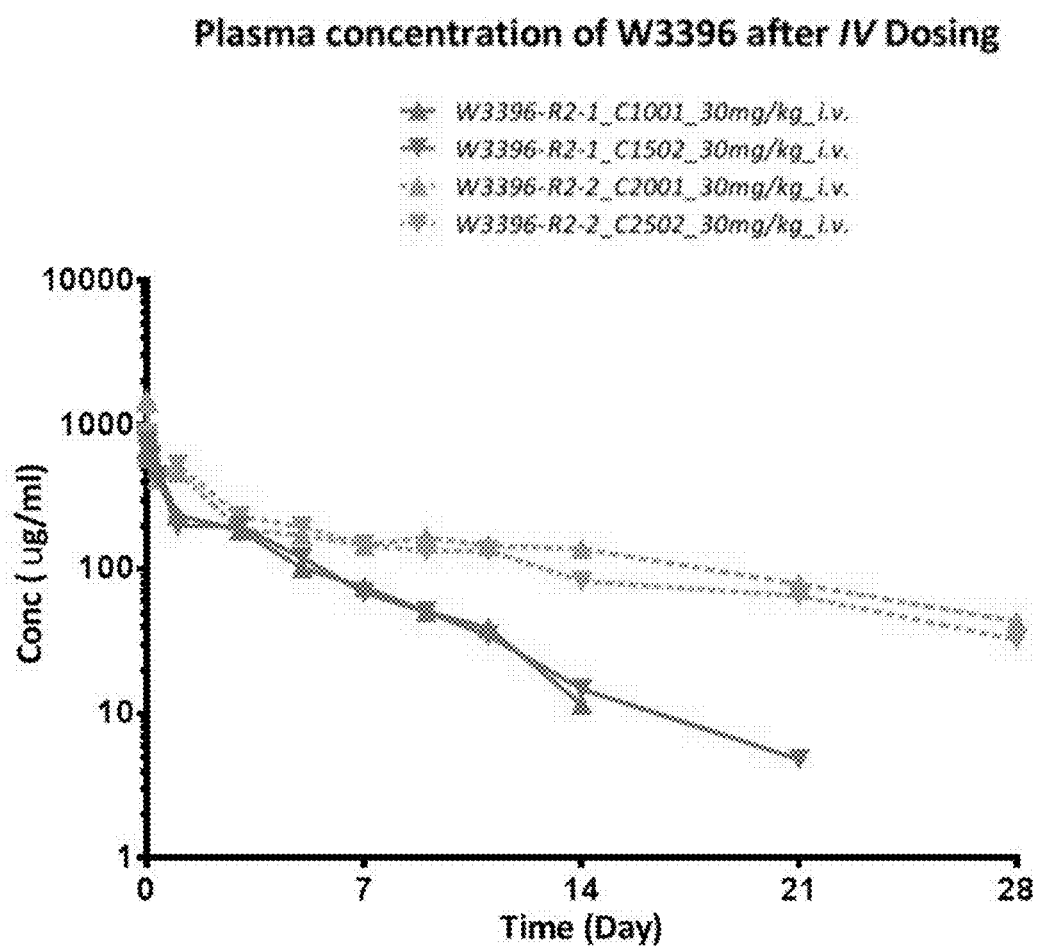
FIG. 14 shows that W3396-R2-2 has an in vivo half-life of about 212 hours in monkeys, as demonstrated in PK study in cynomolgus monkeys.

The result show that no adverse effects were observed during the study. There were no obvious change in food consumption and weight. The parameters for Hematology and Clinical Chemistry, including AST, ALT, WBC, HGB and HCT are generally within the reference range (data not shown). The summary for PK parameters was listed in the Table 9 and FIG. 14. The ADA titer in blood was summarized in Table 10. In conclusion, W3396-R2-2 shows a good T1/2 of about 212 hours in monkeys. The ADA titer of W3396-R2-2 is lower than that of W3396-R2-1 in monkeys.

TABLE 9

The summary of PK parameters (average) in monkey PK study

| PK parameters | Dose (mg/kg) | |
|---|---|---|
| | W3396-R2-1 30 mg/kg | W3396-R2-2 30 mg/kg |
| $C_{max}$ (μg/mL) | 725 | 769 |
| $T_{1/2}$ (h) | 76.5 | 212 |
| $Vd_{ss}$ (L/kg) | 0.0846 | 0.0945 |
| Cl (mL/min/kg) | 0.000188 | 0.00524 |
| $AUC_{0-last}$ (h*μg/mL) | 33574 | 84174 |
| $AUC_{0-inf}$ (h*μg/mL) | 34457 | 95676 |
| $MRT_{0-last}$ (h) | 87.3 | 213 |
| $MRT_{0-inf}$ (h) | 97.2 | 301 |

Abbreviations:
AUC The area under the serum concentration-time curve
$AUC_{0-last}$ The area under the serum concentration-time curve from time zero to the last quantifiable concentration
$AUC_{0-inf}$ The area under the serum concentration-time curve from time zero extrapolated to infinity were calculated using the linear/log trapezoidal rule
$C_0$ Maximum serum concentration
CL Total body clearance
ELISA Enzyme-linked immunosorbent assay
MRT Mean residence time
$MRT_{0-last}$ Mean residence time from time zero to the last quantifiable concentration
$MRT_{0-inf}$ Mean residence time from time zero to infinity
$T_{1/2}$ Half-life
$T_{max}$ Time to reach $C_{max}$
Vdss Volume of distribution at steady state

TABLE 10

Individual ADA result of W3396-R2-1 and W3396-R2-2 in cynomolgus monkeys following single intravenous bolus administration at 30 mg/kg

| | | | ADA Titer | |
|---|---|---|---|---|
| Compound | Dose | Animal ID | Day14 | Day28 |
| W3396-R2-1 | 30 mg/kg | C1001 | − | + |
| | | C1502 | − | + |
| W3396-R2-2 | 30 mg/kg | C2001 | − | + |
| | | C2502 | − | + |

Note:
"−" means ADA results were negative, "+" means ADA results were positive

---

What is claimed is:

1. An isolated single domain antibody polypeptide comprising a heavy chain variable domain that specifically binds to LAG-3, wherein the heavy chain variable domain comprises CDR1, CDR2 and CDR3, wherein
the CDR1 comprises the amino acid sequence of GLTLSQYTMG (SEQ ID NO: 1),
the CDR2 comprises the amino acid sequence of AIHWTSSVTDYADSV$X_1$G (SEQ ID NO:33), and
the CDR3 comprises the amino acid sequence of T$X_2$YYTHRG$X_3$FDY (SEQ ID NO:34),
wherein $X_1$ is K, Y, M, D, or R, $X_2$ is H or W, and $X_3$ is S or P.

2. The antibody polypeptide of claim 1, wherein:
the CDR1 comprises the sequence of SEQ ID NO: 1,
the CDR2 comprises a sequence selected from SEQ ID NOs: 2, 4, 8, 9, and 10, and
the CDR3 comprises a sequence selected from SEQ ID NOs: 3, 5, 6, and 7.

3. The antibody polypeptide of claim 1, comprising:
a) a heavy chain variable region comprising CDR1 comprising the amino acid sequence of SEQ ID NO: 1, CDR2 comprising the amino acid sequence of SEQ ID NO: 2, and CDR3 comprising the amino acid sequence of SEQ ID NO: 3;
b) a heavy chain variable region comprising CDR1 comprising the amino acid sequence of SEQ ID NO: 1, CDR2 comprising the amino acid sequence of SEQ ID NO: 4, and CDR3 comprising the amino acid sequence of SEQ ID NO: 5;
c) a heavy chain variable region comprising CDR1 comprising the amino acid sequence of SEQ ID NO: 1, CDR2 comprising the amino acid sequence of SEQ ID NO: 4, and CDR3 comprising the amino acid sequence of SEQ ID NO: 6;
d) a heavy chain variable region comprising CDR1 comprising the amino acid sequence of SEQ ID NO: 1, CDR2 comprising the amino acid sequence of SEQ ID NO: 4, and CDR3 comprising the amino acid sequence of SEQ ID NO: 7;
e) a heavy chain variable region comprising CDR1 comprising the amino acid sequence of SEQ ID NO: 1, CDR2 comprising the amino acid sequence of SEQ ID NO: 8, and CDR3 comprising the amino acid sequence of SEQ ID NO: 7;

f) a heavy chain variable region comprising CDR1 comprising the amino acid sequence of SEQ ID NO: 1, CDR2 comprising the amino acid sequence of SEQ ID NO: 9, and CDR3 comprising the amino acid sequence of SEQ ID NO: 5;

g) a heavy chain variable region comprising CDR1 comprising the amino acid sequence of SEQ ID NO: 1, CDR2 comprising the amino acid sequence of SEQ ID NO: 9, and CDR3 comprising the amino acid sequence of SEQ ID NO: 6;

h) a heavy chain variable region comprising CDR1 comprising the amino acid sequence of SEQ ID NO: 1, CDR2 comprising the amino acid sequence of SEQ ID NO: 9, and CDR3 comprising the amino acid sequence of SEQ ID NO: 7;

i) a heavy chain variable region comprising CDR1 comprising the amino acid sequence of SEQ ID NO: 1, CDR2 comprising the amino acid sequence of SEQ ID NO: 10, and CDR3 comprising the amino acid sequence of SEQ ID NO: 5; or j) a heavy chain variable region comprising CDR1 comprising the amino acid sequence of SEQ ID NO: 1, CDR2 comprising the amino acid sequence of SEQ ID NO: 4, and CDR3 comprising the amino acid sequence of SEQ ID NO: 3.

4. The antibody polypeptide of claim 1, comprising an amino acid sequence selected from the group consisting of SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 31.

5. The antibody polypeptide of claim 1, wherein the heavy chain variable domain is derived from a VHH domain.

6. The antibody polypeptide of claim 1, further comprising an immunoglobulin constant region, optionally a constant region of human Ig, or optionally an Fc region of human IgG.

7. The antibody polypeptide of claim 1, which is of camelid origin or is humanized.

8. The antibody polypeptide of claim 1, which is a nanobody.

9. The antibody polypeptide of claim 1, capable of specifically binding to human LAG-3 at a $K_D$ value of no more than $5\times10^{-9}$, $2\times10^{-10}$, $2.5\times10^{-12}$ M as measured by surface plasmon resonance (SPR).

10. The antibody polypeptide of claim 1, capable of specifically binding to human LAG-3 expressed on a cell surface at a $K_D$ value of no more than $10^{-9}$, $5\times10^{-10}$, $6\times10^{-11}$M as measured by flow cytometry.

11. The antibody polypeptide of claim 1, capable of specifically binding to cynomolgus monkey LAG-3, and/or mouse LAG-3.

12. The antibody polypeptide of claim 1, linked to one or more conjugate moieties.

13. The antibody polypeptide of claim 12, wherein the conjugate moiety selected from the group consisting of a clearance-modifying agent, a chemotherapeutic agent, a toxin, a radioactive isotope, a lanthanide, a luminescent label, a fluorescent label, an enzyme-substrate label, a DNA-alkylators, a topoisomerase inhibitor, a tubulin-binders, or an anticancer drug.

14. A pharmaceutical composition comprising the antibody polypeptide of claim 1, and a pharmaceutically acceptable carrier.

15. An isolated polynucleotide encoding the antibody polypeptide of claim 1.

16. The isolated polynucleotide of claim 15, comprising a nucleotide sequence selecting from a group consisting of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, and SEQ ID NO: 32.

17. A vector comprising the isolated polynucleotide of claim 15.

18. A host cell comprising the vector of claim 17.

19. A method of expressing the antibody polypeptide of claim 1, comprising culturing the host cell of claim 18 under the condition at which the vector of claim 17 is expressed.

20. A method of detecting presence or amount of LAG-3 in a sample, comprising contacting the sample with the antibody polypeptide of claim 1, and determining the presence or the amount of LAG-3 in the sample.

21. A method of diagnosing a Lag-3 related disease or condition in a subject, comprising: a) contacting a sample obtained from the subject with the antibody polypeptide of claim 1; b) determining presence or amount of LAG-3 in the sample; and c) correlating the presence or the amount of LAG-3 to existence or status of the LAG-3 related disease or condition in the subject.

22. A kit comprising the antibody polypeptide of claim 1, useful in detecting LAG-3.

* * * * *

SEQUENCE LISTING

<160> NUMBER OF SEQ ID NOS: 34

<210> SEQ ID NO 1
<211> LENGTH: 10
<212> TYPE: PRT
<213> ORGANISM: Lama glama

<400> SEQUENCE: 1

Gly Leu Thr Leu Ser Gln Tyr Thr Met Gly
1               5                   10

<210> SEQ ID NO 2
<211> LENGTH: 17
<212> TYPE: PRT
<213> ORGANISM: Lama glama

<400> SEQUENCE: 2

Ala Ile His Trp Thr Ser Ser Val Thr Asp Tyr Ala Asp Ser Val Lys
1               5                   10                  15

Gly

<210> SEQ ID NO 3
<211> LENGTH: 12
<212> TYPE: PRT
<213> ORGANISM: Lama glama

<400> SEQUENCE: 3

Thr His Tyr Tyr Thr His Arg Gly Ser Phe Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Ala Ile His Trp Thr Ser Ser Val Thr Asp Tyr Ala Asp Ser Val Tyr

```
1               5                   10                  15

Gly

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Thr Trp Tyr Tyr Thr His Arg Gly Ser Phe Asp Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Thr His Tyr Tyr Thr His Arg Gly Pro Phe Asp Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Thr Trp Tyr Tyr Thr His Arg Gly Pro Phe Asp Tyr
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Ala Ile His Trp Thr Ser Ser Val Thr Asp Tyr Ala Asp Ser Val Met
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Ala Ile His Trp Thr Ser Ser Val Thr Asp Tyr Ala Asp Ser Val Asp
1               5                   10                  15

Gly

<210> SEQ ID NO 10
<211> LENGTH: 17
<212> TYPE: PRT
<213> ORGANISM: Artificial Sequence
<220> FEATURE:
```

<223> OTHER INFORMATION: Synthetic

<400> SEQUENCE: 10

Ala Ile His Trp Thr Ser Ser Val Thr Asp Tyr Ala Asp Ser Val Arg
1               5                   10                  15

Gly

<210> SEQ ID NO 11
<211> LENGTH: 121
<212> TYPE: PRT
<213> ORGANISM: Lama glama

<400> SEQUENCE: 11

Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
        35                  40                  45

Ala Ala Ile His Trp Thr Ser Ser Val Thr Asp Tyr Ala Asp Ser Val
    50                  55                  60

Lys Gly Arg Phe Thr Ile Ser Arg Asp Asp Ala Arg Asn Thr Gly Tyr
65                  70                  75                  80

Leu Gln Met Asn Ser Leu Lys Phe Glu Asp Thr Ala Val Tyr Tyr Cys
                85                  90                  95

Ala Ala Thr His Tyr Tyr Thr His Arg Gly Ser Phe Asp Tyr Trp Gly
            100                 105                 110

Gln Gly Thr Gln Val Thr Val Ser Ser
        115                 120

<210> SEQ ID NO 12
<211> LENGTH: 363
<212> TYPE: DNA
<213> ORGANISM: Lama glama

<400> SEQUENCE: 12
caggtgcagc tggtggagtc cggggggagga ttggtgcagg ctggggggctc actgagactc      60 tcctgtgcag cctctggact gaccttgagt caatatacca tgggctggtt ccgccaggct      120
ccagggaagg agcgtgagtt ggtagcagct attcattgga ctagtagtgt caccgactat      180
gcagactccg tgaagggccg attcaccatc tccagagacg acgccaggaa cacgggctat      240
ctgcaaatga acagcctgaa atttgaggac acggccgttt attactgtgc agccacacac      300
tactacaccc acagaggaag cttcgactac tggggccagg ggacccaggt caccgtctcc      360
tca                                                                   363

<210> SEQ ID NO 13
<211> LENGTH: 121
<212> TYPE: PRT
<213> ORGANISM: Artificial Sequence
<220> FEATURE:
<223> OTHER INFORMATION: Synthetic

<400> SEQUENCE: 13

Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
            35                  40                  45

Ala Ala Ile His Trp Thr Ser Ser Val Thr Asp Tyr Ala Asp Ser Val
 50                  55                  60

Lys Gly Arg Phe Thr Ile Ser Arg Asp Asp Ser Lys Asn Thr Gly Tyr
65                  70                  75                  80

Leu Gln Met Asn Ser Leu Arg Ala Glu Asp Thr Ala Val Tyr Tyr Cys
                85                  90                  95

Ala Ala Thr His Tyr Tyr Thr His Arg Gly Ser Phe Asp Tyr Trp Gly
            100                 105                 110

Gln Gly Thr Leu Val Thr Val Ser Ser
            115                 120

<210> SEQ ID NO 14
<211> LENGTH: 363
<212> TYPE: DNA
<213> ORGANISM: Artificial Sequence
<220> FEATURE:
<223> OTHER INFORMATION: Synthetic

<400> SEQUENCE: 14
caagttcagc tggtggaaag cggcggtggt gttgttcagc cgggtggcag tctgcgtctg     60
agctgcgcag ccagtggtct gactttaagc cagtatacca tgggttggtt tcgccaagct    120
ccgggtaaag aacgcgaact ggtggccgcc attcattgga ccagcagcgt gaccgattat    180
gccgatagcg tgaaaggccg ctttaccatt agccgcgatg atagcaaaaa tactggttat    240
ctgcagatga attctttacg cgccgaagat accgccgtgt attactgcgc cgccacccat    300
tactataccc atcgcggcag ctttgattac tggggtcaag gtactttagt gaccgtgagc    360
agc                                                                 363

<210> SEQ ID NO 15
<211> LENGTH: 121
<212> TYPE: PRT
<213> ORGANISM: Artificial Sequence
<220> FEATURE:
<223> OTHER INFORMATION: Synthetic

<400> SEQUENCE: 15

Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
            35                  40                  45

Ala Ala Ile His Trp Thr Ser Ser Val Thr Asp Tyr Ala Asp Ser Val
 50                  55                  60

Tyr Gly Arg Phe Thr Ile Ser Arg Asp Asp Ser Lys Asn Thr Gly Tyr
65                  70                  75                  80

Leu Gln Met Asn Ser Leu Arg Ala Glu Asp Thr Ala Val Tyr Tyr Cys
                85                  90                  95

Ala Ala Thr Trp Tyr Tyr Thr His Arg Gly Ser Phe Asp Tyr Trp Gly
            100                 105                 110

Gln Gly Thr Leu Val Thr Val Ser Ser
            115                 120

<210> SEQ ID NO 16
<211> LENGTH: 363

```
<212> TYPE: DNA
<213> ORGANISM: Artificial Sequence
<220> FEATURE:
<223> OTHER INFORMATION: Synthetic

<400> SEQUENCE: 16
caagttcagc tggtggaaag cggcggtggt gttgttcagc cgggtggcag tctgcgtctg      60
agctgcgcag ccagtggtct gactttaagc cagtatacca tgggttggtt tcgccaagct    120
ccgggtaaag aacgcgaact ggtggccgcc attcattgga ccagcagcgt gaccgattat    180
gccgatagcg tgtacggccg ctttaccatt agccgcgatg atagcaaaaa tactggttat    240
ctgcagatga attctttacg cgccgaagat accgccgtgt attactgcgc cgccaccctg    300
tactataccc atcgcggcag ctttgattac tggggtcaag gtactttagt gaccgtgagc    360
agc                                                                  363

<210> SEQ ID NO 17
<211> LENGTH: 121
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
        35                  40                  45

Ala Ala Ile His Trp Thr Ser Ser Val Thr Asp Tyr Ala Asp Ser Val
    50                  55                  60

Tyr Gly Arg Phe Thr Ile Ser Arg Asp Asp Ser Lys Asn Thr Gly Tyr
65                  70                  75                  80

Leu Gln Met Asn Ser Leu Arg Ala Glu Asp Thr Ala Val Tyr Tyr Cys
                85                  90                  95

Ala Ala Thr His Tyr Tyr Thr His Arg Gly Pro Phe Asp Tyr Trp Gly
            100                 105                 110

Gln Gly Thr Leu Val Thr Val Ser Ser
        115                 120

<210> SEQ ID NO 18
<211> LENGTH: 363
<212> TYPE: DNA
<213> ORGANISM: Artificial Sequence
<220> FEATURE:
<223> OTHER INFORMATION: Synthetic

<400> SEQUENCE: 18
caagttcagc tggtggaaag cggcggtggt gttgttcagc cgggtggcag tctgcgtctg      60
agctgcgcag ccagtggtct gactttaagc cagtatacca tgggttggtt tcgccaagct    120
ccgggtaaag aacgcgaact ggtggccgcc attcattgga ccagcagcgt gaccgattat    180
gccgatagcg tgtacggccg ctttaccatt agccgcgatg atagcaaaaa tactggttat    240
ctgcagatga attctttacg cgccgaagat accgccgtgt attactgcgc cgccacccat    300
tactataccc atcgcggccc ctttgattac tggggtcaag gtactttagt gaccgtgagc    360
agc                                                                  363
```

<210> SEQ ID NO 19
<211> LENGTH: 121
<212> TYPE: PRT
<213> ORGANISM: Artificial Sequence
<220> FEATURE:
<223> OTHER INFORMATION: Synthetic

<400> SEQUENCE: 19

```
Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
        35                  40                  45

Ala Ala Ile His Trp Thr Ser Ser Val Thr Asp Tyr Ala Asp Ser Val
    50                  55                  60

Tyr Gly Arg Phe Thr Ile Ser Arg Asp Asp Ser Lys Asn Thr Gly Tyr
65                  70                  75                  80

Leu Gln Met Asn Ser Leu Arg Ala Glu Asp Thr Ala Val Tyr Tyr Cys
                85                  90                  95

Ala Ala Thr Trp Tyr Tyr Thr His Arg Gly Pro Phe Asp Tyr Trp Gly
            100                 105                 110

Gln Gly Thr Leu Val Thr Val Ser Ser
        115                 120
```

<210> SEQ ID NO 20
<211> LENGTH: 363
<212> TYPE: DNA
<213> ORGANISM: Artificial Sequence
<220> FEATURE:
<223> OTHER INFORMATION: Synthetic

<400> SEQUENCE: 20

```
caagttcagc tggtggaaag cggcggtggt gttgttcagc cgggtggcag tctgcgtctg      60
agctgcgcag ccagtggtct gactttaagc cagtatacca tgggttggtt tcgccaagct     120
ccgggtaaag aacgcgaact ggtggccgcc attcattgga ccagcagcgt gaccgattat     180
gccgatagcg tgtacggccg ctttaccatt agccgcgatg atagcaaaaa tactggttat     240
ctgcagatga attctttacg cgccgaagat accgccgtgt attactgcgc cgccacctgg     300
tactataccc atcgcggccc ctttgattac tggggtcaag gtactttagt gaccgtgagc     360
agc                                                                   363
```

<210> SEQ ID NO 21
<211> LENGTH: 121
<212> TYPE: PRT
<213> ORGANISM: Artificial Sequence
<220> FEATURE:
<223> OTHER INFORMATION: Synthetic

<400> SEQUENCE: 21

```
Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
        35                  40                  45

Ala Ala Ile His Trp Thr Ser Ser Val Thr Asp Tyr Ala Asp Ser Val
    50                  55                  60
```

```
Met Gly Arg Phe Thr Ile Ser Arg Asp Asp Ser Lys Asn Thr Gly Tyr
 65                  70                  75                  80

Leu Gln Met Asn Ser Leu Arg Ala Glu Asp Thr Ala Val Tyr Tyr Cys
                 85                  90                  95

Ala Ala Thr Trp Tyr Tyr Thr His Arg Gly Pro Phe Asp Tyr Trp Gly
            100                 105                 110

Gln Gly Thr Leu Val Thr Val Ser Ser
        115                 120
```

<210> SEQ ID NO 22
<211> LENGTH: 363
<212> TYPE: DNA
<213> ORGANISM: Artificial Sequence
<220> FEATURE:
<223> OTHER INFORMATION: Synthetic

<400> SEQUENCE: 22

```
caagttcagc tggtggaaag cggcggtggt gttgttcagc cgggtggcag tctgcgtctg    60
agctgcgcag ccagtggtct gactttaagc cagtatacca tgggttggtt tcgccaagct   120
ccgggtaaag aacgcgaact ggtggccgcc attcattgga ccagcagcgt gaccgattat   180
gccgatagcg tgatgggccg ctttaccatt agccgcgatg atagcaaaaa tactggttat   240
ctgcagatga attctttacg cgccgaagat accgccgtgt attactgcgc cgccacctgg   300 tactatccc atcgcggccc ctttgattac tggggtcaag gtactttagt gaccgtgagc   360
agc                                                                363
```

<210> SEQ ID NO 23
<211> LENGTH: 121
<212> TYPE: PRT
<213> ORGANISM: Artificial Sequence
<220> FEATURE:
<223> OTHER INFORMATION: Synthetic

<400> SEQUENCE: 23

```
Gln Val Gln Leu Val Glu Ser Gly Gly Gly Val Val Gln Pro Gly Gly
 1               5                  10                  15

Ser Leu Arg Leu Ser Cys Ala Ala Ser Gly Leu Thr Leu Ser Gln Tyr
                20                  25                  30

Thr Met Gly Trp Phe Arg Gln Ala Pro Gly Lys Glu Arg Glu Leu Val
            35                  40                  45

Ala Ala Ile His Trp Thr Ser Ser Val Thr Asp Tyr Ala Asp Ser Val
        50                  55                  60

Asp Gly Arg Phe Thr Ile Ser Arg Asp Asp Ser Lys Asn Thr Gly Tyr
 65                  70                  75                  80

Leu Gln Met Asn Ser Leu Arg Ala Glu Asp Thr Ala Val Tyr Tyr Cys
                 85                  90                  95

Ala Ala Thr Trp Tyr Tyr Thr His Arg Gly Ser Phe Asp Tyr Trp Gly
            100                 105                 110

Gln Gly Thr Leu Val Thr Val Ser Ser
        115                 120
```

<210> SEQ ID NO 24
<211> LENGTH: 363
<212> TYPE: DNA
<213> ORGANISM: Artificial Sequence
<220> FEATURE:
<223> OTHER INFORMATION: Synthetic

<400> SEQUENCE: 24

```
caagttcagc tggtggaaag cggcggtggt gttgttcagc cgggtggcag tctgcgtctg    60
agctgcgcag ccagtggtct gactttaagc cagtatacca tgggttggtt tcgccaagct   120
ccgggtaaag aacgcgaact ggtggccgcc attcattgga ccagcagcgt gaccgattat   180
gccgatagcg tggacggccg ctttaccatt agccgcgatg atagcaaaaa tactggttat   240
ctgcagatga attctttacg cgccgaagat accgccgtgt attactgcgc cgccacctgg   300
tactataccc atcgcggcag ctttgattac tggggtcaag gtactttagt gaccgtgagc   360
agc                                                                  363
```

<210> SEQ ID NO 25
<211> LENGTH: 121
<212> TYPE: PRT
<213> ORGANISM: Artificial Sequence
<220> FEATURE:
<223> OTHER INFORMATION: Synthetic

<400> SEQUENCE: 25

```
Gln Val Gln Leu Val Glu Ser Gly Gly Gly Val Val Gln Pro Gly Gly
1               5                  10                  15
Ser Leu Arg Leu Ser Cys Ala Ala Ser Gly Leu Thr Leu Ser Gln Tyr
            20                  25                  30
Thr Met Gly Trp Phe Arg Gln Ala Pro Gly Lys Glu Arg Glu Leu Val
        35                  40                  45
Ala Ala Ile His Trp Thr Ser Ser Val Thr Asp Tyr Ala Asp Ser Val
    50                  55                  60
Asp Gly Arg Phe Thr Ile Ser Arg Asp Asp Ser Lys Asn Thr Gly Tyr
65                  70                  75                  80
Leu Gln Met Asn Ser Leu Arg Ala Glu Asp Thr Ala Val Tyr Tyr Cys
                85                  90                  95
Ala Ala Thr His Tyr Tyr Thr His Arg Gly Pro Phe Asp Tyr Trp Gly
            100                 105                 110
Gln Gly Thr Leu Val Thr Val Ser Ser
        115                 120
```

<210> SEQ ID NO 26
<211> LENGTH: 363
<212> TYPE: DNA
<213> ORGANISM: Artificial Sequence
<220> FEATURE:
<223> OTHER INFORMATION: Synthetic

<400> SEQUENCE: 26

```
caagttcagc tggtggaaag cggcggtggt gttgttcagc cgggtggcag tctgcgtctg    60
agctgcgcag ccagtggtct gactttaagc cagtatacca tgggttggtt tcgccaagct   120
ccgggtaaag aacgcgaact ggtggccgcc attcattgga ccagcagcgt gaccgattat   180
gccgatagcg tggacggccg ctttaccatt agccgcgatg atagcaaaaa tactggttat   240
ctgcagatga attctttacg cgccgaagat accgccgtgt attactgcgc cgccacccat   300
tactataccc atcgcggccc ctttgattac tggggtcaag gtactttagt gaccgtgagc   360
agc                                                                  363
```

<210> SEQ ID NO 27
<211> LENGTH: 121
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
        35                  40                  45

Ala Ala Ile His Trp Thr Ser Ser Val Thr Asp Tyr Ala Asp Ser Val
    50                  55                  60

Asp Gly Arg Phe Thr Ile Ser Arg Asp Asp Ser Lys Asn Thr Gly Tyr
65                  70                  75                  80

Leu Gln Met Asn Ser Leu Arg Ala Glu Asp Thr Ala Val Tyr Tyr Cys
                85                  90                  95

Ala Ala Thr Trp Tyr Tyr Thr His Arg Gly Pro Phe Asp Tyr Trp Gly
            100                 105                 110

Gln Gly Thr Leu Val Thr Val Ser Ser
        115                 120

<210> SEQ ID NO 28
<211> LENGTH: 363
<212> TYPE: DNA
<213> ORGANISM: Artificial Sequence
<220> FEATURE:
<223> OTHER INFORMATION: Synthetic

<400> SEQUENCE: 28
caagttcagc tggtggaaag cggcggtggt gttgttcagc cgggtggcag tctgcgtctg      60
agctgcgcag ccagtggtct gactttaagc cagtatacca tgggttggtt tcgccaagct     120
ccgggtaaag aacgcgaact ggtggccgcc attcattgga ccagcagcgt gaccgattat     180
gccgatagcg tggacggccg ctttaccatt agccgcgatg atagcaaaaa tactggttat     240
ctgcagatga attctttacg cgccgaagat accgccgtgt attactgcgc cgccacctgg     300
tactataccc atcgcggccc ctttgattac tgggtcaag gtactttagt gaccgtgagc      360
agc                                                                   363

<210> SEQ ID NO 29
<211> LENGTH: 121
<212> TYPE: PRT
<213> ORGANISM: Artificial Sequence
<220> FEATURE:
<223> OTHER INFORMATION: Synthetic

<400> SEQUENCE: 29

Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
        35                  40                  45

Ala Ala Ile His Trp Thr Ser Ser Val Thr Asp Tyr Ala Asp Ser Val
    50                  55                  60

Arg Gly Arg Phe Thr Ile Ser Arg Asp Asp Ser Lys Asn Thr Gly Tyr
65                  70                  75                  80

Leu Gln Met Asn Ser Leu Arg Ala Glu Asp Thr Ala Val Tyr Tyr Cys

```
                85                  90                  95
Ala Ala Thr Trp Tyr Tyr Thr His Arg Gly Ser Phe Asp Tyr Trp Gly
            100                 105                 110

Gln Gly Thr Leu Val Thr Val Ser Ser
            115                 120

<210> SEQ ID NO 30
<211> LENGTH: 363
<212> TYPE: DNA
<213> ORGANISM: Artificial Sequence
<220> FEATURE:
<223> OTHER INFORMATION: Synthetic

<400> SEQUENCE: 30
caagttcagc tggtggaaag cggcggtggt gttgttcagc cgggtggcag tctgcgtctg      60
agctgcgcag ccagtggtct gactttaagc cagtatacca tgggttggtt tcgccaagct    120
ccgggtaaag aacgcgaact ggtggccgcc attcattgga ccagcagcgt gaccgattat    180
gccgatagcg tgcggggccg ctttaccatt agccgcgatg atagcaaaaa tactggttat    240
ctgcagatga attctttacg cgccgaagat accgccgtgt attactgcgc cgccacctgg    300
tactataccc atcgcggcag ctttgattac tggggtcaag gtactttagt gaccgtgagc    360
agc                                                                  363

<210> SEQ ID NO 31
<211> LENGTH: 121
<212> TYPE: PRT
<213> ORGANISM: Artificial Sequence
<220> FEATURE:
<223> OTHER INFORMATION: Synthetic

<400> SEQUENCE: 31

Gln Val Gln Leu Val Glu Ser Gly Gly Gly Val Val Gln Pro Gly Gly
1               5                  10                  15

Ser Leu Arg Leu Ser Cys Ala Ala Ser Gly Leu Thr Leu Ser Gln Tyr
            20                  25                  30

Thr Met Gly Trp Phe Arg Gln Ala Pro Gly Lys Glu Arg Glu Leu Val
        35                  40                  45

Ala Ala Ile His Trp Thr Ser Ser Val Thr Asp Tyr Ala Asp Ser Val
    50                  55                  60

Tyr Gly Arg Phe Thr Ile Ser Arg Asp Asp Ser Lys Asn Thr Gly Tyr
65                  70                  75                  80

Leu Gln Met Asn Ser Leu Arg Ala Glu Asp Thr Ala Val Tyr Tyr Cys
                85                  90                  95

Ala Ala Thr His Tyr Tyr Thr His Arg Gly Ser Phe Asp Tyr Trp Gly
            100                 105                 110

Gln Gly Thr Leu Val Thr Val Ser Ser
            115                 120

<210> SEQ ID NO 32
<211> LENGTH: 363
<212> TYPE: DNA
<213> ORGANISM: Artificial Sequence
<220> FEATURE:
<223> OTHER INFORMATION: Synthetic

<400> SEQUENCE: 32
caagttcagc tggtggaaag cggcggtggt gttgttcagc cgggtggcag tctgcgtctg      60
agctgcgcag ccagtggtct gactttaagc cagtatacca tgggttggtt tcgccaagct    120
```

```
ccgggtaaag aacgcgaact ggtggccgcc attcattgga ccagcagcgt gaccgattat    180
gccgatagcg tgtacggccg ctttaccatt agccgcgatg atagcaaaaa tactggttat    240
ctgcagatga attctttacg cgccgaagat accgccgtgt attactgcgc cgccacccat    300
tactataccc atcgcggcag ctttgattac tggggtcaag gtactttagt gaccgtgagc    360
agc                                                                   363
```

```
<210> SEQ ID NO 33
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: Xaa can be Lys, Tyr, Met, Asp, or Arg

<400> SEQUENCE: 33

Ala Ile His Trp Thr Ser Ser Val Thr Asp Tyr Ala Asp Ser Val Xaa
1               5                   10                  15
Gly

<210> SEQ ID NO 34
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa in location 2 can be His or Trp
<220> FEATURE:
<221> NAME/KEY: misc_feature
<222> LOCATION: (9)..(9)
<223> OTHER INFORMATION: Xaa in location 9 can be Ser or Pro

<400> SEQUENCE: 34

Thr Xaa Tyr Tyr Thr His Arg Gly Xaa Phe Asp Tyr
1               5                   10
```